US010525233B2

(12) United States Patent
Barrish et al.

(10) Patent No.: US 10,525,233 B2
(45) Date of Patent: Jan. 7, 2020

(54) INPUT AND ARTICULATION SYSTEM FOR CATHETERS AND OTHER USES

(71) Applicant: Project Moray, Inc., Belmont, CA (US)

(72) Inventors: Mark D. Barrish, Belmont, CA (US); Keith Phillip Laby, Oakland, CA (US)

(73) Assignee: Project Moray, Inc., Belmont, CA (US)

( * ) Notice: Subject to any disclaimer, the term of this patent is extended or adjusted under 35 U.S.C. 154(b) by 160 days.

(21) Appl. No.: 15/369,606

(22) Filed: Dec. 5, 2016

(65) Prior Publication Data
US 2017/0157361 A1 Jun. 8, 2017

Related U.S. Application Data

(60) Provisional application No. 62/263,231, filed on Dec. 4, 2015, provisional application No. 62/326,551, filed on Apr. 22, 2016.

(51) Int. Cl.
*A61M 31/00* (2006.01)
*A61M 37/00* (2006.01)
(Continued)

(52) U.S. Cl.
CPC ... *A61M 25/0136* (2013.01); *A61B 17/00234* (2013.01); *A61B 34/20* (2016.02);
(Continued)

(58) Field of Classification Search
CPC .. A61B 2017/00318; A61B 2034/2048; A61B 34/20; A61B 34/30; A61M 25/0116; A61M 25/0136; A61M 25/0155
See application file for complete search history.

(56) References Cited

U.S. PATENT DOCUMENTS 3,284,964 A 11/1966 Saito
3,459,221 A 8/1969 Axelrod
(Continued)

FOREIGN PATENT DOCUMENTS

WO 2007053625 5/2007
WO 2014128507 8/2014
(Continued)

OTHER PUBLICATIONS

"3-D printing of electrically conductive materials literature review", Appropedia: The sustainability Wiki, by Michigan Tech's Open Sustainability Technology Lab., 9 pages.
(Continued)

*Primary Examiner* — Rebecca E Eisenberg
(74) *Attorney, Agent, or Firm* — Kilpatrick Townsend & Stockton LLP

(57) ABSTRACT

User interface devices, systems, and methods can be used for selectively bending of, altering the bend characteristics of, and/or altering the lengths of catheter bodies, guidewires, steerable trocars, and other flexible structures inserted into a patient during use. Optionally, a housing is coupled to a proximal end of a catheter, and movement of the housing by a hand of a system user is sensed and used as a movement command for articulation of the catheter. Alternatively, a sensor can be coupled to an elongate flexible body flexing outside of the patient so as to alter bending of a catheter within the patient. Movements generated through a combination of manual manipulation and powered articulations are facilitated.

20 Claims, 42 Drawing Sheets

(51) Int. Cl.
*A61M 25/01* (2006.01)
*A61B 34/20* (2016.01)
*A61B 17/00* (2006.01)

(52) U.S. Cl.
CPC .... *A61M 25/0116* (2013.01); *A61M 25/0155* (2013.01); *A61B 2017/00309* (2013.01); *A61B 2017/00314* (2013.01); *A61B 2017/00318* (2013.01); *A61B 2034/2048* (2016.02)

(56) References Cited

U.S. PATENT DOCUMENTS

| | | | |
|---|---|---|---|
| 3,523,547 A | 8/1970 | Hatch et al. | |
| 3,915,194 A | 10/1975 | Friedrich | |
| 3,934,605 A | 1/1976 | Legris | |
| 4,082,324 A | 4/1978 | Obrecht | |
| 4,230,143 A | 10/1980 | Dettmann et al. | |
| 4,494,417 A | 1/1985 | Larson et al. | |
| 4,762,130 A | 8/1988 | Fogarty et al. | |
| 4,784,042 A | 11/1988 | Paynter | |
| 4,794,912 A | 1/1989 | Lia | |
| 4,838,859 A | 6/1989 | Strassmann | |
| 4,893,613 A | 1/1990 | Hake | |
| 4,900,218 A | 2/1990 | Sutherland | |
| 4,983,165 A | 1/1991 | Loiterman | |
| 5,018,506 A | 5/1991 | Danna et al. | |
| 5,304,132 A | 4/1994 | Jang | |
| 5,337,733 A | 8/1994 | Bauerfeind et al. | |
| 5,469,756 A | 11/1995 | Feiten | |
| 5,501,667 A | 3/1996 | Verduin, Jr. | |
| 5,529,088 A | 6/1996 | Asou | |
| 5,619,993 A | 4/1997 | Lee | |
| 6,066,125 A | 5/2000 | Webster, Jr. | |
| 6,146,339 A | 11/2000 | Biagtan et al. | |
| 6,178,872 B1 | 1/2001 | Schulz | |
| 6,424,885 B1 | 7/2002 | Niemeyer et al. | |
| 6,503,194 B2 | 1/2003 | Pauker | |
| 6,811,550 B2 | 11/2004 | Holland et al. | |
| 6,875,170 B2 | 4/2005 | Francois et al. | |
| 6,928,313 B2 | 8/2005 | Peterson | |
| 6,951,226 B2 | 10/2005 | Eriksson et al. | |
| 7,060,062 B2 | 6/2006 | Joye et al. | |
| 7,373,955 B2 | 5/2008 | Steinberg | |
| 7,570,981 B2 | 8/2009 | Peterson | |
| 7,578,787 B2 | 8/2009 | Boese et al. | |
| 7,780,723 B2 | 8/2010 | Taylor | |
| 7,824,391 B2 | 11/2010 | Gesswein | |
| 7,850,683 B2 | 12/2010 | Elkins et al. | |
| 7,879,004 B2 | 2/2011 | Seibel et al. | |
| 7,957,790 B2 | 6/2011 | Kleen | |
| 7,963,911 B2 | 6/2011 | Turliuc | |
| 8,125,755 B2 | 2/2012 | Garcia et al. | |
| 8,201,473 B2 | 6/2012 | Knoll | |
| 8,372,055 B2 | 2/2013 | Thornton et al. | |
| 8,388,520 B2 | 3/2013 | Stefanchik et al. | |
| 8,398,540 B2 | 3/2013 | Hassidov et al. | |
| 8,469,059 B1 | 6/2013 | Forst | |
| 8,764,725 B2 | 7/2014 | Averbuch | |
| 8,845,523 B2 | 9/2014 | Lawrence et al. | |
| 8,863,608 B2 | 10/2014 | Fischer et al. | |
| 9,533,122 B2 * | 1/2017 | Weitzner | A61M 25/0136 |
| 2002/0049408 A1 | 4/2002 | Van Moorlegem et al. | |
| 2003/0069475 A1 * | 4/2003 | Banik | A61B 1/00016 |
| | | | 600/152 |
| 2007/0060997 A1 | 3/2007 | de Boer et al. | |
| 2007/0100235 A1 | 5/2007 | Kennedy, II | |
| 2007/0169761 A1 | 7/2007 | Price | |
| 2007/0270686 A1 | 11/2007 | Ritter et al. | |
| 2008/0091073 A1 | 4/2008 | Park | |
| 2010/0013764 A1 | 1/2010 | Gu et al. | |
| 2011/0295247 A1 | 12/2011 | Schlesinger et al. | |
| 2011/0295248 A1 | 12/2011 | Wallace et al. | |
| 2012/0310227 A1 | 12/2012 | Katou | |
| 2013/0091974 A1 | 4/2013 | Riwan et al. | |
| 2013/0096377 A1 | 4/2013 | Duindam et al. | |
| 2013/0103019 A1 | 4/2013 | Joye et al. | |
| 2013/0296983 A1 | 11/2013 | Keller et al. | |
| 2013/0321262 A1 | 12/2013 | Schecter | |
| 2014/0142666 A1 | 5/2014 | Phelan et al. | |
| 2014/0243688 A1 | 8/2014 | Caron et al. | |
| 2014/0276933 A1 | 9/2014 | Hart et al. | |
| 2014/0276934 A1 | 9/2014 | Balaji et al. | |
| 2014/0276953 A1 * | 9/2014 | Swarup | B25J 18/007 |
| | | | 606/130 |
| 2015/0173837 A1 | 6/2015 | Barnett | |
| 2015/0265807 A1 | 9/2015 | Park et al. | |
| 2016/0279388 A1 | 9/2016 | Barrish et al. | |
| 2017/0021132 A1 | 1/2017 | Laby et al. | |
| 2017/0021143 A1 | 1/2017 | Barrish et al. | |
| 2017/0042408 A1 * | 2/2017 | Washburn | A61B 1/00096 |
| 2017/0157363 A1 | 6/2017 | Barrish et al. | |
| 2018/0071492 A1 | 3/2018 | Laby et al. | |
| 2018/0085559 A1 | 3/2018 | Laby et al. | |
| 2018/0200483 A1 | 7/2018 | Laby et al. | |

FOREIGN PATENT DOCUMENTS

| | | |
|---|---|---|
| WO | 2016160586 | 10/2016 |
| WO | 2016160587 | 10/2016 |
| WO | 2016160589 | 10/2016 |
| WO | 2017096388 | 6/2017 |

OTHER PUBLICATIONS

"A Tiny Spectrometer that Costs 10 Bucks", Qmed, Available online at http://www.qmed.com/mpmn/medtechpulse/tiny-spectrometer-costs-10-buckscid=nl.qmed02.20141216, Dec. 12, 2014, 3 pages.
"Accelerometer, Gyro and IMU Buying Guide", Available online at https://www.sparkfun.com/pages/accel_gyro_guide, 10 pages.
"Balloons and Balloon Catheters", Teleflex Incorporated, Available online at http://www.teleflexmedicaloem.com/diagnostic-and-interventional-catheters/balloon-catheters/, 2015, 3 pages.
"Compliant Robots", EUCog Wiki, Available online at http://www.eucognition.org/eucog-wiki/Compliant_robots, 2012, 5 pages.
"Convoluted Tubing to an Outer Diameter of 65 mm", ProfilePipe Machinery Inc., Available online at http://www.profilepipe.com/small_corrugators.html, 2015, 2 pages.
"CoreValve™ System", Medtronic, 2014, 61 pages.
"Corrugator Technologies: Overview and New Developments", Plastics, Corrugator technologies overview, Available at http://www.plastics.gl/extrusion-profile/corrugator-technologies-overview/, 2015, 8 pages.
"Corrugators and Pulsating Corrugators", Corma Inc., Available online at http://corma.com/products/corrugators-pulsating-corrugators/, 2011, 3 pages.
"Deflectable and Steerable Catheter Handbook", Creganna Tactx Medical, Terminology Guide & Design Options, Available online at http://www.creganna.com/wp-content/uploads/Steeringand-DeflectionTerminologyrev3.pdf, 7 pages.
"Edwards Tightens Transcatheter Valve Stranglehold", EP Vantage Ltd, Available online at http://www.epvantage.com/Universal/View.aspxtype=Story&id=580885&isEPVantage=yes, Jun. 18, 2015, 2 pages.
"How 3-D Printing Can Help Accelerate Fluidic Manifold Delivery", Qmed, Available online at http://www.qmed.com/mpmn/medtechpulse/how-3-d-printing-can-help-accelerate-fluidic-manifold-deliverycid=nl.qmed02.20150507, May 6, 2015, 3 pages.
"How Micro-Location Could Boost Healthcare IoT", Qmed, Electronic Components, Available online at http://www.qmed.com/mpmn/medtechpulse/how-micro-location-could-boost-healthcare-iotcid=nl.x.qmed02.edt.aud.qmed.20160606, Jun. 3, 2016, 2 pages.
"Introducing 3-D Injection Molding", Qmed, Available online at http://www.qmed.com/mpmn/gallery/image/4-introducing-3-d-injection-molding, 2014, 2 pages.
"LabSmith uProcess™ System", LabSmith, Inc., Microfluidic Automation, Available online at http://www.labsmith.com/products/LabSmith_uProcess_Brochure.pdf ga=1.142274551.472763250.1458083262., 2015, 6 pages.

(56) References Cited

OTHER PUBLICATIONS

"Microfluidics and Microfluidic Devices: A Review", Elveflow, Available online at http://www.elveflow.com/microfluidic-tutorials/microfluidic-reviews-and-tutorials/microfluidics-and-microfluidic-device-a-review/, 2015, 10 pages.
"Nanotube Yarns Twist Like Muscles", BBC News, Available online at http://www.bbc.co.uk/news/science-environment-15287185, Oct. 14, 2011, 8 pages.
"New 7 mm Electronic Valves", Clippard, Available online at http://www.clippard.com/products/electronic-valve-7mm, 2 pages.
"Overcoming Engineering Challenges: Developing a Tiny Robotically Steerable Guidewire", Qmed, Medtech Pulse Blog, Available online at http://www.qmed.com/mpmn/medtechpulse/overcoming-engineering-challenges-developing-tiny-robotically-steerable-guidewirecid=nl_qmed_daily, Feb. 15, 2013, 2 pages.
"Peripheral Dilatation Catheter Peripheral Dilatation System", Vascular solutions, PolarCath™ over-the-wire, Available online at www.vasc.com, pp. 1-12.
"Product Datasheet: silQflo™ Silicon Servo Valve", DMQ Inc., Available online at http://www.dmq-us.com/wp-content/uploads/2015/02/SSV-Datasheet-Rev-1.001.pdf, 2 pages.
"PTA Sphere-Curve", Tokai Medical Products Inc., Available online at http://www.tokaimedpro.co.jp/en/products/2009/000056.html, 2 pages.
"Researchers Comp1are Two-Year Clinical Outcomes of Mitral Valve Replacement and Repair in Treating Severe Valve Regurgitation", Mount Sinai Hospital, Icahn School of Medicine at Mount Sinai, Available online at http://www.mountsinai.org/about-us/newsroom/press-releases/researchers-compare-twoyear-clinical-outcomes-of-mitral-valve-replacement-and-repair-, Nov. 9, 2015, 2 pages.
"Scientific Tubing", SGE, Glass Lined Tubing (GLT™), Available online at www.sge.com, Fused Silica Tubing brochure PD-0230-Aw, 2001, 6 pages.
"Systematic Expertise Through Continuous Further Development", Festo AG & Co. KG, Bionic Handling Assistant, Available online at https://www.festo.com/net/supportportal/files/42050/brosch_fc_bha_3_0_en_lo.pdf, Apr. 2012, 6 pages.
"The Benefits of Using Bend Sensors", Sensor Products Inc., Available online at www.sensorprod.com, 2 pages.
"The Effect of Extrusion and Blow Molding Parameters on Angioplasty Balloon Production", MDDI, Medical Plastics and Biomaterials, Available online at http://www.mddionline.com/article/effect-extrusion-and-blow-molding-parameters-angioplasty-balloon-production, May 1, 1998, 4 pages.
"Tiny Artificial Muscles", Qmed, Available online at http://www.qmed.com/mpmn/gallery/image/1-tiny-artificial-muscles, 1 page.
"Tubing", SGE analytical science, 2011, 10 pages.
"U.S. Aortic Stenosis Disease Prevalence and Treatment Statistics", John Muir Health, Facts and Figures, Available Online at https://www.johnmuirhealth.com/services/cardiovascular-services/intervention/transcatheter-aortic-valve-replacement/facts-and-figures.html, 2016, 3 pages.
Arsalan et al., "Comparison of Current Costs and Reimbursement for Transcatheter and Surgical Aortic Valve Replacement", J. Am. Coll. Cardiol., vol. 67, Issue 13, ACC.i2 Interventional Cardiology, Available online at http://content.onlinejacc.org/article.aspxarticleid=2508037, Apr. 5, 2016, 2 pages.
Atzori et al., "Indoor navigation system using image and sensor data processing on a smartphone", Optimization of Electrical and Electronic Equipment (OPTIM), 2012 13th International Conference, Available online at https://www.researchgate.net/publication/261267019_Indoor_navigation_system_using_image_and_sensor_data_processing_on_a_smartphone, May 24-26, 2012, pp. 1158-1163.
Au et al., "Microvalves and Micropumps for BioMEMS", Micromachines, vol. 2, ISSN 2072-666X, Available online at www.mdpi.com/journal/micromachines, 2011, pp. 179-220.

Backer et al., "Percutaneous Transcatheter Mitral Valve Replacement", Circulation: Cardiovascular Interventions, Available online at http://circinterventions.ahajournals.org/content/7/3/400.full, 2014, pp. 400-409.
Bar-Cohen, "WorldWide ElectroActive Polymers", EAP (Artificial Muscles) Newsletter, vol. 16, No. 1, (The 31th issue), Available online at http://eap.jpl.nasa.gov, Jun. 2014, pp. 1-18.
Beahm et al., "Catheter Bonding Technology Overview", Avaialble online at www.beahmdesigns.com, Apr. 2012, 4 pages.
Biswal et al., "Development of an Active Catheter Mechanism Using IPMC for in Vivo Inspection", Journal of Mechatronics and Automation vol. 1, No. 1, Available online at: http://www.academia.edu/10757534/Development_of_an_Active_Catheter_Mechanism_using_IPMC_for_in_vivo_Inspection, 2014, 10 pages.
Bolling, "Can We Predict Mitral Valve Repair Rates by Individual Surgeons' Mitral Volume", Tex Heart Inst J., vol. 38, No. 6, 8th Current Trends in Aortic and Cardiothoracic Surgery, Available online at http://www.ncbi.nlm.nih.gov/pmc/articles/PMC3233323/, 2011, pp. 703-704.
Buntz, "Forget IoT: The Internet of Moving Things Is Where It Is At", Qmed, Available online at http://www.qmed.com/mpmn/medtechpulse/forget-iot-internet-moving-things-where-it, Dec. 10, 2014, 3 pages.
Buntz, "Graphene Breakthrough Could Be a Boon to Flexible Electronics", Electronic Components, Qmed, Available online at http://www.qmed.com/mpmn/medtechpulse/graphene-breakthrough-could-be-boon-fiexible-electronicscid=nl.qmed02, Nov. 14, 2013, 1 page.
Buntz, "How Tiny Artificial Muscles Could Be Huge Energy Savers", Motion Control, Qmed, Available online at http://www.qmed.com/mpmn/medtechpulse/how-tiny-artificial-muscles-could-be-huge-energy-saverscid=nl.qmed02.20150223, Feb. 20, 2015, 3 pages.
Buntz, "Using a T-Shirt Printer to Make Medical Circuits", Qmed, Electronic Components, Available online at http://www.qmed.com/mpmn/medtechpulse/using-t-shirt-printer-make-medical-circuits, Nov. 17, 2014, 3 pages.
Catherine et al., "Comparative Review of Endoscopic Devices Articulations Technologies Developed for Minimally Invasive Medical Procedures", Applied Bionics and Biomechanics, vol. 8, 2011, pp. 151-171.
Chakraborty et al., "Mems Micro-Valve for Space Applications", Sensors and Actuators A: Physical, vol. 83, No. 1-3, 2000, pp. 188-193.
Chandgadkar, "An Indoor Navigation System for Smartphones", Available online at http://www.doc.ic.ac.uk/teaching/distinguished-projects/2013/a.chandgadkar.pdf, Jun. 18, 2013, 80 pages.
Chang et al., "Electrostatically-Actuated Reconfigurable Elastomer Microfluidics", Available online at http://people.eecs.berkeley.edu/~maharbiz/HH_paper_mpchang_0008.pdf, 4 pages.
Chen et al., "High-Pressure On-Chip Mechanical Valves for Thermoplastic Microfluidic Devices", The Royal Society of Chemistry, Lab Chip, vol. 9, 2009, pp. 3511-3516.
Conrad et al., "Closed Loop Task Space Control of an Interleaved Continuum-Rigid Manipulator", IEEE International Conference on Robotics and Automation, Available online at http://robotics.engr.wisc.edu/cgi-bin/wikiwp/category/continuum-robotics/, 2015, 8 pages.
Coyne, "Comprehensive Manufacturing of Microfluidic Diagnostic Devices", IVD, MDDI Medical Device and Diagnostic Industry, Jun. 17, 2014, 4 pages.
Dabove et al., "Inertial Sensors for Smartphones Navigation", SpringerPlus, vol. 4, No. 834, Available online at http://www.ncbi.nlm.nih.gov/pmc/articles/PMC4695469/, 2015, 18 pages.
D'Arcy et al., "Valvular Heart Disease: The Next Cardiac Epidemic", vol. 97, Issue 2, Available online at http://heart.bmj.com/content/97/2/91.extract, 2011, pp. 91-93.
De Sars et al., "A Practical Approach to the Design and Control of Active Endoscopes", Mechatronics, vol. 20, Available online at http://www.elsevierscitech.com/pdfs/Mechatronics_DeSars.pdf, 2010, pp. 251-264.
Don et al., "Novel Velocity Model to Improve Indoor Localization Using Inertial Navigation With Sensors on a Smart Phone", Avaialble online at http://arxiv.org/pdf/1601.03004.pdf, Jan. 12, 2016, 5 pages.

(56) References Cited

OTHER PUBLICATIONS

Dupont et al., "Snakes, Worms and Catheters: Continuum and Serpentine Robots for Minimally Invasive Surgery", IEEE ICRA Full Day Workshop, May 3, 2010, 60 pages.
Eitel, "The Rise of Soft Robots and the Actuators That Drive Them", Available online at http://machinedesign.com/robotics/rise-soft-robots-and-actuators-drive-them, Sep. 12, 2013, 7 pages.
Fedak et al., "Evolving Concepts and Technologies in Mitral Valve Repair", American Heart Association, Inc., Contemporary Reviews in Cardiovascular Medicine, vol. 117, Issue 7, Available online at http://circ.ahajournals.org/content/117/7/963.full, Feb. 19, 2008, pp. 963-974.
Fite et al., "A Gas-Actuated Anthropomorphic Prosthesis for Transhumeral Amputees", IEEE Transactions on Robotics, vol. 24, No. 1, Feb. 2008, pp. 159-169.
Fornell, "Transcatheter Mitral Valve Replacement Devices in Development", Diagnostic and Interventional Cardiology, Available online at http://www.dicardiology.com/article/transcatheter-mitral-valve-replacement-devices-development, Dec. 30, 2014, 5 pages.
Fu et al., "Research on the Axis Shape of an Active Catheter", Int. J. Med. Robot.;vol. 4, No. 1, Mar. 2008, pp. 69-76.
Fu et al., "Steerable Catheters in Minimally Invasive Vascular Surgery", Int. J. Med. Robot., vol. 5, No. 4, Dec. 2009, pp. 381-391.
Gionata et al., "An Inertial and Qr Code Landmarks-Based Navigation System for Impaired Wheelchair Users", Available online at https://www.researchgate.net/publication/261551014_An_inertial_and_QR_code_landmarks-based_navigation_system_for_impaired_wheelchair_users, May 29, 2014, pp. 205-214.
Grube, "Development of a TMVR Device Challenge to Innovators", ICI meeting, Dec. 13-15, 2015, 30 pages.
Haga et al., "Active Bending Catheter and Endoscope Using Shape Memory Alloy Actuators", Available online at www.intechopen.com, Shape Memory Alloys, 2010, 21 pages.
Haga et al., "Multi-Functional Active Catheter", Available online at http://bdml.stanford.edu/twiki/pub/Haptics/DesignReferencesSummer2009/MultifunctionalActiveCatheter.pdf, pp. 147-186.
Herrmann et al., "Novel Transcatheter Approaches", Heart Valve Summit, American association of Thoracic surgery, Available online at http://aats.org/multimedia/files/valve/2015/Presentations/Thursday/600-Herrmann.pdf, 2015, 26 pages.
Ikeuchi et al., "Development of Pressure-Driven Micro Active Catheter using Membrane Micro Emboss Following Excimer Laser Ablation (MeME-X) Process", IEEE International Conference on Robotics and Automation, Available online at http://ir.nul.nagoya-u.ac.jp/jspui/bitstream/2237/13924/1/ICRA09_MeMEX.pdf, May 12-17, 2009, pp. 4469-4472.
Jagadeesan, "Design and Control of an Active Catheter", Available online at http://scholar.harvard.edu/jayender/activecatheter, 2 pages.
Jia et al., "Online Camera-Gyroscope Auto-Calibration for Cell-phones", IEEE Transactions on Image Processing, Available online at http://users.ece.utexas.edu/~bevans/papers/2015/autocalibration/autocalibrationIEEETransImageProcPaperDraft.pdf, 2013, 11 pages.
Johnson, "Modeling of Frictional Gas Flow in a Piezoelectrically Actuated High-pressure Microvalve for Flowrate Control", Dec. 16, 2005, 197 pages.
Jung et al., "A Modeling Approach for Continuum Robotic Manipulators: Effects of Nonlinear Internal Device Friction", IEEE/RSJ International Conference on Intelligent Robots and Systems, Sep. 25-30, 2011, pp. 5139-5146.
Kasahara et al., "Surface Modification of Polyethylene Terephthalate (PET) by 172-nm Excimer lamp", Technical paper, 2012, pp. 47-54.
Kato et al., "An Inchworm Type In-Pipe Mobile Microrobot Driven by Three Gas-liquid Phase-change Actuators", Proceedings of the Annual Meeting—American Society for Precision Engineering, 2003, pp. 295-298.
Kim et al., "Materials for Multifunctional Balloon Catheters With Capabilities in Cardiac Electrophysiological Mapping and Ablation Therapy", Nat Mater., vol. 10, No. 4, Available online at http://www.ncbi.nlm.nih.gov/pmc/articles/PMC3132573/, Apr. 2011, pp. 316-323.

Kirby et al., "Microfluidic Routing of Aqueous and Organic Flows at High Pressures: Fabrication and Characterization of Integrated Polymer Microvalve Elements", The Royal Society of Chemistry, Lab Chip, vol. 5, 2005, pp. 184-190.
Korane, "Robot Imitates an Elephant's Trunk", Available online at http://machinedesign.com/robotics/robot-imitates-elephant-s-trunk, Sep. 13, 2010, 5 pages.
Langelaar et al., "Modeling of a Shape Memory Alloy Active Catheter", 45th AIAA/ASME/ASCE/AHS/ASC Structures, Structural Dynamics & Materials Conference, American Institute of Aeronautics and Astronautics, Available online at http://citeseerx.ist.psu.edu/viewdoc/downloaddoi=10.1.1.125.1080&rep=rep1&type=pdf, Apr. 1922, 2004, 16 pages.
Lee et al., "Fabrication, Characterization, and Computational Modeling of a Piezoelectrically Actuated Microvalve for Liquid Flow Control", Journal of Microelectromechanical Systems, vol. 15, No. 3, IEEE, Jun. 2006, pp. 686-696.
Levy, "Tiny Ultrasound Camera Images Blood Vessel Interior in 3-D", Medical Imaging, Qmed, Available online at http://www.qmed.com/mpmn/medtechpulse/tiny-ultrasound-camera-images-blood-vessel-interior-3-dcid=nl.qmed02, Mar. 3, 2014, 5 pages.
Maglione et al., "Ultra-High-Pressure Balloon Angioplasty for Treatment of Resistant Stenoses Within or Adjacent to Previously Implanted Pulmonary Arterial Stents", Circulation: Cardiovascular Interventions, Available online at http://circinterventions.ahajournals.org/content/2/1/52.full, 2009, pp. 52-58.
Malek et al., "Femtosecond laser machining and lamination for large-area flexible organic microfluidic chips", European Physical Journal: Applied Physics, EDP Sciences, Available online at https://hal.archives-ouvertes.fr/hal-00480155/document, Apr. 2009, 8 pages.
Mazzarese, "Low-Profile Balloon Catheters are Critical to TAVR's Success", Medical Tubing Types by MDDI Staff, Available online at http://www.mddionline.com/article/low-profile-balloon-catheters-are-critical-tavr-success-10-21-2014cid=nl.mddi01.20141023, Oct. 21, 2014, 3 pages.
Messenger, "A Comprehensive Guide to the U.S. TAVR Market: Surveying the Field", Available online at http://www.meddeviceonline.com/doc/a-comprehensive-guide-to-the-u-s-tavr-market-surveying-the-field-0001, Apr. 12, 2016, 7 pages.
Mohty et al., "Valvular Heart Disease in Elderly Adults", Available online at http://www.uptodate.com/contents/valvular-heart-disease-in-elderly-adults, 2016, 6 pages.
Mueller et al., "An Overview of Mems-based Micropropulsion Developments at JPL", Acta Astronautica, vol. 52, Issues 9-12, Selected Proceedings of the 3rd IAA International Symposium on Small Satellites for Earth Observation, May-Jun. 2003, 15 pages.
Mueller et al., "Design and Fabrication of MEMS-Based Micropropulsion Devices at JPL", Proceedings of SPIE vol. 4558, 2001, pp. 57-71.
Muller et al., "Remote Control Catheter Navigation: Options for Guidance Under MRI", Journal of Cardiovascular Magnetic Resonance, vol. 14, No. 33, Available online at http://www.jcmr-online.com/content/14/1/33, 2012, pp. 1-9.
Newmarker, "How Lasers Are Changing MedTech", Lasers, Qmed, Available online at http://www.qmed.com/mpmn/medtechpulse/how-lasers-are-changing-medtechcid=nl.qmed02, Jan. 14, 2014, 3 pages.
Newmarker, "How Scotch Tape is Driving Diagnostics Breakthroughs", Medical Plastics, Qmed, Available online at http://www.qmed.com/mpmn/medtechpulse/how-scotch-tape-driving-diagnostics-breakthroughscid=nl.qmed02.20141002, Oct. 1, 2014, 3 pages.
Nolker et al., "Differences in Tissue Injury and Ablation Outcomes in Atrial Fibrillation Patients—Manual versus Robotic Catheters", Journal of Atrial Fibrillation, Department of Cardiology, Heart and Diabetes Center, vol. 6, No. 2, Aug.-Sep. 2013, pp. 82-88.
Oh et al., "A Review of Microvalves", Topical Review, Journal of Micromechanics and Microengineering, vol. 16, 2006, pp. R13-R39.
Ono et al., "Development of a Cylinder Type Gas-liquid Phase-change Actuator", 2 pages.
Parmar, "FDA Approves St. Jude Medical's Force-Sensing Ablation Catheters for AF", Regulatory and Compliance, MDDI Medical Device and Diagnostic Industry, Available online at http://www.

(56) References Cited

OTHER PUBLICATIONS mddionline.com/article/fda-approves-st-jude-medicals-force-sensing-ablation-catheters-af-102714cid=nl.mddi01.20141028, Oct. 27, 2014, 3 pages.
Penning et al., "A Combined Modal-Joint Space Control Approach for Minimally Invasive Surgical Continuum Manipulators", Advanced Robotics, vol. 28, No. 16, Jul. 2014, 41 pages.
Penning et al., "An Evaluation of Closed-Loop Control Options for Continuum Manipulators", IEEE, 2012, 6 pages.
Penning, "ICRA 2012 Recap", Available online at http://robotics.engr.wisc.edu/cgi-bin/wikiwp/2012/11/icra-2012-recap/, Nov. 11, 2012, 2 pages.
Penning et al., "Towards Closed Loop Control of a Continuum Robotic Manipulator for Medical Applications", IEEE, 2011, 6 pages.
Pollock, "Bionic Ants Could Be Tomorrow's Factory Workers", Available online at http://www.reuters.com/article/2015/03/30/us-germany-bionic-ants-idUSKBN0MQ1WD20150330, Mar. 30, 2015, 3 pages.
Preston-Maher et al., "A Technical Review of Minimally Invasive Mitral Valve Replacements", Cardiovascular Engineering and Technology, vol. 6, No. 2, Jun. 2015, pp. 174-184.
Quero et al., "A Novel Pressure Balanced Microfluidic Valve", Proc. ISCAS, IEEE, 2002, pp. 1-4.
Rich et al., "Costs for Mitral Valve Surgery According to STS Preoperative Risk: Implications for Transcatheter Mitral Therapies", American Association for Thoracic Surgery, Available Online at http://aats.org/mitral/abstracts/2015/P165.cgi, 2016, 2 pages.
Roriz et al., "Fiber Optic Intensity-Modulated Sensors: A Review in Biomechanics", Photonic Sensors, vol. 2, No. 4, 2012, pp. 315-330.
Rossiter et al., "Printing 3D Dielectric Elastomer Actuators for Soft Robotics", SPIE Proceedings, vol. 7287, Apr. 6, 2009, 2 pages.
Schut, "Corrugator Vacuum Forming", Plastics Technology, Available online at http://www.ptonline.com/articles/'corrugator-vacuum-forming', Jul. 2005, 4 pages.
Shoa et al., "Conducting Polymer Based Active Catheter for Minimally Invasive Interventions inside Arteries", Conf Proc IEEE Eng Med Biol Soc, Available online at http://mm.ece.ubc.ca/mediawiki/images/b/b7/PID616280.pdf, 2008, pp. 2063-2066.
Strickland, "Inside an MRI, a Non-Metallic Robot Performs Prostate Surgery", Available online at http://spectrum.ieee.org/automaton/robotics/medical-robots/inside-an-mri-a-nonmetallic-robot-performs-prostate-surgery, Jul. 8, 2015, 3 pages.
Takizawa et al., "Development of a Microfine Active Bending Catheter Equipped With MIF Tactile Sensors", Available online at http://www.ics.forth.gr/bioloch/internal/papers/Olympus.pdf, 1999, 7 pages.
Taramasso et al., "Current Challenges in Interventional Mitral Valve Treatment", J. Thorac. Dis., vol. 7, No. 9, Available online at http://www.ncbi.nlm.nih.gov/pmc/articles/PMC4598533/, 2015, pp. 1536-1542.
Temiz et al., "Lab-on-a-Chip Devices: How to Close and Plug the Lab", Microelectronic Engineering, vol. 132, 2015, pp. 156-175.
Tung et al., "Laser-Machined Shape Memory Alloy Actuators for Active Catheters", Mechatronics, IEEE/ASME Transactions on, vol. 12, No. 4, Aug. 2007, pp. 439-446.
Van Oosten et al., "Printed Artificial Cilia From Liquid-crystal Network Actuators Modularly Driven by Light", Nature Materials, vol. 8, Available online at http://www.nature.com/nmat/journal/v8/n8/full/nmat2487.html, 2009, pp. 677-682.
Veeramani, "A Transformative Tool for Minimally Invasive Procedures: Design, Modeling and Real-time Control of a Polycrystalline Shape Memory Alloy Actuated Robotic Catheter", 2009, 198 pages.
Walters, "Gas-Flow Calculations: Don't Choke", Applied Flow Technology, Chemical Engineering, Available online at http://www.aft.com/documents/AFT-CE-Gasflow-Reprint.pdf, Jan. 2000, 8 pages.
Wasserman, "Edwards and Medtronic Turn up TAVR Competition With Positive Study Data", Available online at http://www.fiercemedicaldevices.com/story/edwards-and-medtronic-turn-tavr-competition-positive-study-data/2015-03-16, Mar. 16, 2015, 3 pages.
Webb et al., "Transcatheter Aortic Valve Implantation: The Evolution of Prostheses, Delivery Systems and Approaches", Archives of Cardiovascular Disease, vol. 105, 2012, pp. 153-159.
Weber et al., "Side-Selective Atrial Transseptal Laser Puncture", The Journal of Innovations in Cardiac Rhythm Management, vol. 4, Avaiable online at http://www.innovationsincrm.com/cardiac-rhythm-management/2013/december/524-side-selective-atrial-transseptal-laser-puncture, Dec. 2013, pp. 1481-1485.
Wirtl et al., "White Paper Piezo Technology in Pneumatic Valves", Festo AG & Co. KG, 2014, pp. 1-9.
Wood, "Early Results for Transcatheter Mitral Valve Replacement Reveal Complications and Challenges for the Long Road Ahead", Available online at http://www.tctmd.com/show.aspxid=133937, Feb. 22, 2016, 1 pages.
Wutzler et al., "Robotic Ablation of Atrial Fibrillation", Department of Cardiology, . Vis. Exp. (99), e52560, Available online at http://www.jove.com/video/52560/robotic-ablation-of-atrial-fibrillation, 2015, 14 pages.
Yang et al., "Leak-Tight Piezoelectric Microvalve for High-Pressure Gas Micropropulsion", Journal of Microelectromechanical Systems, vol. 13, No. 5, IEEE, Available Online at http://web.stevens.edu/ses/documents/fileadmin/documents/pdf/JMEMS_hp_valve.pdf, Oct. 2004, pp. 799-807.
Yarbasi et al., "On the Design of a Continuum Robot with Extendable Balloons", Department of Mechanical Engineering, 2015, 1 page.
You et al., "A Doubly Cross-Linked Nano-Adhesive for the Reliable Sealing of Flexible Microfluidic Devices", Lab Chip, vol. 13, No. 7, Available online at http://www.ncbi.nlm.nih.gov/pubmed/23381132, Apr. 2013, pp. 1266-1272.

* cited by examiner

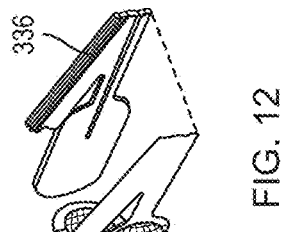
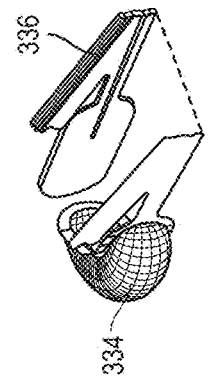
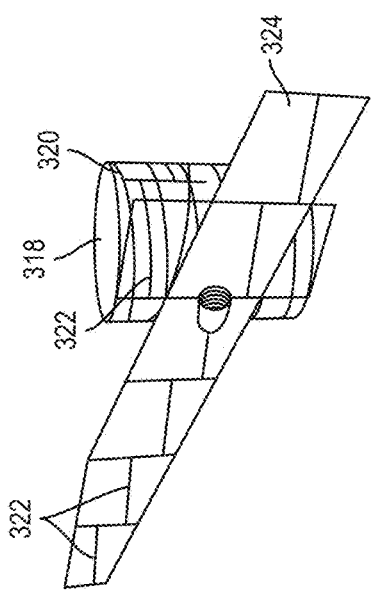
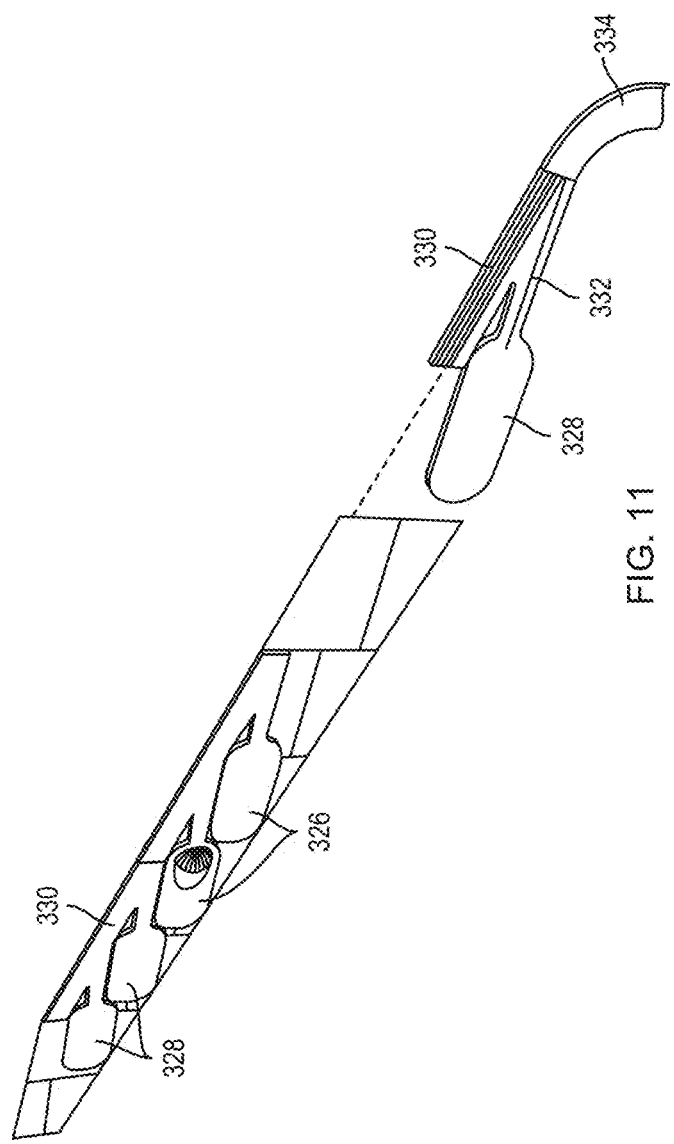

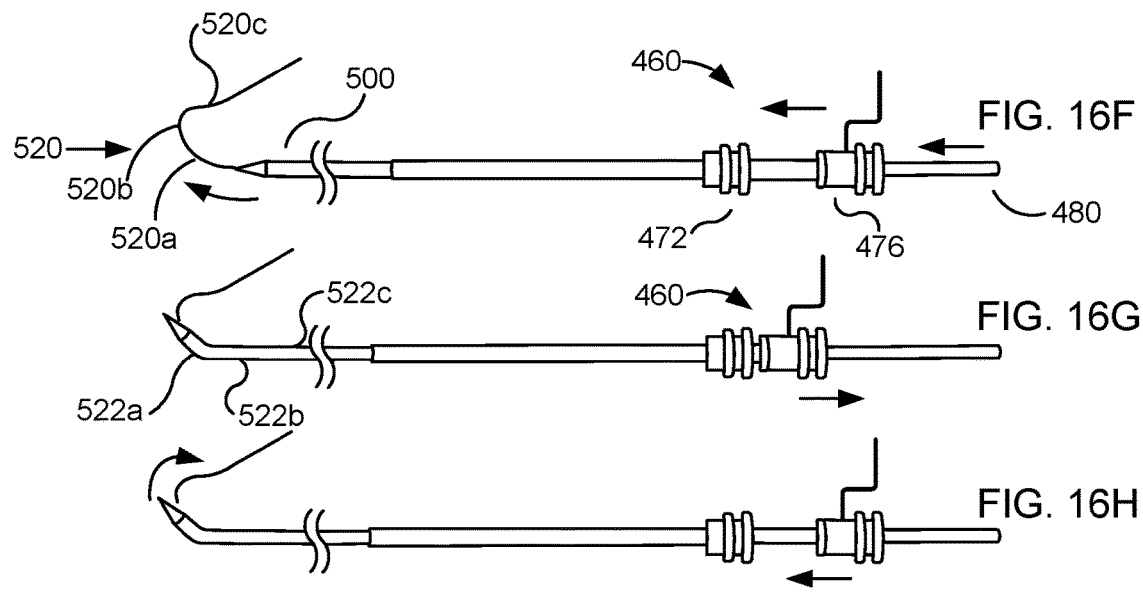
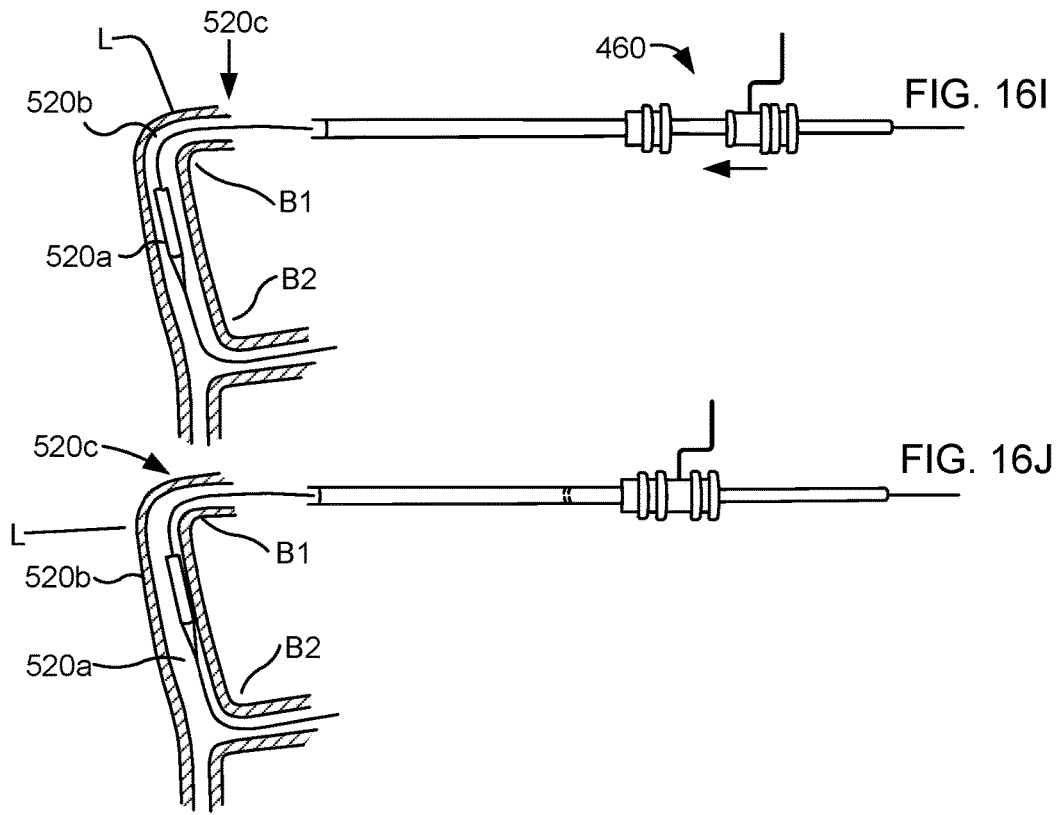

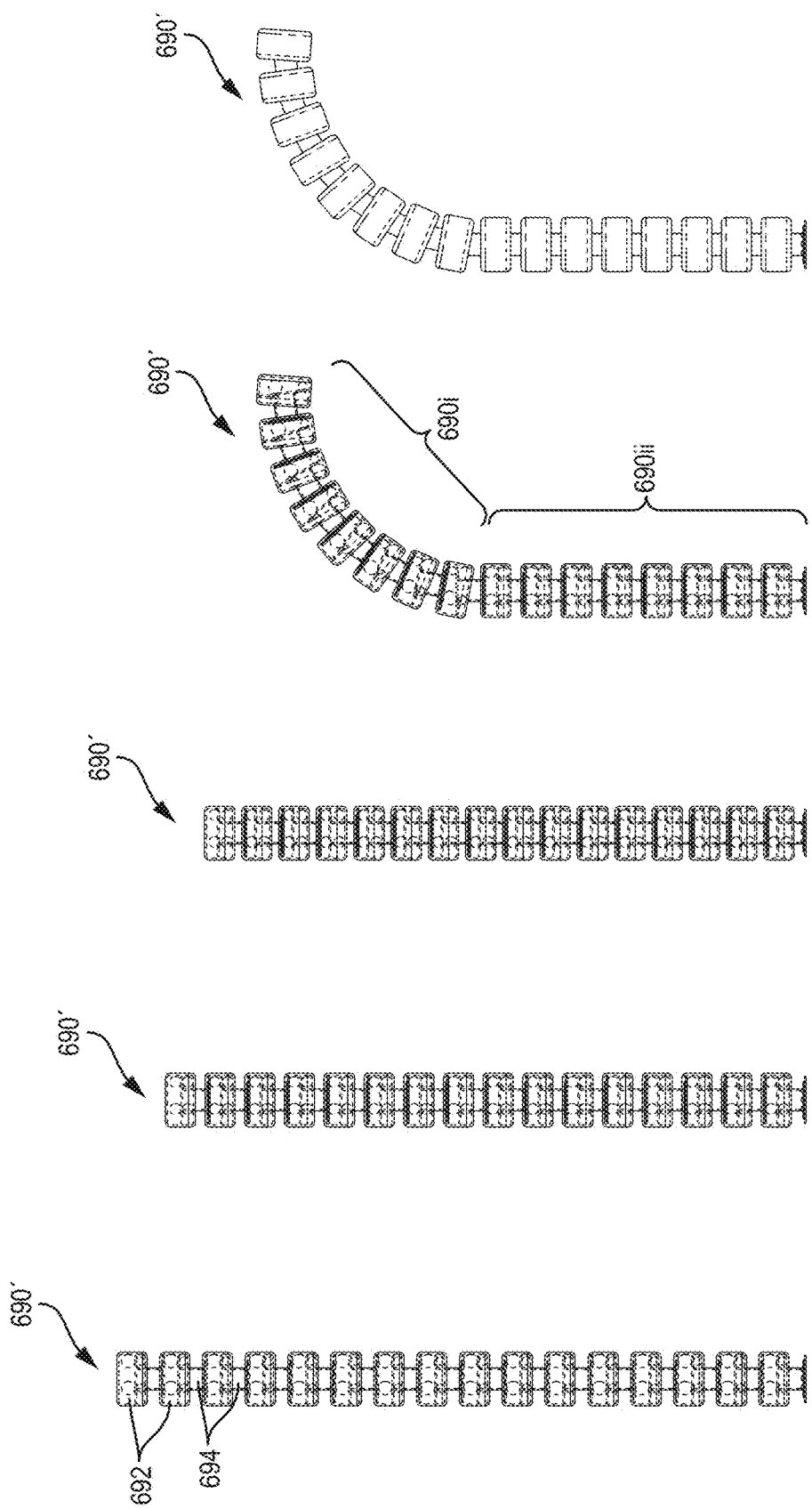

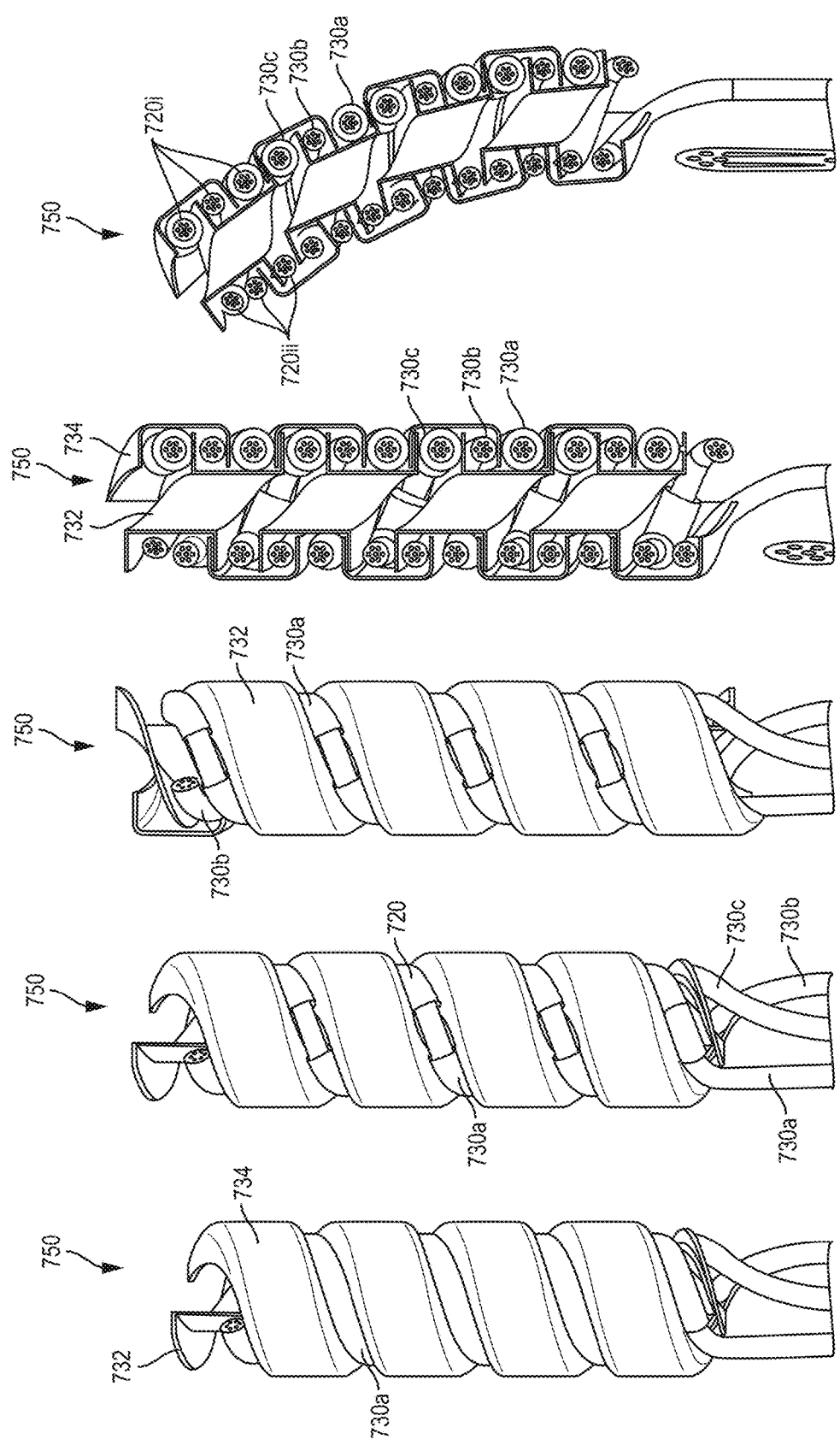

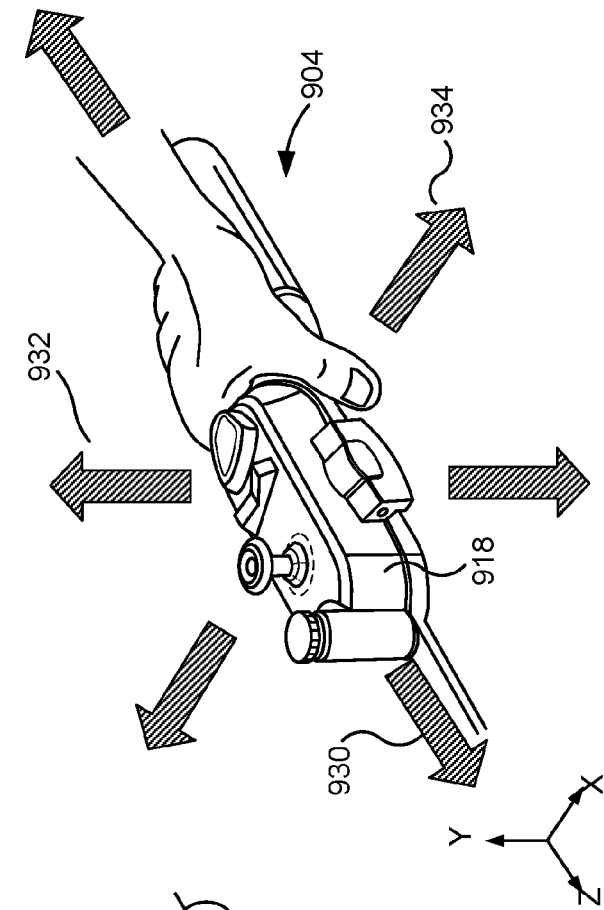
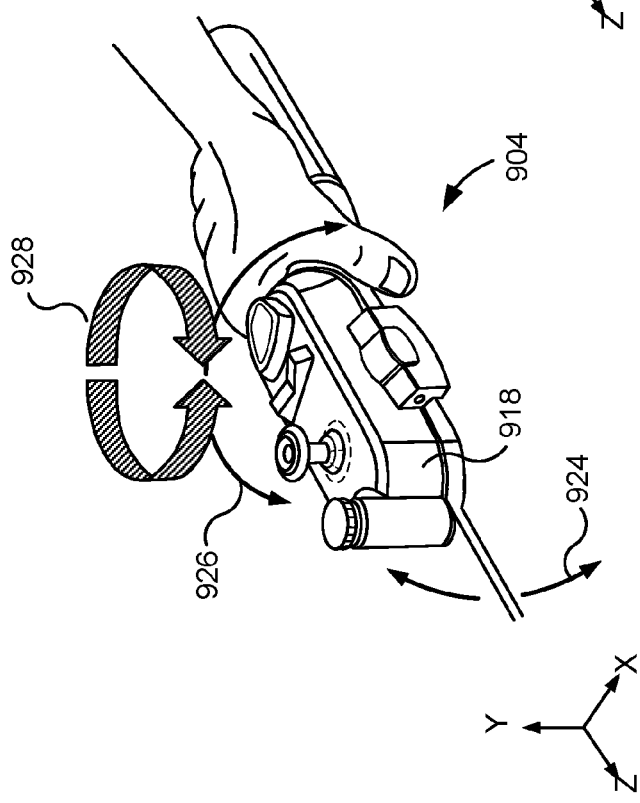

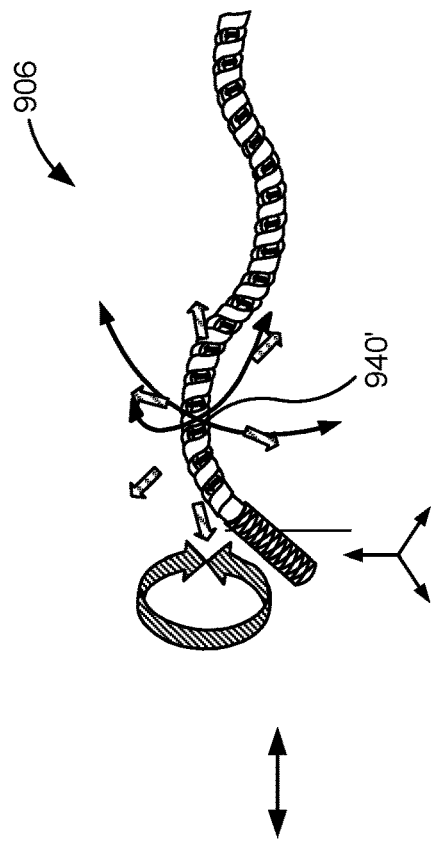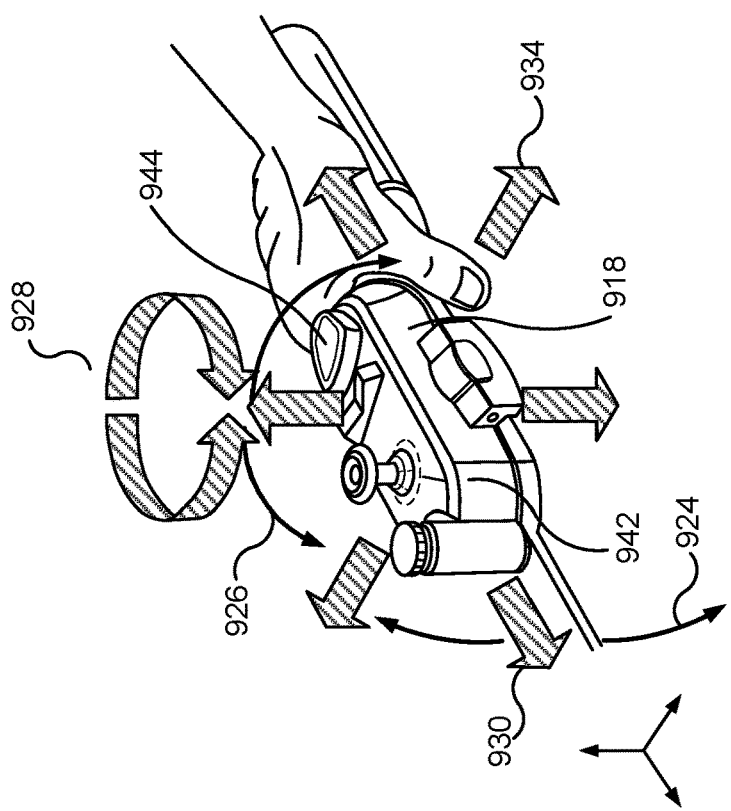
FIG. 35D

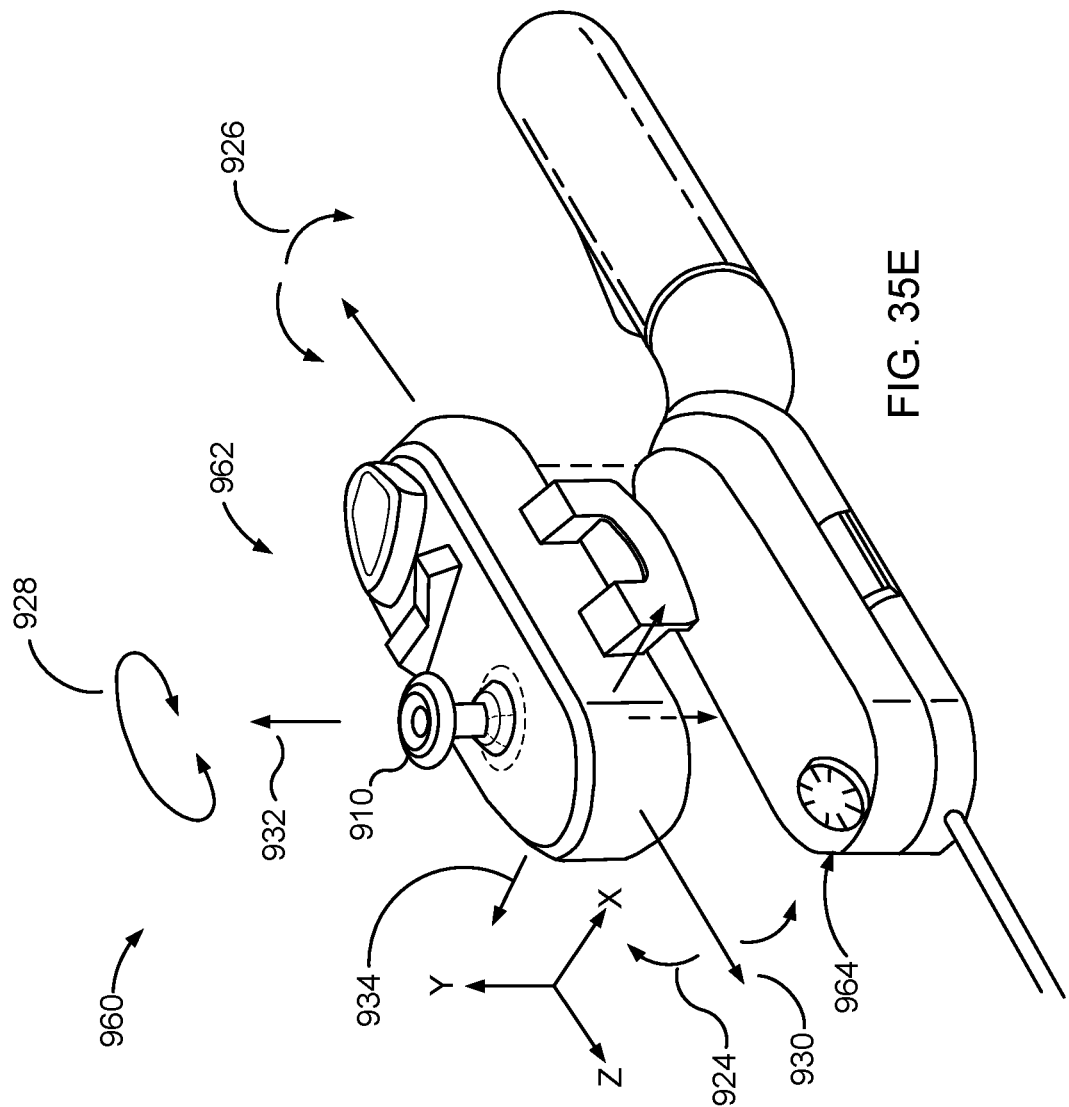

INPUT AND ARTICULATION SYSTEM FOR CATHETERS AND OTHER USES

CROSS REFERENCE TO RELATED APPLICATIONS

The present application claims the benefit of priority from co-assigned U.S. Provisional Patent App. Nos. 62/263,231 filed Dec. 4, 2015, entitled "Input and Articulation System for Catheters and Other Uses"; and 62/326,551 filed Apr. 22, 2016, entitled "Input and Articulation System for Catheters and Other Uses"; the full disclosures of which are incorporated herein by reference in their entirety The subject matter of the present application is also generally related to that of U.S. patent application Ser. No. 15/081,026 filed Mar. 25, 2016, entitled "Articulation System, Devices, and Methods for Catheters and Other Uses"; the full disclosure of which is incorporated herein by reference in its entirety.

FIELD OF THE INVENTION

In general, the present invention provides improved medical devices, systems, and methods, including improved input structures, systems, and methods for selectively bending of, altering the bend characteristics of, and/or altering the lengths of catheter bodies, guidewires, and the like. The invention is particularly well suited for catheter systems that involve both manual manipulation of the catheter and powered articulation of the catheter within a patient, and may facilitate procedures that include alternating between the two. The invention may be included in or be used with articulation structures, systems, and methods for articulation, in exemplary embodiments with systems having a fluid-driven balloon array that can help shape, steer or advance a catheter, guidewire, or other elongate flexible structure extending along a body lumen.

BACKGROUND OF THE INVENTION

Diagnosing and treating disease often involve accessing internal tissues of the human body. Once the tissues have been accessed, medical technology offers a wide range of diagnostic tools to evaluate tissues and identify lesions or disease states. Similarly, a number of therapeutic tools have been developed that can help surgeons interact with, remodel, deliver drugs to, or remove tissues associated with a disease state so as to improve the health and quality of life of the patient. Unfortunately, gaining access to and aligning tools with the appropriate internal tissues for evaluation or treatment can represent a significant challenge to the physician, can cause serious pain to the patient, and may (at least in the near term) be seriously detrimental to the patient's health.

Open surgery is often the most straightforward approach for gaining access to internal tissues. Open surgery can provide such access by incising and displacing overlying tissues so as to allow the surgeon to manually interact with the target internal tissue structures of the body. This standard approach often makes use of simple, hand-held tools such as scalpels, clamps, sutures, and the like. Open surgery remains, for many conditions, a preferred approach. Although open surgical techniques have been highly successful, they can impose significant trauma to collateral tissues, with much of that trauma being associated with gaining access to the tissues to be treated.

To help avoid the trauma associated with open surgery, a number of minimally invasive surgical access and treatment technologies have been developed. Many minimally invasive techniques involve accessing the vasculature, often through the skin of the thigh, neck, or arm. One or more elongate flexible catheter structures can then be advanced along the network of blood vessel lumens extending throughout the body and its organs. While generally limiting trauma to the patient, catheter-based endoluminal therapies are often reliant on a number of specialized catheter manipulation techniques to safely and accurately gain access to a target region, to position a particular catheter-based tool in alignment with a particular target tissue, and/or to activate or use the tool. In fact, some endoluminal techniques that are relatively simple in concept can be very challenging (or even impossible) in practice (depending on the anatomy of a particular patient and the skill of a particular physician). More specifically, advancing a flexible guidewire and/or catheter through a tortuously branched network of body lumens might be compared to pushing a rope. As the flexible elongate body advances around first one curve and then another, and through a series of branch intersections, the catheter/tissue forces, resilient energy storage (by the tissue and the elongate body), and movement interactions may become more complex and unpredictable, and control over the rotational and axial position of the distal end of a catheter can become more challenging and less precise. Hence, accurately aligning these elongate flexible devices with the desired luminal pathway and target tissues can be a significant challenge.

A variety of mechanisms can be employed to steer or variably alter deflection of a tip of a guidewire or catheter in one or more lateral directions to facilitate endoluminal and other minimally invasive techniques. Pull wires may be the most common catheter tip deflection structures and work well for many catheter systems by, for example, controllably decreasing separation between loops along one side of a helical coil, braid, or cut hypotube near the end of a catheter or wire. It is often desirable to provide positive deflection in opposed directions (generally by including opposed pull wires), and in many cases along two orthogonal lateral axes (so that three or four pull wires are included in some devices). Where additional steering capabilities are desired in a single device, still more pull wires may be included. Complex and specialized catheter systems having dozens of pull wires have been proposed and built, in some cases with each pull wire being articulated by a dedicated motor attached to the proximal end. Alternative articulation systems have also been proposed, including electrically actuated shape memory alloy structures, piezoelectric actuation, phase change actuation, and the like. As the capabilities of steerable systems increase, the range of therapies that can use these technologies should continue to expand.

Unfortunately, as articulation systems for catheters get more complex, it can be more and more challenging to maintain accurate control over these flexible bodies. For example, pull wires that pass through bent flexible catheters often slide around the bends over surfaces within the catheter, with the sliding interaction extending around not only bends intentionally commanded by the user, but also around bends that are imposed by the tissues surrounding the catheter. Hysteresis and friction of a pull-wire system may vary significantly with that sliding interaction and with different overall configurations of the bends, so that the articulation system response may be difficult to predict and control. Furthermore, more complex pull wire systems may add additional challenges. While opposed pull-wires can each be used to bend a catheter in opposite directions from a generally straight configuration, attempts to use both together—while tissues along the segment are applying unknown forces in unknown directions—may lead to widely inconsistent results. Hence, there could be benefits to providing more accurate small and precise motions, to improving the lag time, and/or to providing improved transmission of motion over known catheter pull-wire systems so as to avoid compromising the coordination, as experienced by the surgeon, between the input and output of catheters and other elongate flexible tools.

Along with catheter-based therapies, a number of additional minimally invasive surgical technologies have been developed to help treat internal tissues while avoiding at least some of the trauma associated with open surgery. Among the most impressive of these technologies is robotic surgery. Robotic surgeries often involve inserting one end of an elongate rigid shaft into a patient, and moving the other end with a computer-controlled robotic linkage so that the shaft pivots about a minimally invasive aperture. Surgical tools can be mounted on the distal ends of the shafts so that they move within the body, and the surgeon can remotely position and manipulate these tools by moving input devices with reference to an image captured by a camera from within the same workspace, thereby allowing precisely scaled micro-surgery. Alternative robotic systems have also been proposed for manipulation of the proximal end of flexible catheter bodies from outside the patient so as to position distal treatment tools. These attempts to provide automated catheter control have met with challenges, which may be in-part because of the difficulties in providing accurate control at the distal end of a flexible elongate body using pull-wires extending along bending body lumens. Still further alternative catheter control systems apply large magnetic fields using coils outside the patient's body to direct catheters inside the heart of the patient, and more recent proposals seek to combine magnetic and robotic catheter control techniques. In addition to the technical challenges of (and large capital equipment investments involved in) known robotic manipulators and catheter articulation systems, the user interface of these systems are often large, complex, expensive, and/or configured to be used by a physician seated outside the sterile field. While the potential improvements to control surgical accuracy make all of these efforts alluring, the capital total equipment costs and overall burden to the healthcare system of these large, specialized systems is a concern.

In light of the above, it would be beneficial to provide improved medical devices, systems, and methods, including improved input devices, articulation systems, and methods for users to direct and control articulation of flexible medical structures such as catheters, guidewires, and the like. Improved techniques for controlling the flexibility of elongate structures (articulated or non-articulated) would also be beneficial. It would be particularly beneficial if these new technologies were suitable to provide or enhance therapeutically effective control over movement of a distal end of a flexible guidewire, catheter, or other elongate body extending into a patient body. It would also be beneficial if these new techniques would allow enhanced ease of use of automated elongate flexible medical devices, ideally so as to facilitate safe and effective use of powered articulation systems to access target regions within a patient body, or to achieve a desired alignment of a therapeutic or diagnostic tool with a target tissue. It would also be helpful if these techniques could help provide enhanced control over movements of a guidewire or catheter using a combination of manual manipulation with powered articulations, with the manual manipulation and powered articulations occurring sequentially, concurrently, or a combination of both.

BRIEF SUMMARY OF THE INVENTION

The present invention generally provides new medical devices, systems, and methods, with exemplary embodiments providing improved input structures, systems, and methods that can be used for selectively bending of, altering the bend characteristics of, and/or altering the lengths of catheter bodies, guidewires, steerable trocars, and other flexible structures inserted into a patient during use. A sensor can be coupled to an elongate flexible body that extends from adjacent a minimally invasive access site into a patient during use. The sensor can transmit signals associated with flexing of the body outside of the patient. An articulatable distal portion of the inserted structure has bend characteristics that can be altered in response to the sensor signals, and a processor may operatively couple the distal portion with the sensor so that the manual flexing of the body outside of the patient can be used to control articulation of the distal portion within the patient in a powered articulation mode. The flexible structure may extend proximally from the distal portion toward (and in some embodiments through) the body, and the system may have a manual mode relying on manual manipulation of the flexible structure proximally of the body. Many embodiments may sense axial movement of the flexible structure in or out of an introducer sheath (or other access site), and associated signals can be used to locally alter bend characteristics along one or more desired axial segments of the flexible structure within the patient. Still further embodiments may use input signals to locally alter pushability or trackability along an elongate flexible structure. Regardless, many of the embodiments described herein facilitate control over movements of a guidewire or catheter through a combination of manual manipulation and powered articulations, with the manual movements and powered articulations optionally occurring sequentially, concurrently, or a combination of both.

In a first aspect, the invention provides a catheter articulation system for use by a user having a hand. The catheter articulation system comprises an elongate catheter body having a proximal portion and a distal portion with an axis therebetween. The distal portion of the catheter body is configured for insertion into a patient through an aperture. A plurality of actuators is operatively coupled with the distal portion of the catheter body. A housing is coupleable (optionally wirelessly) with the proximal portion of the catheter body and configured to be supported with the hand of the user. A sensor system can be mounted to the housing, the sensor system comprising an accelerometer and/or a gyroscope and configured to measure movement of the housing in a plurality of degrees of freedom so as to receive a movement command from the hand supporting the housing. A processor may couple the sensor to the actuators so that the distal portion of the catheter body moves in response to the movement command.

As general optional features, the housing may contain a battery and be wirelessly coupled with the proximal portion of the catheter body. Optionally, a two-dimensional input device is mounted to the housing, the processor configured to move the distal portion of the catheter body in two additional degrees of freedom in response to input received by the two-dimensional input. In preferred embodiments, the sensor measures movement of the housing in three or more degrees of freedom, optionally in three translational degrees of freedom and two or three orientational degrees of freedom.

In another aspect, the invention provides a catheter articulation system for use by a user having a hand so as to treat or diagnose a patient. The catheter articulation system comprises an elongate catheter body having a proximal portion and a distal portion with an axis therebetween. The distal portion of the catheter body can be configured for insertion into a patient through an aperture. A plurality of actuators can be operatively coupled with the distal portion of the catheter body, and an input can be configured to facilitate reorientation by the hand of the user toward alignment with the inserted distal portion of the catheter body and/or with the patient. A sensor can be coupled to the input to receive a movement command having a command orientation. A processor can be configured for coupling the sensor to the actuators so that, during use, the distal portion of the catheter body moves, in response to the movement command, with a catheter movement having a movement orientation corresponding to the command orientation based on the reoriented input.

Advantageously, not all input axes need to be moved by the user into a precisely parallel relationship with the corresponding output axes for safe and efficient use of the systems described herein. Systems which facilitate user input re-orientation about just a single axis during a procedure (ideally after the patient is positioned on the surgical table or other patient support surface, after an image of target lumen or other tissue has been captured and shown in a display, and/or after the articulated catheter has been inserted into the patient and advanced to or near the target treatment site) may provide significant efficiency benefits. For example, the input may have a base surface that will rest securely on a flat support surface while receiving rotational inputs, and which can be manually reoriented about a vertical axis by picking up or otherwise rotating the base surface relative to the support. Typically, the processor will be configured to calculate actuators signals to transmit to a subset of the actuators to induce the catheter movement based on the movement command orientation, with the processor identifying the subset of actuators using a transformation. Input devices described herein may facilitate reorientation in a plurality of orientations, and configurations of the system which facilitate movement of the input toward or into effective alignment using the hand of the user may include input systems having an input base configured to be picked-up and/or held, rotated, twisted, or otherwise to be readily reoriented about any one, two, or all three input orientation axes (input roll, input pitch, and input yaw) during a procedure. Note that the input/output alignment need not be maintained throughout a procedure; once the user provides effective alignment between the input and output, the system can measure and store the aligned input orientation and the user can move the input to a desired (often a more comfortable or ergonomic) orientation. The system may measure the desired input orientation and determine the change from the stored input orientation to the desired orientation, and may calculate a transform so that the input and output movements remain coordinated.

Optionally, the distal portion may be articulatable in two degrees of freedom, three degrees of freedom, or more. The movement command may comprise a two-dimensional or three-dimensional movement command (or more) including a change in position or a change in orientation or both, and the processor may determine a plurality of drive signals based on the user's alignment of the input with the catheter structure so as to drive a plurality of separate actuators such that the movement orientation is aligned with the command orientation.

Also optionally, the sensor can comprise an accelerometer, a gyroscope, an inertial measurement unit, an image capture device, and/or a flexible body shape sensor. The movement command may comprising a movement of a housing containing the sensor. The sensor may comprise an at least 2D accelerometer and/or an at least 2D gyroscope, and the movement command may comprise tilting of the body in at least two degrees of freedom. When appropriate, the sensor may comprise an at least 2D accelerometer, an image capture device, and/or a flexible shape body sensor, and the movement command may comprise translating the body in at least two degrees of freedom. In some cases, the input can be configured to be moved by the hand of the user in 6 degrees of freedom, and the sensor can receive the movement command in 6 degrees of freedom.

Preferably, a clutch input is coupled to the processor, and the processor is configured to induce movement of the distal portion of the catheter in response to movement of the input body when the clutch input is actuated, and to inhibit commanded movement of the distal portion of the catheter in response to movement of the input when the clutch input is not actuated. Regardless, the input may comprise an at least two-dimensional input component mounted to an input body. The processor can be configured to induce aligned movement of the distal portion of the catheter body about a first coupling location along the axis in response to movement of an input body about a second coupling location so that the user perceives that the coupling locations correspond. The distal portion of the catheter may include an articulatable segment and a therapeutic or diagnostic tool distal of the articulatable segment, and the first coupling location can be disposed distal of the articulatable segment. As yet another general feature, the input can have an axis and a rotational alignment input coupled with the processor. The processor can be configured to alter a rotational alignment of a first lateral orientation about the axis of the catheter so as to correspond with a second lateral orientation about the axis of the input in response to an alignment command received by the alignment input. Advantageously, the input body can be elongate along the axis of the input body with a proximal portion and a distal portion differentiated from the proximal portion (often so as to facilitate tactile identification of the input orientation in the hand) The distal portion of the catheter body may have an elongate image with a distal end visually identifiable when displayed on a remote imaging system so as to facilitate manual rotational alignment, by the user, of the input body with the image of the distal portion.

In another aspect, the invention provides a catheter system for use by a user having a hand. The catheter articulation system comprises an elongate catheter body having a proximal portion and a distal portion with an axis therebetween. The distal portion of the catheter body may be configured for insertion into a patient through an aperture. A housing can be coupleable with the proximal portion of the catheter body and configured to be manipulated by the hand of the user while the proximal portion of the catheter body is coupled to the housing so as to move the distal portion within the patient. A drive system may be contained within the housing and catheter body, and a processor can be coupled with the drive system so that the distal portion of the catheter body moves in response to the movement command. Optionally, the housing can be configured to be held in the hand during driven movement of the distal portion or to be lifted by the hand onto a flat surface to rest thereon during driven movement of the distal portion.

In general, the drive system may be contained within the proximal housing and the catheter. The housing may have a bottom surface that is configured to rest in a stable position and orientation on a flat support, so as to remain fixed during actuator-induced articulation of the distal portion within the patient. The bottom surface may be sufficiently positionally stable on the support so as to inhibit inadvertent movement during actuated articulation, such as not moving or being toppled over by forces of about a quarter pound or less, a half pound or less, or a pound or less. Nonetheless, the housing may be slidable on the support in response to an axial manipulating forces, for example, of a half pound or more, a pound or more, or the like.

The catheter systems described herein will often be configured for use with a remote imaging system having an image capture device and a display. The input may have an input reference frame and the distal portion may have a distal portion reference frame, and the display may show the distal portion in a display reference frame that is associated with a relationship between the image capture frame and the distal catheter frame. The system can be configured to maintain coordination between, for example: a first movement command in the input reference frame and a first catheter articulation as shown in the display reference frame, the first movement command being prior to the manual movement; and a second movement command in the input reference frame and a second catheter articulation as shown in the display reference frame, the second movement command being after the manual movement.

Any of the inputs described herein may optionally include a twist input that is manually rotatable relative to the housing coupled to the proximal catheter about a twist input axis extending along the catheter axis, with the twist input optionally comprising a rotatable wheel surrounding the catheter so that manually manipulating the twist input mimics rotation of a proximal catheter handle. The processor can be configured so that rotation of the twist input induces articulation of the distal portion that mimics rotation of the catheter body about the axis without rotating the proximal portion of the catheter adjacent the aperture. For example, rotating the twist input clockwise may cause laterally deflection(s) of the distal catheter portion to propagate clockwise about the catheter axis by an amount roughly equal to (or otherwise proportional to) the input twist.

Any of the processors of the catheter systems described herein may optionally have a manual movement state and an actuated movement state. A sensor can be coupleable with the housing so as to transmit manual movement signals indicative of manual manipulation of the housing suitable for manually moving the distal portion of the catheter within the patient. Suitable sensors may include any of the motion sensors described herein, contact sensors, translation sensors for sensing sliding of the housing across a surface (similar to a computer mouse movement sensor), or the like. The processor can be configured to change from the actuated movement state to the manual movement state in response to the manual movement signals. Optionally, the processor may be configured so that the change from the articulated movement state to the manual movement state: inhibits at least some articulation of the distal portion; reduces an anchoring engagement between the distal portion and adjacent tissue; and/or alters a stiffness of the distal portion. For example, twist input may result in actuated movement mimicking rotation of the catheter, but other changes in the actuated shape or pose of the catheter distal portion may be inhibited. Anchoring engagement may be decreased during sensed manual movement sufficiently to facilitate manual repositioning of the distal portion within the patient, optionally using an anchor decrease command calculated by the processor so as to reduce tissue engagement forces below a threshold. Stiffness changes during manual movement may comprise decreasing stiffness of a distal segment (so as to inhibit tissue damage), increasing stiffness of a proximal segment (so as to increase manual repositioning accuracy) or both. In some embodiments, a mode input switch, button, or the like may be actuated to change the processor mode between the manual an automated movement modes. The processor may optionally return to the automated mode if no manual movement has occurred for a threshold time, such as 5 or 10 seconds.

In another aspect, the invention provides a catheter articulation system for use by a user having a hand. The catheter articulation system comprises an elongate catheter body having a proximal portion and a distal portion with an axis therebetween. The distal portion of the catheter body is configured for insertion into a patient through an aperture. A plurality of actuators is operatively coupled with the distal portion of the catheter body, and a body is releasably attached to the proximal portion of the catheter body. The body is configured to be moved by the hand of the user in three degrees of freedom. A sensor is coupleable to the body so as to receive a movement command comprising the movement of the body in the three degrees of freedom. A processor couples the sensor to the actuators so that the distal portion of the catheter body moves in response to the movement command.

In another aspect, the invention provides a catheter articulation system for use by a user having a hand. The catheter articulation system comprises an elongate catheter body having a proximal portion and a distal portion with an axis therebetween. The distal portion of the catheter body is configured for insertion into a patient through an aperture. A plurality of actuators is operatively coupled with the distal portion of the catheter body. A housing is releasably attached to the proximal portion of the catheter body, and is configured for supporting with the hand of the user. A sensor system is mounted to the housing. The sensor system comprises an accelerometer and is configured to measure movement of the housing in a plurality of degrees of freedom so as to receive a movement command from the hand supporting the housing. A processor couples the sensor to the actuators so that the distal portion of the catheter body moves in response to the movement command.

In another aspect, the invention provides a surgical actuation system comprising an introducer. The introducer may include a sheath body having proximal end and a distal end with a lumen extending therebetween (the distal end being advanceable into a patient body), an input base adjacent the proximal end of the sheath body, an input movable relative to the base so as to receive a movement command from a hand of a user, and a sensor coupling the input to the base so that, in use, the sensor transmits a command signal in response to the movement command. Along with the introducer sheath, an elongate flexible body is included, with the body having a proximal end and a distal end with an axis therebetween. The distal end can be configured for axial insertion distally through the lumen of the sheath body and into the patient body. A drive system will often be coupleable with the elongate body, the drive system comprising a processor and a plurality of actuators. The processor can be configured to effect actuation of the actuators in response to the command signal so that the distal end of the elongate body is urged to move with a movement associated with the movement command.

In another aspect, the invention provides an input system for use in a surgical system. The surgical system may include an elongate flexible body configured for insertion distally into a patient body, and a drive system coupleable with the elongate body. The drive system may include an actuator and a processor configured to effect actuation of the actuator in response to a command signal so that the distal end of the elongate body is urged to move with a desired movement. The input system comprises an introducer sheath body having proximal end and a distal end and an axis therebetween. A lumen for receiving the elongate flexible body extends axially and the distal end is advanceable into a patient body. An input base adjacent the proximal end of the sheath body is also provided, and an input is movable relative to the base so as to receive a movement command from a hand of a user. A sensor couples the input to the base so that, in use, the sensor transmits a command signal suitable for inducing the desired movement of the elongate body in response to the movement command.

In yet another aspect, the invention provides a surgical system for use with tissue of a patient, the tissue accessible through a minimally invasive access site. The system comprises an elongate flexible proximal body having a proximal end and a distal end, the proximal body extending proximally from the minimally invasive access site during use. A sensor is operatively coupled with the proximal body, the sensor configured to transmit signals associated with flexing of the proximal body outside of the patient. An articulatable distal portion is configured to be advanced through the access site toward the tissue, the distal portion having bend characteristics that can be altered in response to drive signals. A processor operatively couples the distal portion with the sensor so that the manual flexing of the proximal body outside of the patient can be used to control articulation of the distal portion within the patient during use of the system in a powered articulation mode.

In yet another system aspect, the invention provides a surgical system for use within a body lumen of a patient, the lumen accessible through an access site. The system comprises an elongate body having a proximal end and a distal end with an axis therebetween, the elongate body including a first axial segment axially coupled with a second axial segment. Each axial segment has an associated local lateral stiffness. A length of the elongate body is configured to extend, during use, between the access site and the distal end, and that length has a pushability and a trackability. A first actuator can be coupled with the first axial segment and can be configured to selectively alter the local lateral stiffness (optionally by reducing the first local lateral stiffness, and often without inducing bending of the first axial segment absent environmental forces) along the first segment in response to a first signal. Hence, the first signal can be used to tailor the pushability and/or trackability of the length of the elongate body for a particular body lumen. In many embodiments, the first actuator is included in a plurality of actuators coupled with the elongate body, the plurality including a second actuator coupled with the second axial segment. The second actuator can be configured to selectively alter the local flexibility along the second segment in response to a second signal so that the signals can be used to tailor, for the body lumen, the pushability of the length of the elongate body or the trackability of the length of the elongate body or both, with the exemplary actuators comprising balloons.

In yet another system aspect, the invention provides a surgical system for use within a body lumen of a patient. The lumen is accessible through an access site, and the system comprises an elongate body having a proximal end and a distal end with an axis therebetween. The elongate body includes a first axial segment axially coupled with a second axial segment and with a third axial segment, each axial segment defining a local axial curvature during use. A first actuator is coupled with the first axial segment and configured to selectively alter the local axial curvature along the first segment in response to a first signal so as to steer the elongate body distal of the first actuator or align the elongate body distal of the first actuator with a target tissue. A second actuator is coupled with the second axial segment and a third actuator is coupled with the third axial segment. The second actuator is configured to selectively alter the local axial curvature along the second segment in response to a second signal; the third actuator is configured to selectively alter the local axial curvature along the third segment in response to a third signal. The signals can be used to tailor, for the body lumen, a safe anchoring engagement between the body lumen and the elongate body such that movement of the elongate body relative to the engaged body lumen is inhibited.

In a method aspect, the invention provides a surgical method comprising receiving a movement command defined by manually moving an input relative to a base. The input and the base can be included in an introducer/input assembly, which can further include a sheath body having proximal end and a distal end with a lumen extending therebetween. The movement command can be received after the distal end of the introducer has been introduced into a patient body, and a sensor may couple the input to the base so as to transmit a command signal in response to the movement command. A processor may process the command signals and transmit drive signals to a plurality of actuators. The actuators can be configured to articulate an elongate flexible body having a proximal end and a distal end with an axis therebetween. The distal end may be inserted distally through the lumen of the sheath body and into the patient body, and the drive signals may be transmitted so that the distal end of the elongate body is urged to move with a movement associated with the movement command.

In the devices, systems, and methods provided herein, an input base can generally be affixed to the sheath body of an introducer/input assembly during use, and that can be configured to be supported by another hand of the user. This facilitates defining a series of movement commands by relative movements between the hands of the user, with the hand on the input base stabilizing the introducer sheath so as to inhibit undesired movement adjacent the access site. This also allows the user to employ hand motions that are similar to those used during manual catheter manipulations, but to instead provide input commands that effect powered articulations of the distal portion of an inserted structure, and may facilitate transitions between manual movement of the distal portion and powered articulation.

Optionally, the input can be a relatively simple (and optionally disposable) structure. For example, the input may comprise an input body and an elongate flexible input shaft having a lumen. The lumen of the input shaft may receive the elongate flexible body therethrough, and the input shaft may extend distally of at least a proximal end of the input body. The input body may include a hemostatic valve and may optionally be releasably affixable to a catheter or other elongate body extending therethrough, so as to inhibit inadvertent movement of the catheter proximal of the distal articulated portion. The input body may also be releasably affixable to the input base, for example, when it is desired to manually manipulate the catheter without inducing articulation. The sensor can be coupled with the input body such that at least a portion of the command signal correspond to lateral flexing of the input body, which may allow the user to employ manual input commands that are particularly easily associated with lateral bending of the distal portion of the elongate body within the patient, sometimes referred to as X-Y bending or deflection. The input shaft can extend distally of the input body and can be slidably received in the lumen of the introducer. The sensor can be coupled to the input shaft such that at least a portion of the command signal corresponds to a change in axial overlap between the input shaft and the introducer assembly, allowing the user to employ manual input commands that are particularly easily associated with powered axial movement (including elongation and retraction) of the distal portion of the elongate body (sometimes referred to as Z actuation). Note that the articulation system will often employ only a subset of these capabilities, with some systems allowing articulation only in a single lateral direction.

The sensors of the devices and systems provided herein may take any of a variety of forms, with exemplary embodiments of the sensor comprising an optical Fiber Bragg Grating (FBG), a flex-sensitive electrical component (such as one or more thin-film resistor deposited on the input shaft so that it varies in resistance with flexing of the shaft), or the like. The sensor will often be mounted to the input, but may alternatively (or additionally) be mounted to the elongate flexible body, particularly when the elongate body includes an FBG or other flex sensor system for providing feedback to the processor to be used in generating the drive signals.

The introducer (often the input base of the introducer) may optionally include an introducer valve having a first configuration (such as with the elongate flexible body axially affixed to the introducer sheath) and a second configuration (such as with the elongate flexible body axially slidable through the introducer sheath). The input may comprise an input valve having a first configuration (such as with the elongate flexible body axially affixed to the input) and a second configuration (with the elongate flexible body axially slidable through the input), and an interface between the introducer and the input may have a first configuration (with the input base axially affixed to the input) and a second configuration (with the input axially movable relative to the input base). The processor can be coupled to the valve of the input base, the valve of the input, and/or the interface so that the drive signals are determined in response to the configurations. For example, when the input base is affixed to a catheter and the interface is moveable relative to the input base, the drive signals may effect X-Y deflection and elongation. When the catheter is affixed to the input and the input and catheter are movable relative to the input base, the drive signals may induce X-Y deflation but not elongation. When the input is affixed to the input base and the catheter moves through both, the drive signals may not induce any articulation (but may optionally facilitate lateral bending for tracking a lumen, guidewire, or the like).

The input preferably comprises a normally unactuated clutch input. In use, actuation of the clutch can define an initial state of the input. The processor can be configured to effect movement of the distal end of the elongate flexible body in response to a change of the input from the initial state when the clutch remains actuated. The processor may further be configured to disregard a change in state of the input when the clutch is unactuated. Hence, repeated actuated manual articulation of the input and unactuated manual returning of the input toward the initial state can be used to effect cumulatively increasing articulation of the elongate flexible body.

A first connector typically couples the processor to the input, and a second connector couples the proximal end of the elongate flexible body with the processor. The connectors may include quick-disconnect couplers and flexible cables. The processor can be disposed in a housing, and the housing may also contain a battery and a pressurized fluid canister (both of which may be either rechargeable or replaceable). The actuators may comprise fluid-driven actuators and the housing may have a size, weight, and shape suitable for manually repositioning with a single hand during use.

In many embodiments, the input comprises an X-Y lateral displacement input, and an X-Y laterally displacement of the movement command may induce lateral flexing the elongate flexible body proximally of the patient body during use. The drive system can have software and hardware configured to articulate the distal end of the elongate flexible body in response to the movement command with two degrees of freedom (including X-Y lateral bending) within the patient. The input may optionally comprise an axial Z displacement input, wherein the movement command comprises an axial Z movement of the input along the axis of the elongate flexible body during use. The drive system can be configured to, during use, do one or more of the following two options: 1) axially move the distal end of the elongate flexible body within the patient body and relative to a proximal portion of the elongate flexible body in correlation with the axial movement of the input, the axial movement of the input comprising sliding movement of the input over the proximal portion of the elongate flexible body; and/or 2) laterally flex the distal end of the elongate flexible body in coordination with axial movement of at least a portion of the elongate flexible body so that the elongate flexible body moves along a desired curve within the patient body. When the movement command comprises axial advancement of the input with the elongate flexible body adjacent the input moving axially with the input, the processor can be configured to drive the actuators so that the distal end of the elongate flexible body follows the desired curved within the patient body; and/or so that a curve along the elongate flexible body proximal of the distal end propagates proximally with advancement of the elongate flexible body in correlation with the axial movement. In some embodiments, the processor has an axial actuation recovery mode to effect coordinated proximal movement of the distal end of the elongate flexible body relative to the proximal portion of the elongate flexible body during manual advancement of the proximal portion of the elongate flexible body. Optionally, at least one of the actuators comprises a balloon.

The articulated bodies to be controlled by the user interface devices, systems, and methods described herein may have large numbers of degrees of freedom. In many embodiments (and particularly medical embodiments) it would be preferable for the system user to be able to provide movement commands with a single hand, often while supporting the input device in that hand. In medical applications, the system user and input device may be in or adjacent to a sterile surgical field, and may have tasks to perform with their other hand (optionally including inserting the catheter body through an introducer sheath and into the patient. One optional feature of many of the devices and system described herein is that a body being manually moved by a hand of a user may optionally comprise a housing, at least a portion of the processor being disposed in the housing. The movement command input into the system may comprise a change in position of the housing or a change in orientation of the housing or both. Another optional feature is that the sensor that senses the movement command comprises an accelerometer, a gyroscope, an inertial measurement unit, an image capture device, and/or a fiber Bragg grating. Another optional feature is that the sensor comprises a 2D accelerometer and/or a 2D gyroscope, for example, with the movement command comprising tilting of the body in two degrees of freedom. Yet another optional feature is that the sensor comprises a 2D accelerometer, an image capture device, and/or a fiber Bragg grating, with (for example) the movement command comprising translating the body in two degrees of freedom.

A number of optional feature may be included in embodiments which receive input commands as movements of a housing body or the like. For example, the sensor system that receives the movement command input as a movement of the housing may be configured to sense movement in the housing in 2, 3, 4, 5, or 6 degrees of freedom, with the sensor typically transmitting signals to the system processor associated with movement of the housing in each of the sensed degrees of freedom. A clutch input may be coupled to the processor, and the processor may be configured to inducement movement of the distal portion of the catheter in response to movement of the body when the clutch input is actuated, and to inhibit commanded movement of the distal portion of the catheter despite any movement of the body when the clutch input is not actuated. A two-dimensional input may be mounted to the body and coupled to the processor, with the two dimensional input configured to receive movement commands that are in addition to those associated with movement of the body. The processor may induce other movements of the distal portion of the catheter in response to these 2-D movement commands, the other movements similarly being in addition to those induced by the movement of the body. The processor can be configured to inducement movement of the distal portion of the catheter body about a first coupling location along the axis in response to movement of the body about a second coupling location of the housing, with the induced movements being aligned so that the user perceives the coupling locations correspond. The distal portion of the catheter optionally includes an articulatable segment and a therapeutic or diagnostic tool distal of the articulatable segment, and the first coupling location may be disposed distal of the articulatable segment. Preferably, the body has an axis (it optionally being an elongate body or the like) and a rotational alignment input will be coupled with the processor. The processor can be configured to alter a rotational alignment of a first lateral orientation about the axis of the catheter to a second lateral orientation of the body in response to an alignment command received by the alignment input, the alignment input ideally comprising a rocker switch biased to an intermediate position (so that the user can intuitively alter alignment in opposed orientations), a thumb wheel, or the like. Electrical and/or optical contacts may be included in a connector of the catheter and a receiver of the housing so as to facilitate transmission of feedback signals from the catheter to the system processor, with the feedback signals being indicative of a shape and/or location of the distal portion of the catheter and being available to the processor to more accurately drive articulation.

In another aspect, the invention provides a catheter articulation system for use by a user having a hand. The catheter articulation system comprises an elongate catheter body having a proximal portion and a distal portion with an axis therebetween. The distal portion of the catheter body is configured for insertion into a patient through an aperture. A plurality of actuators is operatively coupled with the distal portion of the catheter body. A housing is coupleable with the proximal portion of the catheter body and configured to be supported with the hand of the user. A sensor system can be mounted to the housing, the sensor system comprising an accelerometer and configured to measure movement of the housing in a plurality of degrees of freedom so as to receive a movement command from the hand supporting the housing. A processor may couple the sensor to the actuators so that the distal portion of the catheter body moves in response to the movement command.

In some embodiments, the housing contains a battery and is wirelessly coupled with the proximal portion of the catheter body. Optionally, a two-dimensional input device is mounted to the housing, the processor configured to move the distal portion of the catheter body in two additional degrees of freedom in response to input received by the two-dimensional input.

BRIEF DESCRIPTION OF THE DRAWINGS

FIG. 1-1 schematically illustrates a catheter articulation system having a hand-held proximal housing and a catheter with a distal articulatable portion in a relaxed state.

FIGS. 9-12 are perspective drawings showing an exemplary flat-pattern substrate and associated balloon array generated by unwinding a helical balloon pattern, along with an exemplary bonded balloon fabrication technique.

FIGS. 16F-16H schematically illustrate use of the sheath/input assembly of FIG. 14 in a "follow-the-curve" mode, in which axial displacement of the catheter is measured and induces corresponding lateral deflections along one or more axial segments of the articulable portion of the catheter.

FIGS. 16I and 16J schematically illustrate use of the sheath/input assembly of FIG. 14 in a local stiffness varying mode, in which axial displacement of the catheter is measured and induces localized changes in stiffness of the catheter so that a pushability and/or trackability of the overall catheter is tailored for that body lumen's geometry.

FIGS. 23A-23H are illustrations of alternative elongate articulated flexible structures having annular skeletons and two sets of opposed balloons, and show how a plurality of independently controllable axial segments can be combined to allow control of the overall elongate structure with 6 or more degrees of freedom.

FIGS. 25A-25F illustrate exemplary elongate articulated flexible structures having helical skeleton members and three helical balloon assemblies supported in opposition along the skeleton, and also show how selective inflation of subsets of the balloons can locally axially elongate and/or contract the skeleton to bend the structure laterally and/or alter the overall length of the structure.

FIGS. 33A, 33B, and 33C schematically illustrate nine articulated degrees of freedom of a catheter having three independently articulatable segments, three orientational degrees of freedom of a housing of an input device, and three translational degrees of freedom of the input housing, respectively.

FIGS. 35A-35D schematically illustrate optional correlations between degrees of freedom of the input housing and articulated degrees of freedom of the catheter.

FIG. 35E schematically illustrates an alternative hand-held catheter system having a user interface housing which can be detached from the manifold assembly, with the user interface housing being movable by a hand of a system user so as to define movement commands.

DETAILED DESCRIPTION OF THE INVENTION

Figure 1:
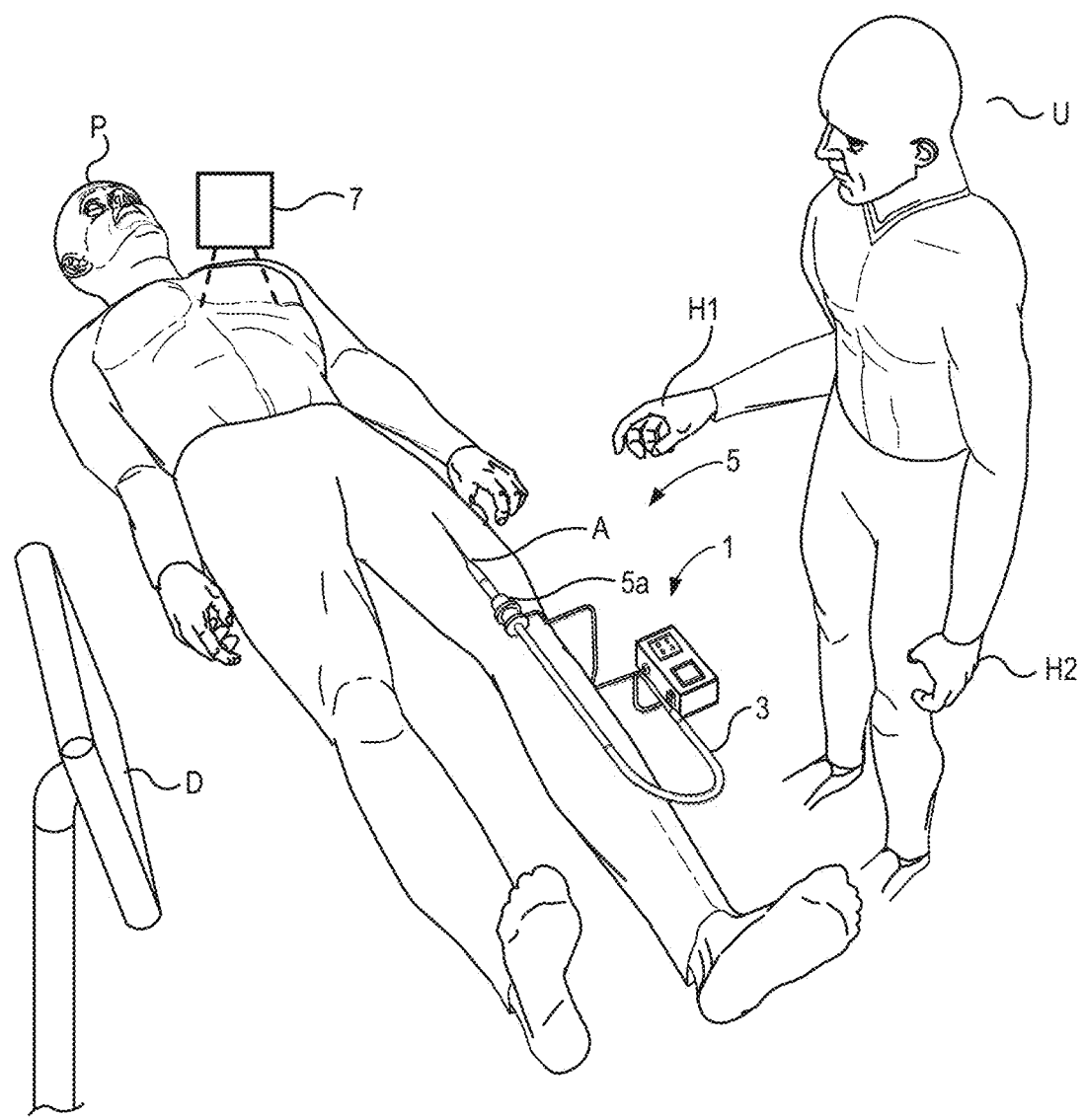
FIG. 1 is a simplified perspective view of a medical procedure in which a physician can input commands into an catheter system so that a catheter is articulated using systems and devices described herein.
Figure 1:
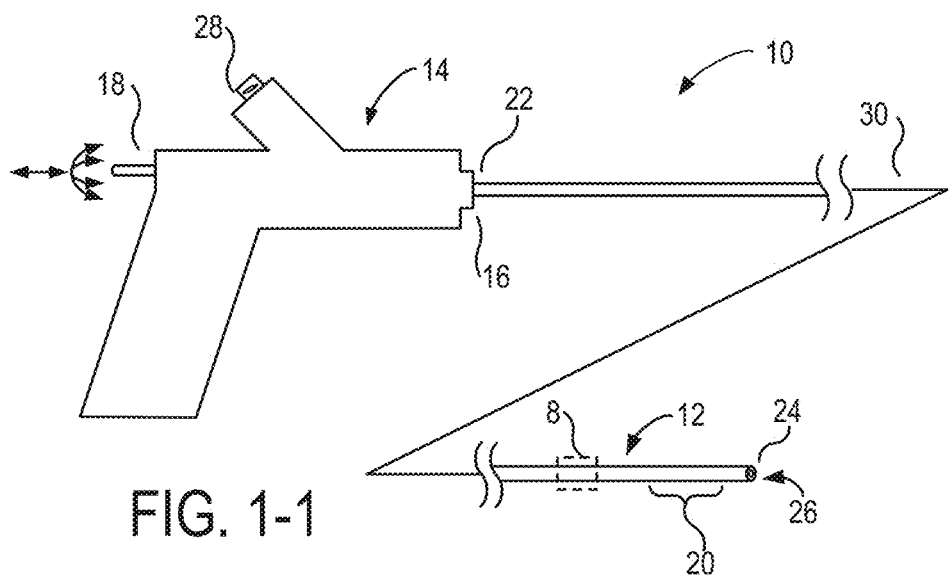

The present invention generally provides improved devices, systems, and methods for controlling movement, and in exemplary embodiments, for inputting movement commands from a user to induce movement of elongate flexible articulated devices. The technologies described herein are particularly well-suited for use by physicians and other health-care professionals, and will often be used to help direct computer-controlled movements of catheters and other articulated devices when they are inserted into a body lumen or cavity of a patient. The elongate flexible structures may have 3, 4, 5, 6, 7, 8, or more active or computer-controlled degrees of freedom, and many, most, or all of those degrees of freedom may be distributed along an axis of the body lumen during use; although many, most, or all of those degrees of freedom may also be within an open workspace (unsupported by surrounding tissues) during at least a portion of a procedure. The invention can help provide intuitive control over these and other articulated devices with surprisingly simple input structures, with the input structures optionally being configured to be hand-held, optionally by a single hand while the input structure is receiving input, for example, with the movements comprising movements of the overall hand and held input structure, or being provided from one or more digits of that hand, leaving the other hand free for other tasks. Alternatively, the input structure may be configured to be used while held in one hand of a user with the input commands are provided by the other hand of the user, or the input structure may be supported by a flat, roughly horizontal surface so that the user can slidably reposition and reorient the input structure relative to the patient anatomy, imaging displays, or the like.

Surprisingly, the user may manipulate fewer discrete and/or sensed input joint degrees of freedom than those being commanded. For example, movement of a hand-held housing of the input structure by the hand holding the housing may be sensed in 1, 2, or 3 three positional degrees of freedom (such as displacement along X, Y, and/or Z axes) and in 1, 2, or 3 orientational degrees of freedom (such as rotation about roll, pitch, and/or yaw axes). Sensing of this housing pose data may be performed by a movement sensor (such as a micro-electro-mechanical system (MEMS) accelerometer, gyroscope, and/or inertial measurement unit (IMU)), by an image capture device (such as an optical camera, infra-red camera, or stereoscopic camera), by a flexible body shape sensor (such as a fiber Bragg grating (FBG) sensor or elastomeric printed electrical components), by an electromagnetic navigation sensor, or the like; and will optionally be performed by at least two different sensor types. While external sensor components may be used, the housing pose data may optionally be obtained and analyzed using components that are mostly or even entirely contained within the hand-held housing (for example, using indoor navigation technologies developed for smart phones). This housing pose data may optionally be combined with signals from a simple multiple degree of freedom input device (such as a joystick or the like) mounted to the housing to provide effective control over more than 6 articulation degrees of freedom (sometimes called degrees of freedom in joint space) with a single hand of the user.

Embodiments provided herein may use balloon-like structures to effect articulation of the elongate catheter or other body. The term "articulation balloon" may be used to refer to a component which expands on inflation with a fluid and is arranged so that on expansion the primary effect is to cause articulation of the elongate body. Note that this use of such a structure is contrasted with a conventional interventional balloon whose primary effect on expansion is to cause substantial radially outward expansion from the outer profile of the overall device, for example to dilate or occlude or anchor in a vessel in which the device is located. Independently, articulated medial structures described herein will often have an articulated distal portion, and an unarticulated proximal portion, which may significantly simplify initial advancement of the structure into a patient using standard catheterization techniques.

The catheter bodies (and many of the other elongate flexible bodies that benefit from the inventions described herein) will often be described herein as having or defining an axis, such that the axis extends along the elongate length of the body. As the bodies are flexible, the local orientation of this axis may vary along the length of the body, and while the axis will often be a central axis defined at or near a center of a cross-section of the body, eccentric axes near an outer surface of the body might also be used. It should be understood, for example, that an elongate structure that extends "along an axis" may have its longest dimension extending in an orientation that has a significant axial component, but the length of that structure need not be precisely parallel to the axis. Similarly, an elongate structure that extends "primarily along the axis" and the like will generally have a length that extends along an orientation that has a greater axial component than components in other orientations orthogonal to the axis. Other orientations may be defined relative to the axis of the body, including orientations that are transvers to the axis (which will encompass orientation that generally extend across the axis, but need not be orthogonal to the axis), orientations that are lateral to the axis (which will encompass orientations that have a significant radial component relative to the axis), orientations that are circumferential relative to the axis (which will encompass orientations that extend around the axis), and the like. The orientations of surfaces may be described herein by reference to the normal of the surface extending away from the structure underlying the surface. As an example, in a simple, solid cylindrical body that has an axis that extends from a proximal end of the body to the distal end of the body, the distal-most end of the body may be described as being distally oriented, the proximal end may be described as being proximally oriented, and the surface between the proximal and distal ends may be described as being radially oriented. As another example, an elongate helical structure extending axially around the above cylindrical body, with the helical structure comprising a wire with a square cross section wrapped around the cylinder at a 20 degree angle, might be described herein as having two opposed axial surfaces (with one being primarily proximally oriented, one being primarily distally oriented). The outermost surface of that wire might be described as being oriented exactly radially outwardly, while the opposed inner surface of the wire might be described as being oriented radially inwardly, and so forth.

Some or all of the systems described herein may benefit from orientational alignment between the input and output structures. As the term is used herein, orientational alignment between an input (such as a joystick moveable along a first movement command axis, a housing movement axis, or the like) and an output (such as a corresponding first lateral articulation axis of an articulated catheter or the axis of the catheter adjacent the distal end) encompasses but does not require that the corresponding input and the output axes be exactly parallel. Functionally, input and output reference frames that are within a range of angles from parallel can be perceived by a majority of system users having a threshold amount of experience as generating output movements that correspond sufficiently to input movements to provide efficient eye/hand coordination, and input/output angular relationships that are within such a range are considered herein to have orientational alignment. Note that the range of effectively orientationally aligned angles may vary among differing articulation axes (i.e., pitch, yaw, roll, up/down, left/right, in/out), and the acceptable angular offsets may be smaller for input/output systems having more degrees of freedom. Regardless, while the desirable angular range(s) for a particular user may be subjective, whether a particular input/output orientational relationship is within an effectively aligned angular range for most users in a typical population for a particular system may be empirically quantified based on statistical analysis of user times to perform appropriate benchmark tasks, with acceptable orientations resulting in most user task times within a desired threshold (for example, 10%, 20%, 40%, or the like) of those associated with a parallel input/output relationship.

Referring first to FIG. 1, a first exemplary catheter system 1 and method for its use are shown. A physician or other system user U interacts with catheter system 1 so as to perform a therapeutic and/or diagnostic procedure on a patient P, with at least a portion of the procedure being performed by advancing a catheter 3 into a body lumen and aligning an end portion of the catheter with a target tissue of the patient. More specifically, a distal end of catheter 3 is inserted into the patient through an access site A, and is advanced through one of the lumen systems of the body (typically the vasculature network) while user U guides the catheter with reference to images of the catheter and the tissues of the body obtained by a remote imaging system.

In this exemplary embodiment, catheter system 1 may be used in a manual mode during a portion of the procedure. In the manual mode, user U can help advance, retract, or position the distal end of the catheter within the patient by manually grasping the exposed catheter shaft near the patient and moving the catheter shaft relative to the patient, often while also holding an introducer sheath of the assembly to prevent the introducer sheath from being dislodged. Alternatively, user U may grasp a proximal or housing affixed to the proximal end of the catheter body with one hand (for example, using a forefinger and/or a thumb to intermittently adjust a steering bend angle or the like, with the rest of the hand supporting the housing), and may manipulate the catheter relative to the introducer with the other hand (for example, with the thumb and forefinger grasping and manipulating the catheter body and the remaining fingers holding the introducer in place). The input for powered movement of catheter system 1 may to some extent mimic these manual manipulations so as to facilitate driving the catheter in an automated articulation mode, and also to facilitate the transitions between manual and automated articulation modes. For example, user U may grasp a first exposed portion of assembly 5a using fingers of a first hand H1 (to inhibit introducer sheath displacement), and may also grasp and manipulate another exposed portion of assembly 5a near the patient using fingers of a second hand H2. Alternatively, the user may grasp the introducer and adjacent catheter with one hand, and may move a proximal housing or handle of the catheter with the other. In either case, relative movements of these grasped components can be used as input movement commands to the automated catheter system, with those relative movements being reminiscent of the hand movements used in the manual mode (and of the hand movements used for manipulation of known manual catheter systems). While often described herein with reference to manipulation of a catheter, these devices, system, and methods will also be well suited for manipulation of other medical structures including guidewires and the like, and may also be used for manipulation of non-medical structures such as industrial endoscopes or boroscopes and the like.

Exemplary catheter system 1 will often be introduced into patient P through one of the major blood vessels of the leg, arm, neck, or the like. A variety of known vascular access techniques may also be used, or the system may alternatively be inserted through a body orifice or otherwise enter into any of a number of alternative body lumens. The imaging system will generally include an image capture system 7 for acquiring the remote image data and a display D for presenting images of the internal tissues and adjacent catheter system components. Suitable imaging modalities may include fluoroscopy, computed tomography, magnetic resonance imaging, ultrasonography, combinations of two or more of these, or others.

Catheter 3 may be used by user U in different modes during a single procedure, including two or more of a manual manipulation mode, an automated and powered shape-changing mode, and a combination mode in which the user manually moves the proximal end while a computer articulates the distal portion. More specifically, at least a portion of the distal advancement of catheter 3 within the patient may be performed in a manual mode, with system user U manually manipulating the exposed proximal portion of the catheter relative to the patient using hands H1, H2. Catheter 3 may, for example, be manually advanced over a guidewire, using either over-the-wire or rapid exchange techniques. Catheter 3 may also be self-guiding during manual advancement (so that for at least a portion of the advancement of catheter 3, a distal tip of the catheter may guide manual distal advancement). Automated lateral deflection of a distal portion of the catheter may impose a desired distal steering bend prior to a manual movement, such as near a vessel bifurcation, followed by manual movement through the bifurcation. In addition to such manual movement modes, catheter system 1 may also have a 3-D automated movement mode using computer controlled articulation of at least a portion of the length of catheter 3 disposed within the body of the patient to change the shape of the catheter portion, often to advance or position the distal end of the catheter. Movement of the distal end of the catheter within the body will often be provided per real-time or near real-time movement commands input by user U, with the portion of the catheter that changes shape optionally being entirely within the patient so that the movement of the distal portion of the catheter is provided without movement of a shaft or cable extending through the access site. Still further modes of operation of system 1 may also be implemented, including concurrent manual manipulation with automated articulation, for example, with user U manually advancing the proximal shaft through access site A while computer-controlled lateral deflections and/or changes in stiffness over one or more axial segments along a distal portion of the catheter help the distal end follow a desired path and/or reduce resistance to the axial movement.

Referring next to FIG. 1-1 components which may be included in or used with catheter system 1 or catheter 3 (described above) can be more fully understood with reference to an alternative catheter system 10 and its catheter 12. Catheter 12 generally includes an elongate flexible catheter body and is detachably coupled to a handle 14, preferably by a quick-disconnect coupler 16. Handle 14 (and similar proximal handles having steering input capabilities) may be used in place of or together with assembly 5a (also described above), so that components of such handles can be included in the user interface of the catheter system. Catheter body 12 has an axis 30, and an input 18 of handle 14 can be moved by a user so as to locally alter the axial bending characteristics along catheter body 12, often for variably articulating an actuated portion 20 of the catheter body. Catheter body 12 will often have a working lumen 26 into or through which a therapeutic and/or diagnostic tool may be advanced from a proximal port 28 of handle 14. Alternative embodiments may lack a working lumen, may have one or more therapeutic or diagnostic tools incorporated into the catheter body near or along actuated portion 20, may have a sufficiently small outer profile to facilitate use of the body as a guidewire, may carry a tool or implant near actuated portion 20 or near distal end 26, or the like. In particular embodiments, catheter body 12 may support a therapeutic or diagnostic tool 8 proximal of, along the length of, and/or distal of actuated portion 20. Alternatively, a separate elongate flexible catheter body may be guided distally to a target site once catheter body 20 has been advanced (with the elongate body for such uses often taking the form and use of a guidewire or guide catheter).

The particular tool or tools included in, advanceable over, and/or introducible through the working lumen of catheter body 20 may include any of a wide range of therapeutic and/or treatment structures. Examples include cardiovascular therapy and diagnosis tools (such as angioplasty balloons, stent deployment balloons or other devices, atherectomy devices, tools for detecting, measuring, and/or characterizing plaque or other occlusions, tools for imaging or other evaluation of, and/or treatment of, the coronary or peripheral arteries, structural heart tools (including prostheses or other tools for valve procedures, for altering the morphology of the heart tissues, chambers, and appendages, and the like), tools for electrophysiology mapping or ablation tools, and the like); stimulation electrodes or electrode implantation tools (such as leads, lead implant devices, and lead deployment systems, leadless pacemakers and associated deployments systems, and the like); neurovascular therapy tools (including for accessing, diagnosis and/or treatment of hemorrhagic or ischemic strokes and other conditions, and the like); gastrointestinal and/or reproductive procedure tools (such as colonoscopic diagnoses and intervention tools, transurethral procedure tools, transesophageal procedure tools, endoscopic bariatric procedure tools, etc.); hysteroscopic and/or falloposcopic procedure tools, and the like; pulmonary procedure tools for therapies involving the airways and/or vasculature of the lungs; tools for diagnosis and/or treatment of the sinus, throat, mouth, or other cavities, and a wide variety of other endoluminal therapies and diagnoses structures. Such tools may make use of known surface or tissue volume imaging technologies (including imaging technologies such as 2-D or 3-D cameras or other imaging technologies; optical coherence tomography technologies; ultrasound technologies such as intravascular ultrasound, transesophageal ultrasound, intracardiac ultrasound, Doppler ultrasound, or the like; magnetic resonance imaging technologies; and the like), tissue or other material removal, incising, and/or penetrating technologies (such a rotational or axial atherectomy technologies; morcellation technologies; biopsy technologies; deployable needle or microneedle technologies; thrombus capture technologies; snares; and the like), tissue dilation technologies (such as compliant or non-compliant balloons, plastically or resiliently expandable stents, reversibly expandable coils, braids or other scaffolds, and the like), tissue remodeling and/or energy delivery technologies (such as electrosurgical ablation technologies, RF electrodes, microwave antennae, cautery surfaces, cryosurgical technologies, laser energy transmitting surfaces, and the like), local agent delivery technologies (such as drug eluting stents, balloons, implants, or other bodies; contrast agent or drug injection ports; endoluminal repaving structures; and the like), implant and prosthesis deploying technologies, anastomosis technologies and technologies for applying clips or sutures, tissue grasping and manipulation technologies; and/or the like. In some embodiments, the outer surface of the articulation structure may be used to manipulate tissues directly. Non-medical embodiments may similarly have a wide range of tools or surfaces for industrial, assembly, imaging, manipulation, and other uses.

Addressing catheter body 12 of system 10 (and particularly articulation capabilities of actuated portion 20) in more detail, the catheter body generally has a proximal end 22 and a distal end 24 with axis 30 extending between the two. As can be understood with reference to FIG. 2, catheter body 12 may have a short actuated portion 20 of about 3 diameters or less, but will often have an elongate actuated portion 20 extending intermittently or continuously over several diameters of the catheter body (generally over more than 3 diameters, often over more than 10 diameters, in many cases over more than 20 diameters, and in some embodiments over more than 40 diameters). A total length of catheter body 12 (or other flexible articulated bodies employing the actuation components described herein) may be from 5 to 500 cm, more typically being from 15 to 260 cm, with the actuated portion optionally having a length of from 1 to 150 cm (more typically being 2 to 20 cm) and an outer diameter of from 0.65 mm to 5 cm (more typically being from 1 mm to 2 cm). Outer diameters of guidewire embodiments of the flexible bodies may be as small as 0.012" though many embodiments may be more than 2 Fr, with catheter and other medical embodiments optionally having outer diameters as large as 34 French or more, and with industrial robotic embodiments optionally having diameters of up to 1" or more. Exemplary catheter embodiments for structural heart therapies (such as trans-catheter aortic or mitral valve repair or implantation, left atrial appendage closure, and the like) may have actuated portions with lengths of from 3 to 30 cm, more typically being from 5 to 25 cm, and may have outer profiles of from 10 to 30 Fr, typically being from 12 to 18 Fr, and ideally being from 13 to 16 Fr. Electrophysiology therapy catheters (including those having electrodes for sensing heart cycles and/or electrodes for ablating selected tissues of the heart) may have sizes of from about 5 to about 12 Fr, and articulated lengths of from about 3 to about 30 cm. A range of other sizes might also be implemented for these or other applications.

Figure 1A:
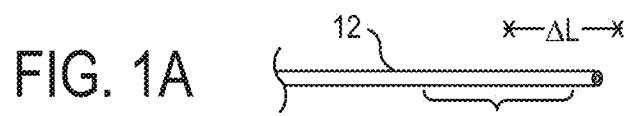
FIGS. 1A-1C schematically illustrate a plurality of alternative articulation states of the distal portion of the catheter in the system of FIG. 1.
Figure 1B:
Figure 1C:

Referring now to FIGS. 1A, 1B, and 1C, system 10 may be configured to articulate actuated portion 20. Articulation will often allow movement continuously throughout a range of motion, though some embodiments may provide articulation in-part or in-full by selecting from among a plurality of discrete articulation states. Catheters having opposed axial extension and contraction actuators are described herein that may be particularly beneficial for providing continuous controlled and reversible movement, and can also be used to modulate the stiffness of a flexible structure. These continuous and discrete systems share many components (and some systems might employ a combination of both approaches). First addressing the use of a discrete state system, FIG. 1A, system 10 can, for example, increase an axial length of actuated portion 20 by one or more incremental changes in length ΔL. An exemplary structure for implementation of a total selectable increase in length ΔL can combine a plurality of incremental increases in length $ΔL=ΔL_1+ΔL_2+\ldots$ ), as can be understood with reference to FIG. 4D. As shown in FIGS. 1B and 1C, system 10 may also deflect distal end 24 to a first bent state having a first bend angle 31 between unarticulated axis 30 and an articulated axis 30' (as shown schematically in FIG. 1B), or to a second bent state having a total bend angle 33 (between articulated axis 30 and articulated axis 30''), with this second bend angle being greater than the first bend angle (as shown schematically in FIG. 1C). An exemplary structure for combining multiple discrete bend angle increments to form a total bend angle 33 can be understood with reference to FIG. 4C. Regardless, the additional total cumulative bend angle 33 may optionally be implemented by imposing the first bend 31 (of FIG. 1B) as a first increment along with one or more additional bend angle increments 35. The incremental changes to actuated portion 20 may be provided by fully inflating and/or deflating actuation balloons of the catheter system. Bend capabilities may be limited to a single lateral orientation, but will more typically be available in different lateral orientations, most typically in any of 3 or 4 orientations (for example, using balloons positioned along two pairs of opposed lateral axes, sometimes referred to as the +X, −X, +Y and −Y orientations), and by combining different bend orientations, in intermediate orientations as well. Continuous positioning may be implemented using similar articulation structures by partially inflating or deflating balloons or groups of balloons.

System 10 may also be configured to provide catheter 12 with any of a plurality of discrete alternative total axial lengths. As with the bend capabilities, such length actuation may also be implemented by inflating balloons of a balloon array structure. To provide articulation with the simple balloon array structures described herein, each actuation may be implemented as a combination of discrete, predetermined actuation increments (optionally together with one or more partial or modulated actuation) but may more often be provided using modulated or partial inflation of balloons.

Figure 2:
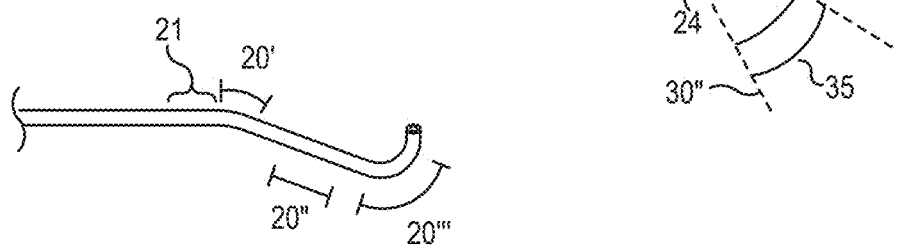
FIG. 2 schematically illustrates an alternative distal structure having a plurality of articulatable sub-regions or segments so as to provide a desired total number of degrees of freedom and range of movement.

Referring now to FIGS. 1-1 and 2, embodiments of articulation system 10 will move the distal end 24 of catheter 12 toward a desired position and/or orientation in a workspace relative to a base portion 21, with the base portion often being adjacent to and proximal of actuated portion 20. Note that such articulation may be relatively (or even completely) independent of any bending of catheter body 12 proximal of base portion 21. The location and orientation of proximal base 21 (relative to handle 14 or to another convenient fixed or movable reference frame) may be identified, for example, by including known catheter position and/or orientation identification systems in system 10, by including radiopaque or other high-contrast markers and associated imaging and position and/or orientation identifying image processing software in system 10, by including a flexible body state sensor system along the proximal portion of catheter body 12, by foregoing any flexible length of catheter body 12 between proximal handle 14 and actuated portion 20, or the like. A variety of different degrees of freedom may be provided by actuated portion 20. Exemplary embodiments of articulation system 10 may allow, for example, distal end 24 to be moved with 2 degrees of freedom, 3 degrees of freedom, 4 degrees of freedom, 5 degrees of freedom, or 6 degrees of freedom relative to base portion 21. The number of kinematic degrees of freedom of articulated portion 20 may be much higher in some embodiments, particularly when a number of different alternative subsets of the balloon array could potentially be in different inflation states to give the same resulting catheter tip and/or tool position and orientation.

Note that the elongate catheter body 12 along and beyond actuated portion 20 may (and often should) remain flexible before, during, and after articulation, so as to avoid inadvertently applying lateral and/or axial forces to surrounding tissues that are beyond a safe threshold. Nonetheless, embodiments of the systems described herein may locally and controllable increase a stiffness of one or more axial portions of catheter body 12, along actuated portion 20, proximal of actuated portion 20, and/or distal of actuated portion 20. Such selective stiffening of the catheter body may be implemented with or without active articulation capabilities, may extend along one or more axial portion of catheter body 12, and may alter which portions are stiffened and which are more flexible in response to commands from the user, sensor input (optionally indicating axial movement of the catheter), or the like.

As shown in FIG. 2, actuated portion 20 may comprise an axial series of 2 or more (and preferably at least 3) actuatable sub-portions or segments 20', 20'', 20''', with the segments optionally being adjacent to each other, or alternatively separated by relatively short (less than 10 diameters) and/or relatively stiff intermediate portions of catheter 12. Each sub-portion or segment may have an associated actuation array, with the arrays working together to provide the desired overall catheter shape and degrees of freedom to the tip or tool. At least 2 of the sub-portions may employ similar articulation components (such as similar balloon arrays, similar structural backbone portions, similar valve systems, and/or similar software). Commonality may include the use of corresponding actuation balloon arrays, but optionally with the characteristics of the individual actuation balloons of the different arrays and the spacing between the locations of the arrays varying for any distal tapering of the catheter body. There may be advantages to the use of differentiated articulation components, for example, with proximal and distal sub portions, 20', 20''' having similar structures that are configured to allow selective lateral bending with at least two degrees of freedom, and intermediate portion 20'' being configured to allow variable axial elongation. In many embodiments, however, at least two (and preferably all) segments are substantially continuous and share common components and geometries, with the different segments having separate fluid channels and being separately articulatable but each optionally providing similar movement capabilities.

For those elongate flexible articulated structures described herein that include a plurality of axial segments, the systems will often determine and implement each commanded articulation of a particular segment as a single consistent articulation toward a desired segment shape state that is distributed along that segment. In some exemplary embodiments, the nominal or resting segment shape state may be constrained to a 3 DOF space (such as by continuous combinations of two transverse lateral bending orientations and an axial (elongation) orientation in an X-Y-Z work space). In some of the exemplary embodiments described herein (including at least some of the helical extension/contraction embodiments), lateral bends along a segment may be at least approximately planar when the segment is in or near a design axial length configuration (such as at or near the middle of the axial or Z range of motion), but may exhibit a slight but increasing off-plane twisting curvature as the segment moves away from that design configuration (such as near the proximal and/or distal ends of the axial range of motion). The off-plane bending may be repeatably accounted for kinematically by determining the changes in lateral orientation of eccentric balloons resulting from winding and unwinding of helical structures supporting those balloons when the helical structures increase and decrease in axial length. For example, a segment may be commanded (as part of an overall desired pose or movement) to bend in a −Y orientation with a 20 degree bend angle. If the bend is to occur at a design axial length (such as at the middle of the axial range of motion), and assuming balloons (or opposed balloon pairs) at 4 axial bend locations can be used to provide the commanded bend, the balloons (or balloon pairs) may each be inflated or deflated to bend the segment by about 5 degrees (thereby providing a total bend of 5*4 or 20 degrees) in the −Y orientation. If the same bend is to be combined with axial lengthening of the segment to the end of its axial range of motion, the processor may determine that the segment may exhibit some twist (say 2 degrees) so that there would be a slight +X component to the commanded bend, so that the processor may compensate for the twist by commanding a corresponding −X bend component, or by otherwise compensating in the command for another segment of the flexible body.

Figure 3:
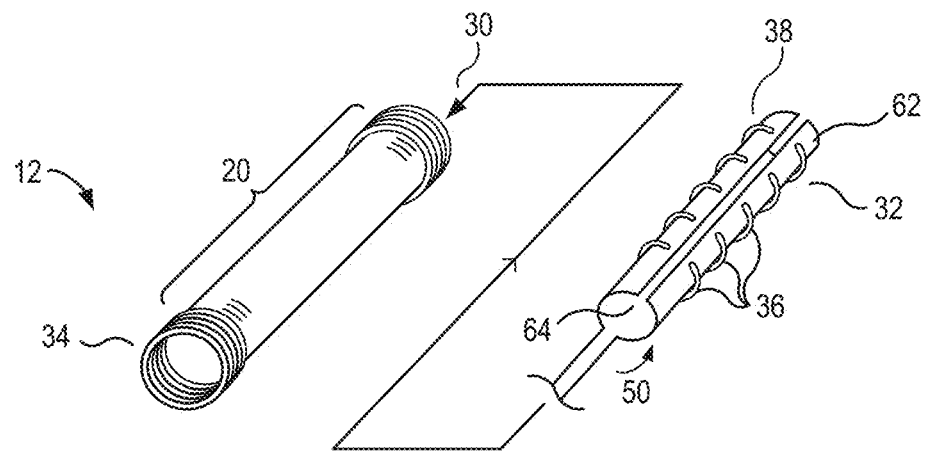
FIG. 3 is a simplified exploded perspective view showing a balloon array that can be formed in a substantially planar configuration and rolled into a cylindrical configuration, and which can be mounted coaxially to a helical coil or other skeleton framework for use in the catheter of the system of FIGS. 1 and 2.
Figure 5:
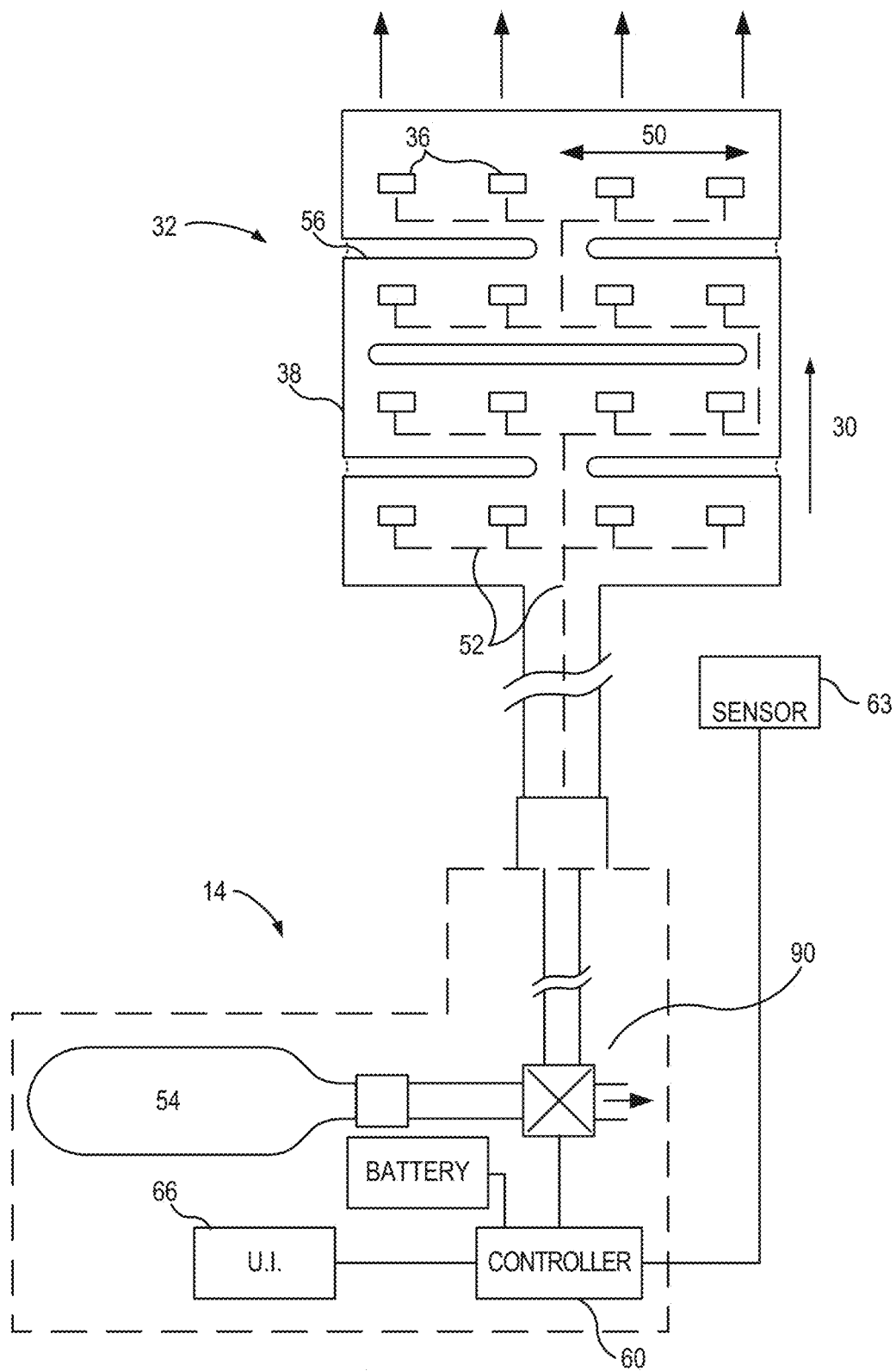
FIG. 5 schematically illustrates components for use in the catheter system of FIG. 1, including the balloon array, inflation fluid source, fluid control system, and processor.

Referring to FIGS. 3 and 5, catheter body 12 of system 10 includes an actuation array structure 32 mounted to a structural skeleton (here in the form of a helical coil 34). Exemplary balloon array 32 includes fluid expandable structures or balloons 36 distributed at balloon locations along a flexible substrate 38 so as to define an M×N array, in which M is an integer number of balloons distributed about a circumference 50 of catheter 12 at a given location along axis 30, and N represents an integer number of axial locations along catheter 12 having actuation balloons. Circumferential and axial spacing of the array element locations will generally be known, and will preferably be regular. This first exemplary actuation array includes a 4×4 array for a total of 16 balloons; alternative arrays may be from 1×2 arrays for a total of 2 balloons to 8×200 arrays for a total of 1600 balloons (or beyond), more typically having from 3×3 to 6×20 arrays. While balloon arrays of 1×N may be provided (particularly on systems that rely on rotation of the catheter body to orient a bend), M will more typically be 2 or more, more often being from 3 to 8, and preferably being 3 or 4. Similarly, while balloon arrays of M×1 may be provided to allow imposition of a single bend increment at a particular location in any of a number of different desired lateral orientations, array 32 will more typically have an N of from 2 to 200, often being from 3 to 20 or 3 to 100. In contraction/expansion embodiments described below, multiple arrays may be provided with similar M×N arrays mounted in opposition. Not all array locations need have inflatable balloons, and the balloons may be arranged in more complex arrangements, such as with alternating circumferential numbers of balloons along the axis, or with varying or alternating separation between balloons along the axial length of the array.

The balloons of a particular segment or that are mounted to a common substrate may be described as forming an array, with the actuation balloon array structure optionally being used as a sub-array in a multi-segment or opposed articulation system. The combined sub-arrays together may form an array of the overall device, which may also be described simply as an array or optionally an overall or combined array. Exemplary balloon arrays along a segment or sub-portion of articulated portion 20 include 1×8, 1×12, and 1×16 arrays for bending in a single direction (optionally with 2, 3, 4, or even all of the balloons of the segment in fluid communication with a single common inflation lumen so as to be inflated together) and 4×4, 4×8, and 4×12 arrays for X-Y bending (with axially aligned groups of 2-12 balloons coupled with 4 or more common lumens for articulation in the +X, −X, +Y, and −Y orientations). Exemplary arrays for each segment having the opposed extension/retraction continuous articulation structures described herein may be in the form of a 3×2N, 3×3N, 4×2N, or 4×3N balloons arrays, for example, 3×2, 3×4, 3×6, 3×8, 3×10, 3×12, 3×14, and 3×16 arrays with 6 to 48 balloons, with the 3 lateral balloon orientations separated by 120 degrees about the catheter axis. Extension balloons will often be axially interspersed with contraction balloons along each lateral orientation, with separate 3×N arrays being combined together in a 3×2N extension/contraction array for the segment, while two extension balloons may be positioned axially between each contraction balloon for 3×3N arrangements. The contraction balloons may align axially and/or be in plane with the extension balloons they oppose, though it may be advantageous in some embodiments to arrange opposed balloons offset from a planer arrangement, so that (for example) two balloons of one type balance one balloon of the other, or vice versa. The extension balloons along each orientation of the segment may share a common inflation fluid supply lumen while the contraction balloons of the segment for each orientation similarly share a common lumen (using 6 fluid supply lumens per segment for both 3×2N and 3×3N arrays). An extension/contraction catheter may have from 1 to 8 such segments along the articulated portion, more typically from 1 to 5 segments, and preferably being 2 to 4 segments. Other medical and non-medical elongate flexible articulated structures may have similar or more complex balloon articulation arrays.

As can be seen in FIGS. 3, 4A, 4B, and 4C, the skeleton will often (though not always) include an axial series of loops 42. When the loops are included in a helical coil 34, the coil may optionally be biased so as to urge adjacent loops 42 of the coil 34 toward each other. Such axially compressive biasing may help urge fluid out and deflate the balloons, and may by applied by other structures (inner and/or outer sheath(s), pull wires, etc.) with or without helical compression. Axial engagement between adjacent loops (directly, or with balloon walls or other material of the array between loops) can also allow compressive axial forces to be transmitted relatively rigidly when the balloons are not inflated. When a particular balloon is fully inflated, axial compression may be transmitted between adjacent loops by the fully inflated balloon wall material and by the fluid within the balloons. Where the balloon walls are non-compliant, the inflated balloons may transfer these forces relatively rigidly, though with some flexing of the balloon wall material adjacent the balloon/skeleton interface. Rigid or semi-rigid interface structures which distribute axial loads across a broader balloon interface region may limit such flexing. Axial tension forces (including those associated with axial bending) may be resisted by the biasing of the skeleton (and/or by other axial compressive structures). Alternative looped skeleton structures may be formed, for example, by cutting hypotube with an axial series of lateral incisions across a portion of the cross-section from one or more lateral orientations, braided metal or polymer elements, or the like. Non-looped skeletons may be formed using a number of alternative known rigid or flexible robotic linkage architectures, including with structures based on known soft robot structures. Suitable materials for coil 34 or other skeleton structures may comprise metals such as stainless steel, spring steel, superelastic or shape-memory alloys such as Nitinol™ alloys, polymers, fiber-reinforced polymers, high-density or ultrahigh-density polymers, or the like.

When loops are included in the skeleton, actuation array 32 can be mounted to the skeleton with at least some of the balloons 36 positioned between two adjacent associated loops 42, such as between the loops of coil 34. Referring now to FIG. 4C, an exemplary deflated balloon 36i is located between a proximally adjacent loop 42i and a distally adjacent loop 42ii, with a first surface region of the balloon engaging a distally oriented surface of proximal loop 34i, and a second surface region of the balloon engaging a proximally oriented surface of distal loop 42ii. The walls of deflated balloon 36i have some thickness, and the proximal and distal surfaces of adjacent loops 42i and 42ii maintain a non-zero axial deflated offset 41 between the loops. Axial compression forces can be transferred from the loops through the solid balloon walls. Alternative skeletal structures may allow the loops to engage directly against each other so as to have a deflated offset of zero and directly transmit axial compressive force, for example by including balloon receptacles or one or more axial protrusions extending from one or both loops circumferentially or radially beyond the balloon and any adjacent substrate structure. Regardless, full inflation of the balloon will typically increase the separation between the adjacent loops to a larger full inflation offset 41'. The simplified lateral cross-sections of FIGS. 4B, 4C, and 4D schematically show a direct interface engagement between a uniform thickness thin-walled balloon and a round helical coil loop. Such an interface may result in relatively limited area of the balloon wall engaging the coil and associated deformation under axial loading. Alternative balloon-engaging surface shapes along the coils (often including locally increased convex radii, locally flattened surfaces, and/or local concave balloon receptacles) and/or along the coil-engaging surfaces of the balloon (such as by locally thickening the balloon wall to spread the engagement area), and/or providing load-spreading bodies between the balloons and the coils may add axial stiffness. A variety of other modifications to the balloons and balloon/coil interfaces may also be beneficial, including adhesive bonding of the balloons to the adjacent coils, including folds or material so as to inhibit balloon migration, and the like.

Inflation of a balloon can alter the geometry along catheter body 12, for example, by increasing separation between loops of a helical coil so as to bend axis 30 of catheter 12. As can be understood with reference to FIGS. 1B, 1C and 4-4C, selectively inflating an eccentric subset of the balloons can variably alter lateral deflection of the catheter axis. As can be understood with reference to FIGS. 1A, 4, and 4D, inflation of all (or an axisymmetric subset) of the balloons may increase an axial length of the catheter structure. Inflating subsets of the balloons that have a combination of differing lateral orientations and axial positions can provide a broad range of potential locations and orientations of the catheter distal tip 26, and/or of one or more other locations along the catheter body (such as where a tool is mounted).

Some or all of the material of substrate 38 included in actuation array 32 will often be relatively inelastic. It may, however, be desirable to allow the skeleton and overall catheter to flex and/or elongate axially with inflation of the balloons or under environmental forces. Hence, array 32 may have cutouts 56 so as to allow the balloon array to move axially with the skeleton during bending and elongation. The array structure could alternatively (or in addition) be configured for such articulation by having a serpentine configuration or a helical coiled configuration. Balloons 36 of array 32 may include non-compliant balloon wall materials, with the balloon wall materials optionally being formed integrally from material of the substrate or separately. Note that elastic layers or other structures may be included in the substrate for use in valves and the like, and that some alternative balloons may include elastic and/or semi-compliant materials.

Figure 4A:
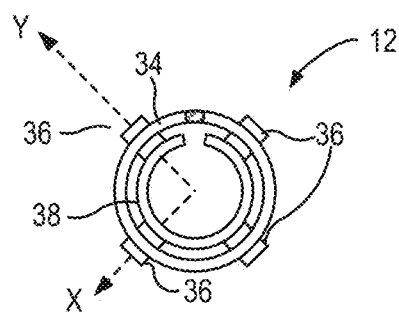
FIGS. 4A and 4B are a simplified cross-section and a simplified transverse cross-section, respectively, of an articulatable catheter for use in the system of FIG. 1, shown here with the balloons of the array in an uninflated, small axial profile configuration and between loops of the coil.
Figure 4B:
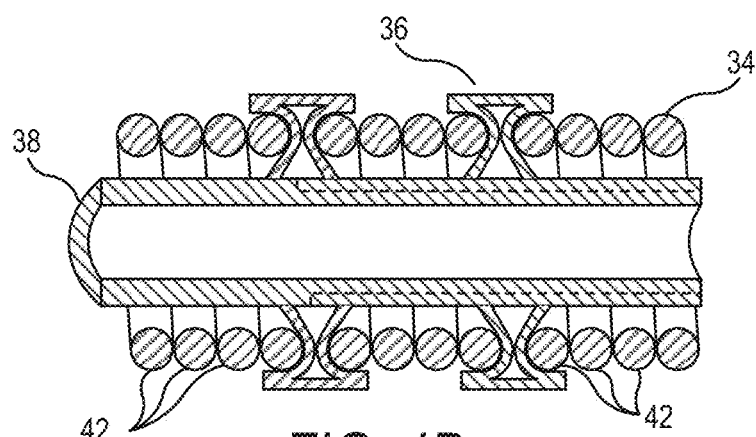
Figure 4C:
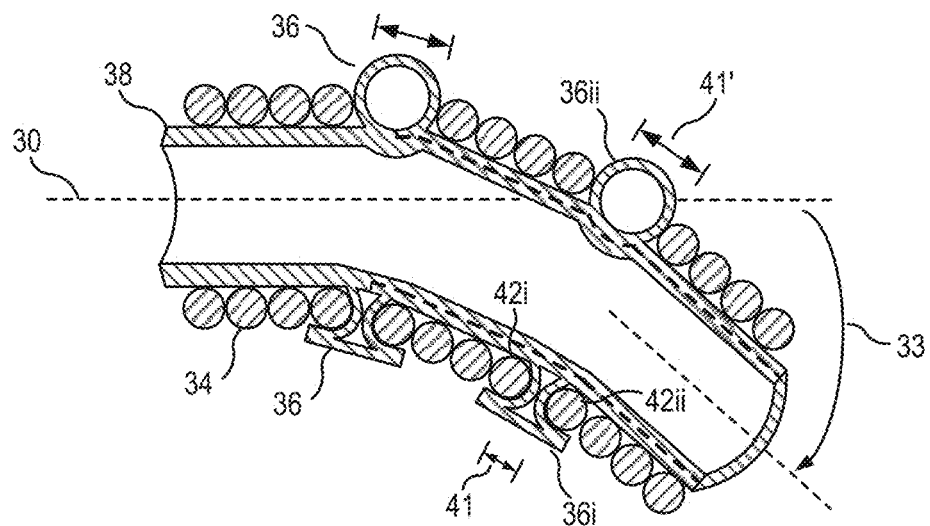
FIG. 4C is a simplified transverse cross-section of the articulatable catheter of FIGS. 4A and 4B, with a plurality of axially aligned balloons along one side of the articulatable region of the catheter inflated so that the catheter is in a laterally deflected state.
Figure 4D:
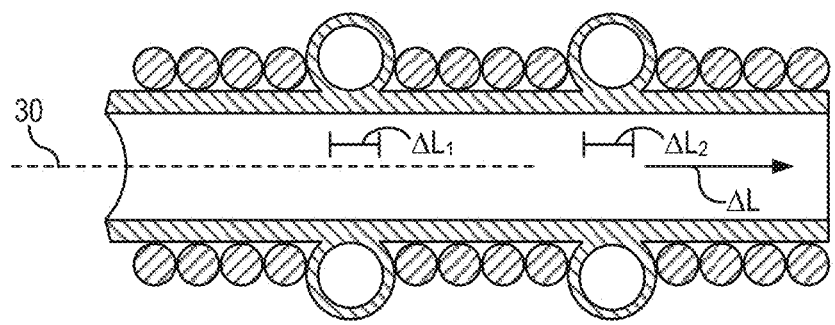
FIG. 4D is a simplified transverse cross-section of the articulatable catheter of FIG. 4, with a plurality of laterally opposed balloons inflated so that the catheter is in an axially elongated state.

Referring to FIGS. 3, 4A, and 5, substrate 38 of array 32 is laterally flexible so that the array can be rolled or otherwise assume a cylindrical configuration when in use. The cylindrical array may be coaxially mounted to (such as being inserted into or radially outwardly surrounding) the helical coil 34 or other structural backbone of the catheter. The cylindrical configuration of the array will generally have a diameter that is equal to or less than an outer diameter of the catheter. The opposed lateral edges of substrate 38 may be separated by a gap as shown, may contact each other, or may overlap. Contacting or overlapping edges may be affixed together (optionally so as to help seal the catheter against radial fluid flow) or may accommodate relative motion (so as to facilitate axil flexing). In some embodiments, lateral rolling or flexing of the substrate to form the cylindrical configuration may be uniform (so as to provide a continuous lateral curve along the major surfaces), while in other embodiments intermittent axial bend regions of the substrate may be separated by axially elongate relatively flat regions of the substrate so that a cylindrical shape is approximated by a prism-like arrangement (optionally so as to limit bending of the substrate along balloons, valves, or other array components).

It will often (though not always) be advantageous to form and/or assemble one or more components of the array structure in a flat, substantially planar configuration (and optionally in a linear configuration as described below). This may facilitate, for example, partial or final formation of balloons 36 on substrate 38, or alternatively, attachment of pre-formed balloons to the substrate. The flat configuration of the substrate may also facilitate the use of known extrusion or microfluidic channel fabrication techniques to provide fluid communication channels 52 so as to selectively couple the balloons with a fluid inflation fluid source or reservoir 54, and the like. Still further advantages of the flat configuration of the substrate may include the use of electrical circuit printing techniques to fabricate electrical traces and other circuit components, automated 3-D printing techniques (including additive and/or removal techniques) for forming valves, balloons, channels, or other fluid components that will be supported by substrate 38, and the like. When the substrate is in a rolled, tubular, or flat planar configuration, the substrate will typically have a first major surface 62 adjacent balloons 36, and a second major surface 64 opposite the first major surface (with first major surface 62 optionally being a radially inner or outer surface and second major surface 64 being a radially outer or inner surface, respectively, in the cylindrical configuration). To facilitate flexing substrate 38 and array 32 into the rolled configuration, relief cuts or channels may be formed extending into the substrate from the first and/or second major surfaces, or living hinge regions may otherwise be provided between relatively more rigid portions of the substrate. To further avoid deformation of the substrate adjacent any valves or other sensitive structures, local stiffening reinforcement material may be added, and/or relief cuts or apertures may be formed partially surrounding the valves. In some embodiments, at least a portion of the array components may be formed or assembled with the substrate at least partially in a cylindrical configuration, such as by bonding layers of the substrate together while the substrate is at least locally curved, forming at least one layer of the substrate as a tube, selectively forming cuts in the substrate (optionally with a femtosecond, picosecond, or other laser) to form fluid, circuit, or other components or allow for axial flexing and elongation (analogous to cutting a stent to allow for axial flexing and radial expansion) and/or to form at least some of the channels, and bonding the layers together after cutting.

Figure 6:
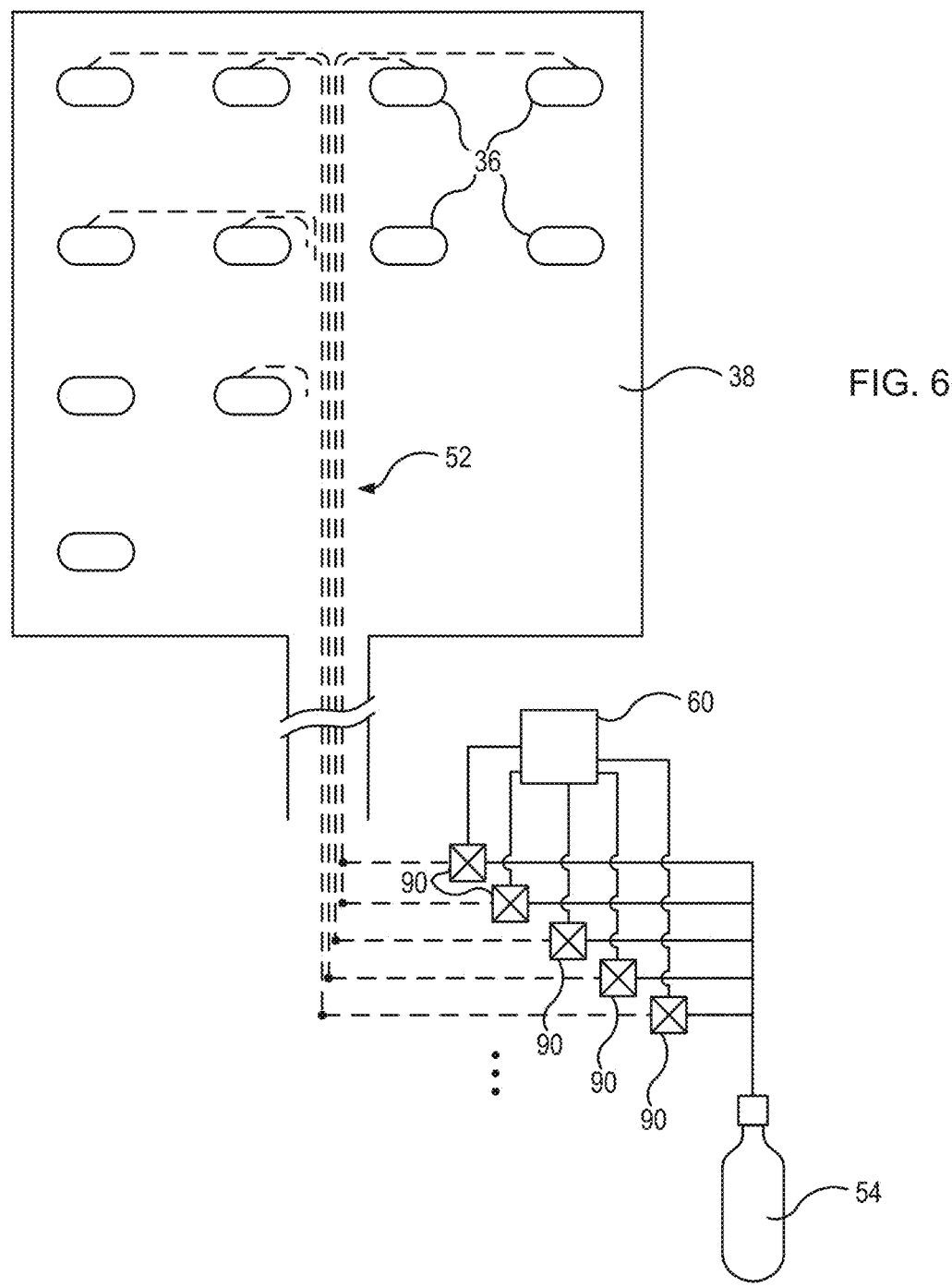
FIG. 6 is a simplified schematic of an alternative balloon array and fluid control system, in which a plurality of valves coupled with the proximal end of the catheter can be used to direct fluid to any of a plurality of channels of the array and thereby selectably determine a subset of balloons to be expanded.

As can be understood with reference to FIGS. 5 and 6, substrate 38 of array 32 may include one or more layers of flexible substrate material. The substrate layers may comprise known flexible and/or rigid microfluidic substrate materials, such as polydimethylsiloxane (PDMS), polyimide (PI), polyethylene (PE) and other polyolefins, polystyrene (PS), polyethylene terephthalate (PET), polypropylene (PP), polycarbonate (PC), nanocomposite polymer materials, glass, silicon, cyclic olefin copolymer (COC), polymethyl methacrylate (PMMA), polyetheretherketone (PEEK), polyester, polyurethane (PU), and/or the like. These and still further known materials may be included in other components of actuation array 32, including known polymers for use in balloons (which will often include PET, PI, PE, polyether block amide (PEBA) polymers such as PEBAX™ polymers, nylons, urethanes, polyvinyl chloride (PVC), thermoplastics, and/or the like for non-compliant balloons; or silicone, polyurethane, semi-elastic nylons or other polymers, latex, and/or the like for compliant or semi-compliant balloons). Additional polymers than may be included in the substrate assembly may include valve actuation elements (optionally including shape memory alloy structures or foils; phase-change actuator materials such as paraffin or other wax, electrical field sensitive hydrogels, bimetallic actuators, piezoelectric structures, dielectric elastomer actuator (DEA) materials, or the like). Hence, while some embodiments may employ homogenous materials for actuation array 32, many arrays and substrate may instead be heterogeneous.

Fortunately, techniques for forming and assembling the components for actuation array 32 may be derived from a number of recent (and relatively widely-reported) technologies. Suitable techniques for fabricating channels in substrate layer materials may include laser micromachining (optionally using femtosecond or picosecond lasers), photolithography techniques such as dry resist technologies, embossing (including hot roller embossing), casting or molding, xerographic technologies, microthermoforming, stereolithography, 3-D printing, and/or the like. Suitable 3-D printing technologies that may be used to form circuitry, valves, sensors, and the like may include stereolithography, digital light processing, laser sintering or melting, fused deposition modeling, inkjet printing, selective deposition lamination, electron beam melting, or the like. Assembly of the components of actuation array 32 may make use of thermal or adhesive bonding between layers and other components, though laser, ultrasound, or other welding techniques; microfasteners, or the like may also be used. Electrical element fabrication of conductive traces, actuation, signal processor, and/or sensor components carried by substrate 38 may, for example, use ink-jet or photolithography techniques, 3-D printing, chemical vapor deposition (CVD) and/or more specific variants such as initiated chemical vapor deposition (iCVD), robotic microassembly techniques, or the like, with the electrical traces and other components often comprising inks and other materials containing metals (such as silver, copper, or gold) carbon, or other conductors. Many suitable fabrication and assembly techniques have been developed during development of microfluidic lab-on-a-chip or lab-on-a-foil applications. Techniques for fabricating medical balloons are well developed, and may optionally be modified to take advantage of known high-volume production techniques (optionally including those developed for fabricating bubble wrap, for corrugating extruded tubing, and the like). Note that while some embodiments of the actuation array structures described herein may employ fluid channels sufficiently small for accurately handling of picoliter or nanoliter fluid quantities, other embodiments will include channels and balloons or other fluid-expandable bodies that utilize much larger flows so as to provide desirable actuation response times. Balloons having at least partially flexible balloon walls may provide particular advantages for the systems described herein, but alternative rigid fluid expandable bodies such as those employing pistons or other positive displacement expansion structures may also find use in some embodiments.

The structures of balloons 36 as included in actuation array 32 may be formed of material integral with other components of the array, or may be formed separately and attached to the array. Balloons 36 may be formed from or attached to a first sheet of substrate material that can be bonded or otherwise affixed to another substrate layer or layers. The material of the balloon layer may optionally cover portions of the channels directly, or may be aligned with apertures that open through an intermediate substrate layer surface between the channels and the balloons. Alternative methods for fabricating individual balloons are well known, and the formed balloons may be affixed to the substrate 38 by adhesive bonding. Balloon shapes may comprise relatively simple cylinders or may be somewhat tailored to taper to follow an expanded offset between loops of a coil, to curve with the cylindrical substrate and/or to engage interface surfaces of the skeleton over a broader surface area and thereby distribute actuation and environmental loads. Effective diameters of the balloons in the array may range from about 0.003 mm to as much as about 2 cm (or more), more typically being in a range from about 0.3 mm to about 2 mm or 5 mm, with the balloon lengths often being from about 2 to about 15 times the diameter. Typical balloon wall thicknesses may range from about 0.0002 mm to about 0.004 mm (with some balloon wall thicknesses being between 0.0002 mm and 0.020 mm), and full inflation pressures in the balloons may be from about 0.2 to about 40 atm, more typically being in a range from about 0.4 to about 30 atm, and in some embodiments being in a range from about 10 to about 30 atm, with high-pressure embodiments operating at pressures in a range as high as 20-45 atm and optionally having burst pressures of over 50 atm.

Referring now to FIG. 5, balloons 36 will generally be inflated using a fluid supply system that includes a fluid source 54 (shown here as a pressurized single-use cartridge)

and one or more valves 90. At least some of the valves 90 may be incorporated into the balloon array substrate, with the valves optionally being actuated using circuitry printed on one or more layers of substrate 38. With or without substrate-mounted valves that can be used within a patient body, at least some of the valves may be mounted to housing 14, or otherwise coupled to the proximal end of catheter 12. Valves 90 will preferably be coupled to channels 52 so as to allow the fluid system to selectively inflate any of a plurality of alternative individual balloons or subsets of balloons 36 included in actuation array 32, under the direction of a processor 60. Hence, processor 60 will often be coupled to valves 90 via conductors, the conductors here optionally including flex circuit traces on substrate 38.

Referring still to FIG. 5, fluid source 54 may optionally comprise a separate fluid reservoir and a pump for pressurizing fluid from the reservoir, but will often include a simple tank or cartridge containing a pressurized fluid, the fluid optionally being a gas or a gas-liquid mixture. The cartridge will often maintain the fluid at a supply pressure at or above a full inflation pressure range of balloons 36, with the cartridge optionally being gently heated by a resistive heater or the like (not shown) in housing 14 so as to maintain the supply pressure within a desired range in the cartridge during use. Supply pressures will typically exceed balloon inflation pressures sufficiently to provide balloon inflation times within a target threshold given the pressure loss through channels 52 and valves 90, with typical supply pressures being between 10 and 210 atm, and more typically being between 20 and 60 atm. Suitable fluids may include known medical pressurized gases such as carbon dioxide, nitrogen, oxygen, nitrous oxide, air, known industrial and cryogenic gasses such as helium and/or other inert or noble gasses, refrigerant gases including fluorocarbons, and the like. Note that the pressurized fluid in the canister can be directed via channels 52 into balloons 36 for inflation, or the fluid from the canister (often at least partially a gas) may alternatively be used to pressurize a fluid reservoir (often containing or comprising a benign biocompatible liquid such as water or saline) so that the balloon inflation fluid is different than that contained in the cartridge. Where a pressurized liquid or gas/liquid mixture flows distally along the catheter body, enthalpy of vaporization of the liquid in or adjacent to channels 52, balloons 36, or other tissue treatment tools carried on the catheter body (such as a tissue dilation balloon, cryogenic treatment surface, or tissue electrode) may be used to therapeutically cool tissue. In other embodiments, despite the use of fluids which are used as refrigerants within the body, no therapeutic cooling may be provided. The cartridge may optionally be refillable, but will often instead have a frangible seal so as to limit re-use.

As the individual balloons may have inflated volumes that are quite small, cartridges that are suitable for including in a hand-held housing can allow more than a hundred, optionally being more than a thousand, and in many cases more than ten thousand or even a hundred thousand individual balloon inflations, despite the cartridge containing less than 10 ounces of fluid, often less than 5 ounces, in most cases less than 3 ounces, and ideally less than 1 ounce. Note also that a number of alternative fluid sources may be used instead of or with a cartridge, including one or more positive displacement pumps (optionally such as simple syringe pumps), a peristaltic or rotary pump, any of a variety of microfluidic pressure sources (such as wax or other phase-change devices actuated by electrical or light energy and/or integrated into substrate 38), or the like. Some embodiments may employ a series of dedicated syringe or other positive displacement pumps coupled with at least some of the balloons by channels of the substrate, and/or by flexible tubing.

Referring still to FIG. 5, processor 60 can facilitate inflation of an appropriate subset of balloons 36 of actuation array 32 so as to produce a desired articulation. Such processor-derived articulation can significantly enhance effective operative coupling of the input 18 to the actuated portion 20 of catheter body 12, making it much easier for the user to generate a desired movement in a desired direction or to assume a desired shape. Suitable correlations between input commands and output movements have been well developed for teleoperated systems with rigid driven linkages. For the elongate flexible catheters and other bodies used in the systems described herein, it will often be advantageous for the processor to select a subset of balloons for inflation based on a movement command entered into a user interface 66 (and particularly input 18 of user interface 66), and on a spatial relationship between actuated portion 20 of catheter 12 and one or more component of the user interface. A number of differing correlations may be helpful, including orientational correlation, displacement correlation, and the like. Along with an input, user interface 66 may include a display showing actuated portion 20 of catheter body 12, and sensor 63 may provide signals to processor 60 regarding the orientation and/or location of proximal base 21. Where the relationship between the input, display, and sensor are known (such as when they are all mounted to proximal housing 14 or some other common base), these signals may allow derivation of a transformation between a user interface coordinate system and a base coordinate system of actuated portion 20. Alternative systems may sense or otherwise identify the relationships between the sensor coordinate system, the display coordinate system, and/or the input coordinate system so that movements of the input result in catheter movement, as shown in the display. Where the sensor comprises an image processor coupled to a remote imaging system (such as a fluoroscopy, MRI, or ultrasound system), high-contrast marker systems can be included in proximal base 21 to facilitate unambiguous determination of the base position and orientation. A battery or other power source (such as a fuel cell or the like) may be included in housing 14 and coupled to processor 60, with the housing and catheter optionally being used as a handheld unit free of any mechanical tether during at least a portion of the procedure. Nonetheless, it should be noted that processor 60 and/or sensor 63 may be wirelessly coupled or even tethered together (and/or to other components such as a separate display of user interface 66, an external power supply or fluid source, or the like).

Regarding processor 60, sensor 63, user interface 66, and the other data processing components of system 10, it should be understood that the specific data processing architectures described herein are merely examples, and that a variety of alternatives, adaptations, and embodiments may be employed. The processor, sensor, and user interface will, taken together, typically include both data processing hardware and software, with the hardware including an input (such as a joystick or the like that is movable relative to housing 14 or some other input base in at least 2 dimensions), an output (such as a medical image display screen), an image-acquisition device or other sensor, and one or more processor. These components are included in a processor system capable of performing the image processing, rigid-body transformations, kinematic analysis, and matrix processing functionality described herein, along with the appropriate connectors, conductors, wireless telemetry, and the like. The processing capabilities may be centralized in a single processor board, or may be distributed among the various components so that smaller volumes of higher-level data can be transmitted. The processor(s) will often include one or more memory or storage media, and the functionality used to perform the methods described herein will often include software or firmware embodied therein. The software will typically comprise machine-readable programming code or instructions embodied in non-volatile media, and may be arranged in a wide variety of alternative code architectures, varying from a single monolithic code running on a single processor to a large number of specialized subroutines being run in parallel on a number of separate processor sub-units.

Referring now to FIG. 6, an alternative actuation array and fluid supply system are shown schematically. As in the above embodiment, balloons 36 are affixed along a major surface of substrate 38, optionally prior to rolling the substrate and mounting of the actuation array to the skeleton of the catheter body. In this embodiment, each balloon has an associated dedicated channel 52 of substrate 38, and also an associated valve 90. Processor 60 is coupled with valves 90, and by actuating a desired subset of the valves the associated subset of balloons can be inflated or deflated. In some embodiments, each valve can be associated with more than one balloon 36, so that (for example), opening of a single valve might inflate a plurality (optionally 2, 3, 4, 8, 12, or some other desired number) of balloons, such as laterally opposed balloons so as to elongate the distal portion of the catheter. In these or other embodiments, a plurality of balloons (2, 3, 4, 5, 8, 12, or another desired number) on one lateral side of the catheter could be in fluid communication with a single associated valve 90 via a common channel or multiple channels so that opening of the valve inflates the balloons and causes a multi-balloon and multi-increment bend in the axis of the catheter. Still further variations are possible. For example, in some embodiments, channels 52 may be formed at least in-part by flexible tubes affixed within an open or closed channel of substrate 38, or glued along a surface of the substrate. The tubes may comprise polymers (such as polyimide, PET, nylon, or the like), fused silica, metal, or other materials, and suitable tubing materials may be commercially available from Polymicro Technologies of Arizona, or from a variety of alternative suppliers. The channels coupled to the proximal end of the actuatable body may be assembled using stacked fluidic plates, with valves coupled to some or all of the plates. Suitable electrically actuated microvalues are commercially available from a number of suppliers. Optional embodiments of fluid supply systems for all balloon arrays described herein may have all values mounted to housing 14 or some other structure coupled to and/or proximal of) the proximal end of the elongate flexible body. Advantageously, accurately formed channels 52 (having sufficiently tight tolerance channel widths, depths, lengths, and/or bends or other features) may be fabricated using microfluidic techniques, and may be assembled with the substrate structure, so as to meter flow of the inflation fluid into and out of the balloons of all of the actuation arrays described herein.

A variety of known lab-on-a-chip and lab-on-a-foil production techniques can be used to assemble and seal the substrate layers, with many embodiments employing thermal fusion bonding, solvent bonding, welding (and particularly ultrasound welding), UV-curable adhesives, contact adhesives, nano-adhesives (including doubly cross-linked nano-adhesive or DCNA), epoxy-containing polymers (including polyglycidyl methacrylate), plasma or other surface modifications, and/or the like between layers. For high fluid pressure systems, third generation nano-adhesive techniques such as CVD deposition of less than 400 nanometer layers of DCNA materials may facilitate the use of high-strength polymer materials such as PET. Channels of such high-pressure systems may optionally be defined at least in part by PET and/or fused silica tubing (which may be supported by a substrate along some or all of the channel, and/or may be bundled together with other fused silica tubing along some or all of its length ideally in an organized array with tubing locations corresponding to the balloon locations within the balloon array, analogous to the organization of a coherent fiber optic bundle), or the like. Any valves mounted to the substrate of the balloon array may be electrically actuated using conductive traces deposited on a surface of a substrate layer prior to bonding, with an overlying layer sealing the traces in the interior of the substrate. Valve members may move when a potential is applied to an actuation material using the traces, with that material optionally comprising a shape-memory alloy, piezoelectric, an electrically actuated polymer, or the like. Still further alternative actuation materials may include phase change materials such as wax or the like, with the phase change being induced by electrical energy or optical energy (such as laser light transmitted via an optical fiber or printed pathway between layers of the substrate). In some embodiments, the actuation material and valve member may be formed using 3-D printing techniques. Multiplex circuitry may be included in, deposited on a layer of, or affixed to substrate 38 so that the number of electrical traces extending proximally along catheter body 12 may be less than the number of valves that can be actuated by those valves. The valves may take any of a wide variety of forms, and may employ (or be derived from) known valve structures such as known electrostatically-actuated elastomeric microfluidic valves, microfluidic polymer piston or free-floating gate valves, layered modular polymeric microvalves, dielectric elastomer actuator valves, shape memory alloy microvalves, hydrogel microactuator valves, integrated high-pressure fluid manipulation valves employing paraffin, and the like. Along with electrically actuated microvalves, suitable valves may be optically actuated, fluid actuated, or the like.

It should be understood that many of the valves shown herein are schematic, and that additional or more complex valves and channel systems may be included to control inflation and deflation of the balloons. One or more valves in the system may comprise gate valves (optionally normally closed, normally open or stable), so as to turn inflation fluid flow from the fluid source to at least one balloon on or off. Deflation may optionally be controlled by a separate gate valve between each balloon (or groups of balloons) and one or more deflation port of substrate 38 (the fluid from the balloon optionally exiting from the substrate to flow proximally between radially inner and outer sealed layers of the catheter) or housing 14. Alternative 2-way valves may allow i) communication between either the fluid source and the balloon (with flow from the balloon being blocked), or ii) between the balloon and the deflation outflow (with the flow from the fluid source being blocked). Still further alternatives may be employed, including a 3 way valve having both of the above modes and iii) a sealed balloon mode in which the balloon is sealed from communication with the fluid source and from the deflation outflow (with flow from the source also being closed).

Figure 7:
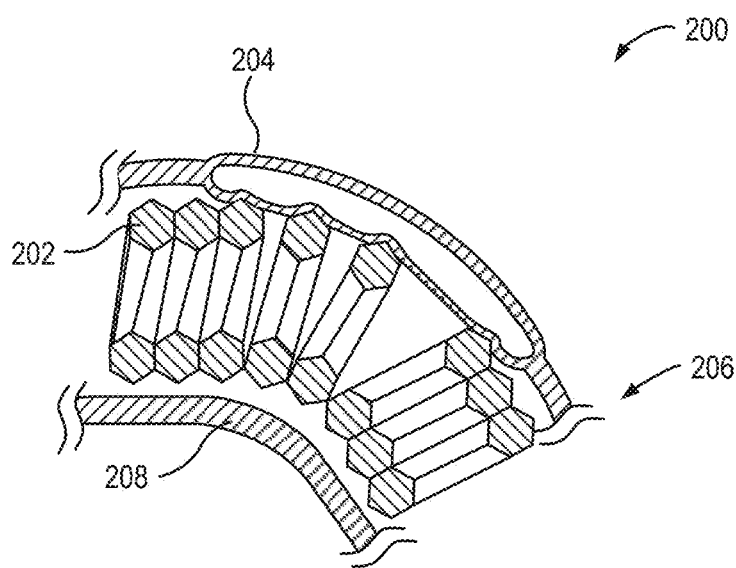
FIG. 7 is a simplified transverse cross-section of catheter wherein one or more balloons can be inflated to radially engage a plurality of loops of a helical coil so as to inhibit bending of a catheter axis.

Referring now to FIG. 7, an optional catheter structure employs an alternative balloon array structure having one or more elongate balloons 204 that each extend axially, with balloons 204 here being formed in a layered substrate 208 so that the balloons together define a balloon array 206 that can frictionally engage or latch against coils to help inhibit lateral bending of a catheter body. When deflated, the loops 202 of the helical coils can move away from (or if separated, toward) each other, allowing the catheter body to flex (and straighten). In contrast, fluid expansion of balloons 208 causes each axial balloon to radially engage a plurality of coils 202, inhibiting movement of the coils toward or away from each other so as to add axial stiffness to the catheter body. Interestingly, this can make it more difficult to bend a straight portion of the catheter, and/or can make it more difficult for a bent portion of the catheter to straighten (or otherwise alter its axial configuration). As described above, substrate 208 may be disposed between inner and outer coils so that the axially oriented balloons radially engage either (or both); or the substrate may be disposed radially outward of the coil to be engaged with the edges of the substrate affixed together so as to limit radial displacement of the balloons and promote firm radial engagement between the expanded balloon and the coil. Still further alternatives are available, including the use of semi-rigid or other radial support materials in the substrate, with or without edges affixed together. As can also be understood with reference to FIGS. 4C and 7, bend-inducing balloons may be combined with bend-inhibiting balloons by including both types of balloons on a single substrate (optionally on opposed sides) or on separate substrates. Advantageously, the substrate, balloon, and fluid supply and control structures of these bend-change-inhibiting balloon arrays may include the characteristics described above for the corresponding structures of the balloon articulation systems.

Figure 8:
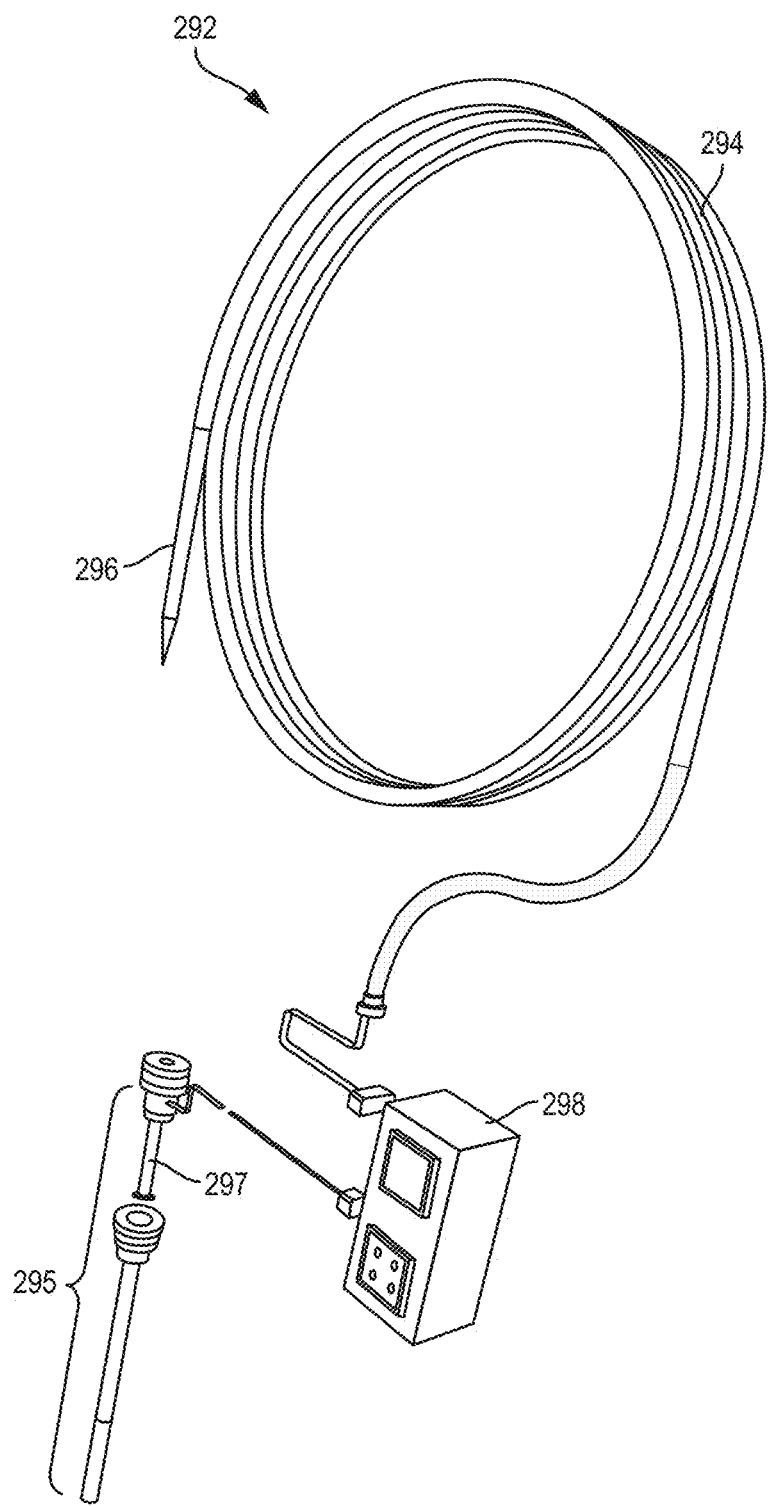
FIG. 8 schematically illustrates a catheter articulation system in which an input of the system is incorporated with an introducer sheath.

Referring now to FIG. 8, components of an exemplary catheter articulation system 292 can be seen, with these components generally being suitable for use in catheter system 1 of FIG. 1. In this embodiment, a catheter 294 has a distal articulated portion 296, with the articulated portion optionally including axially separate articulation sub-portions or segments, and alternatively having a single relatively continuously articulated length. An insertion sheath/input assembly 295 is included in the system user interface, and both assembly 295 and the proximal end of catheter 294 are detachably coupleable with a proximal housing 298 using flexible cables (and quick-disconnect couplers), with the housing containing a battery, a processor, a replaceable compressed fluid cartridge, valves, and the like. Housing 298 also includes or contains additional components of the user interface, and is sized for positioning by a single hand of a user, but need not be moved during use of catheter 294. Commands to effect automated bending and elongation of distal portion 296 during use may optionally be input into the system by bending and axial insertion of input 297 relative to a proximal body of the introducer sheath, thereby employing manual movements of the user which are already familiar to physicians that employ catheter-based diagnostic and therapeutic tools.

Regarding some of the user interface components of articulation system 292, use of input 297 for controlling the articulation state of catheter 294 will be described in more detail hereinbelow. In addition to input 297, a number of additional (or alternative) user interface components may be employed. As generally indicated above, the user interface may include a housing affixed to a proximal end of catheter 294, with the housing having a joystick as described above regarding FIG. 1-1. Trackballs or touchpads may be provided in place of a joystick, and as the catheters and other structures described herein may have more than two degrees of freedom, some embodiments may include two offset joysticks, with a more proximal joystick on the handle being used to laterally deflect the catheter along a proximal X-Y segment and a more distal joystick of the same handle being used to laterally deflect the catheter along a more distal X'-Y' segment. These two deflections may be used to enter movement commands in a manner analogous to positioning of a robotic base using the first joystick and then articulating a wrist mounted to that base with the second joystick, with the joysticks providing either position or velocity control input to the catheter system. An input wheel with a surface that rolls along the axis of the housing can be used for entering axial elongation movement commands, and the housing may have a circumferential wheel that can be turned by the system user to help provide a desired alignment between an orientation of the housing relative to the lateral deflections of the catheter as seen in the remote imaging display. Still further alternative user interface systems may employ computer workstations such as those of known robotic catheter or robotic surgical systems, which may include one or more 3-D joysticks (optionally including an input allowing 4D, 5D, or even more degrees of freedom), housings mimicking those of mechanically steerable catheter systems, or the like. As seen in the embodiment of FIG. 8, still further optional components include a touchscreen (which may show a graphical representation of distal articulated portion 296 (one or more segments of which can be touch-selected and highlighted so that they articulate in response to movement of input 297), pushbuttons, or the like. Still further alternative user interface components may include voice control, gesture recognition, stereoscopic glasses, virtual reality displays, and/or the like.

Referring now to FIG. 9, selected components of an articulated portion 302 of an articulated catheter 304 can be seen in more detail. A plurality of inflated balloons 306 are offset from an axis 308 of catheter 304 along a first lateral orientation +X, so that the balloons urge corresponding pairs of axial (proximal and distal) surfaces on the loops of coil 310 apart. This urges the coil to bend away from inflated balloons 306 away from the +X orientation and toward the −X lateral orientation. Uninflated balloons 312a, 312b, and 312c are offset in the lateral −X, −Y, and +Y orientations, respectively, allowing selective inflations of differing subsets of these balloons to bend axis 308 in differing directions. Inflation of opposed balloons (such as −X and +X, or −Y and +Y, or both) may elongate coil 314 along axis 308. Note that a distal portion of coil 314 has been omitted from the drawing so that the arrangement of the balloons can be more clearly seen. This embodiment shows relatively standard offset balloon shapes, with the axes of the balloons bent to follow the coil. In this and other embodiments, a single balloon between coils may impose a bend in axis 308 in a range from 1 to 20 degrees, more typically being in a range from 2½ to 15 degrees, and often being from 6 to 13 degrees. To allow a single inflation lumen to achieve greater bend angles, 2, 3, 4, or more balloon inflation lumens or ports adjacent the balloons may be in fluid communication with a single common fluid inflation lumen.

Referring now to FIGS. 9-12, an exemplary integrated balloon array and array substrate design and fabrication process can be understood. As seen in FIGS. 9 and 10, a cylinder 318 is defined having a diameter corresponding to a helical coil axis 320 of coil 310, with the coil axis typically corresponding to the central axis of the coil wire (so that the helical axis winds around the central axis of the elongate body). Desired balloon centerlines 322 are here defined between loops of the coil. Alternative balloon centerlines may extend along the coil axis, as can be understood with other embodiments described below. A flat pattern 324 of the balloon centerlines 322 can be unwrapped from cylinder 318, with the flat pattern optionally forming a repeating pattern extending along a helical wrap of the cylinder, the helical pattern unwrap optionally being counter wound relative to coil 310 and typically having a pitch which is greater than that of the coil. As can be understood with reference to FIGS. 11 and 12, the repeated flat pattern 324 can be used to define a repeating substrate pattern 326, with the substrate pattern here including, for each balloon in this portion of the array, a balloon portion 328, a multi-lumen channel portion 330, and a connector portion 332 for connecting the balloon to the multi-lumen channel portion. The connector portions and balloons here extend from a single side of the multi-lumen channel portion; alternative embodiments may have connector portions and balloons extending from both lateral and/or circumferential sides. The loops of the substrate helix may also overlap. In other embodiments, the flat pattern (and associated substrate and multi-lumen channels) may wind in the same direction as the coil, with the balloons and channel structures optionally extending along a contiguous strip, the balloons optionally having channels along one or both axial sides of the strip and the balloons protruding radially from the strip and between the loops of the coil so that connector portions 332 may optionally be omitted. Such embodiments may benefit from a thicker and/or polymer coil. Regardless, the helical balloon array structure may facilitate lateral bending of the catheter along its axis and/or axial elongation of the catheter without kinking or damaging the substrate material along the fluid flow channels, as the substrate loops may slide relative to each other along an inner or outer surface of coil 310 (often within a sealed annular space between inner and outer sheaths bordering the inner and outer surfaces of the catheter).

Advantageously, the substrate pattern may then be formed in layers as generally described above, with at least a portion (often the majority) of each balloon being formed from sheet material in a first or balloon layer 334 (optionally by blowing at least a portion of the balloon from suitable sheet material into a balloon tool) and some or all of the channels being formed from sheet material in a second or channel layer 336. The layers can be bonded together to provide sealed fluid communication between the balloons and the other components of the fluid supply system, with the outline shapes of the balloon portions 328, connector portions 332, and channel portions being cut before bonding, after bonding, or partly before and partly after. Note that a portion of the balloon shape may be imposed on the channel layer(s) and that a plurality of channel layers may be used to facilitate fluid communication between a plurality of helically separated balloons (including balloons along a single lateral orientation of the assembled catheter) and a common fluid supply channel. Similarly, a portion (or even all) of the channel structure might alternatively be imposed on the balloon layer, so that a wide variety of architectures are possible. Formation of multiple balloons 334 and channels 330, and bonding of the layers can be performed using parallel or batch processing (with, for example, tooling to simultaneously blow some or all of the balloons for a helical balloon array of an articulation sub-portion, a laser micromachining station that cuts multiple parallel channels, simultaneous deposition of adhesive materials around multiple balloons and channels), or sequentially (with, for example, rolling tooling and/or roll-by stations for balloon blowing, laser cutting, or adhesive applying tooling), or a combination of both. The number of balloons included in a single helical substrate pattern may vary (typically being from 4 to 80, and optionally being from 4 to 32, and often being from 8 to 24). The balloons may be spaced for positioning along a single lateral catheter bending orientations, along two opposed orientations, along three orientations, along four orientations (as shown), or the like. Channel portion 330 may terminate at (or be integrated with) an interface with a multi-channel cable 334 that extends proximally along the coil (and optionally along other proximal balloon array portions formed using similar or differing repeating balloon substrate patterns). A wide variety of alternative balloon shapes and balloon fabrication techniques may be employed, including blowing a major balloon portion from a first sheet material and a minor portion from a second sheet material, and bonding the sheets surrounding the blow portions together with the bond axially oriented (as shown in FIG. 10) so that the sheets and substrate layers are oriented along a cylinder bordering the coil, or with the bond radially oriented so that the sheet material adjacent the bonds is connected to adjacent substrate by a bent connector portion or tab.

Figures 12A, 12B:
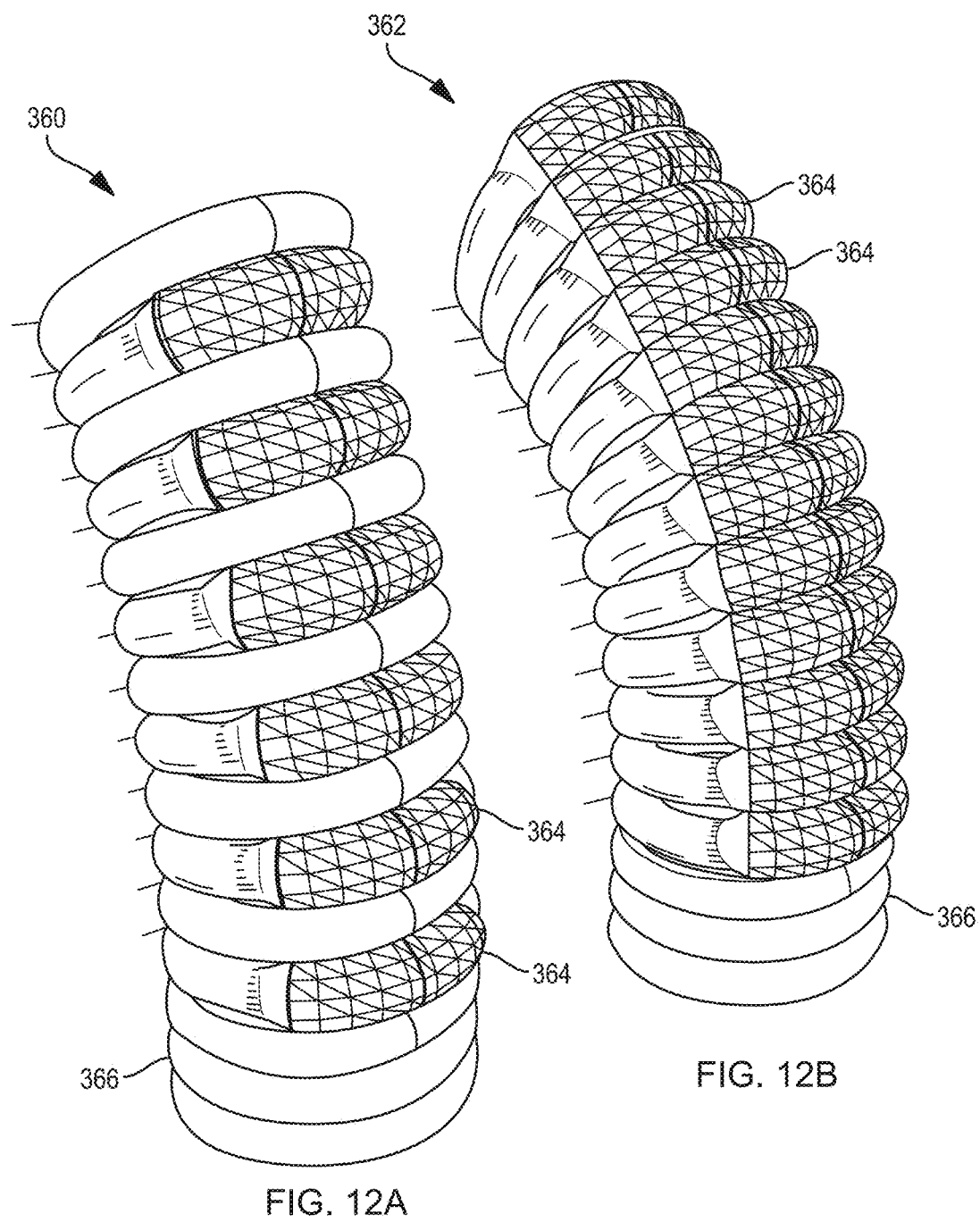
FIGS. 12A and 12B schematically illustrate balloon arrays in which the balloons are disposed over helical coil cores, and also show the effects of varying balloon inflation density on a radius of curvature of a catheter.

Referring now to FIGS. 12A and 12B, an alternative coaxial balloon/coil arrangement can be understood. In these embodiments, balloons 364 are mounted over a coil 366, with a plurality of the balloons typically being formed from a continuous tube of material that extends along the helical axis of the coil. The balloon material will generally have a diameter that varies locally, with the balloons being formed from locally larger diameter regions of the tube, and the balloons being separated by sealing engagement between the tube material and coil therein at locally smaller diameters of the tube. The variation in diameter may be formed by locally blowing the balloons outward from an initial tube diameter, by locally heat-shrinking an initial tube diameter, or both, and adhesive or heat-bonding between the tube and coil core therein may enhance sealing. In alternative embodiments, metal rings may be crimped around the tubular balloon material to affix (and optionally seal) the tube to the underlying helical coil. Some or even all of the variation in diameter of the balloon material along the coil may be imposed by the crimped rings, though selective heat shrinking and/or blowing of the balloons and/or laser thermal bonding of the balloon to the coil may be combined with the crimps to provide the desired balloon shape and sealing. Regardless, fluid communication between the inner volume of the balloon (between the balloon wall and the coil core) may be provided through a radial port to an associated lumen within the coil core. As can be understood with reference to coil assembly 360 of FIG. 11A, the balloons may have outer surface shapes similar to those described above, and may similarly be aligned along one or more lateral bending orientations. As can be understood with reference to assemblies 360 and 362 of FIGS. 12A and 12B, bend angles and radii of curvature of the catheter adjacent the balloon arrays may be determined by an axial spacing (and/or number of loops) between balloons, and/or by selective inflation of a subset of balloons (such as by inflating every other balloon aligned along a particular lateral axis, every third aligned balloon, every forth aligned balloon, and so on).

Figure 13:
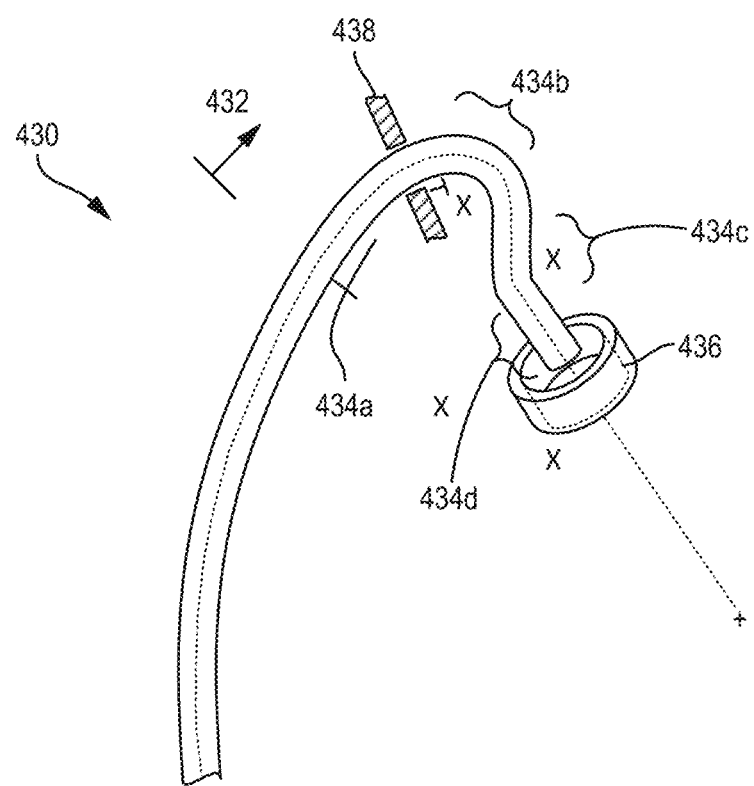
FIG. 13 schematically illustrates bending of a diagnosis or treatment delivery catheter into alignment with a target tissue by actuating a plurality of articulation sub-portions or segments of the catheter.

Referring now to FIG. 13, an exemplary catheter 430 has an articulated portion 432 that includes a plurality of axially separate articulated segments or sub-portions 434a, 434b, 434c, and 434d. Generally, the plurality of articulation segments may be configured to facilitate aligning a distal end of the catheter with a target tissue 436. Suitable articulation segments may depend on the target tissue and planned procedure. For example, in this embodiment the articulation segments are configured to accurately align a distal end of the catheter with the angle and axial location of the native valve tissue, preferably for any patient among a selected population of patients. More specifically, the catheter is configured for aligning the catheter axis at the distal end of the catheter with (and particularly parallel to) an axis of the target tissue, and (as measured along the axis of the catheter) for axially aligning the end of the catheter with the target tissue. Such alignment may be particularly beneficial, for example, for positioning a prosthetic cardiac valve (optionally an aortic valve, pulmonary valve, or the like, and particularly a mitral valve) with tissues of or adjacent a diseased native valve. Suitable catheter articulation capabilities may also, in part, depend on the access path to the target tissue. For alignment with the mitral valve, the catheter may, for example, be advanced distally into the right atrium via the superior or inferior vena cava, and may penetrate from the right atrium through the septum 438 into the left atrium. Suitable transceptal access may be accomplished using known catheter systems and techniques (though alternative septal traversing tools using the articulated structures described herein might alternatively be used). Regardless, to achieve the desired alignment with the native valve tissue, the catheter may be configured to, for example: 1) from distally of (or near) the septum, form a very roughly 90 degree bend (+/−a sufficient angle so as to accommodate varying physiologies of the patients in the population); 2) extend a distance in desired range in three dimensions, including a) apically from the septal penetration site and b) away from the plane of the septal wall at the penetration; and 3) orient the axis of the catheter at the distal end in three dimensions and into alignment with the native valve tissue.

To achieve the desired alignment, catheter 430 may optionally provide consistent multi-axis bend capabilities as well as axial elongation capabilities, either continuously along the majority of articulatable portion 432 of catheter 430, or in articulated segments at regular intervals extending therealong. Alternative approaches may employ more functionally distinguished articulation segments. When present, each segment may optionally have between 4 and 32 balloons, subsets of the balloons within that segment optionally being oriented along from 1 to 4 lateral orientations. In some embodiments, the axis bending balloons within at least one segment may all be aligned along a single bend orientation, and may be served by a single inflation lumen, often served by a modulated fluid supply that directs a controlled inflation fluid volume or pressure to the balloons of the segment to control the amount of bending in the associated orientation. Alternative single lateral bending direction segments may have multiple sets of balloons served by different lumens, as described above. For example, segments 434a and 434b may both comprise single direction bending segments, each capable of imposing up to 60 degrees of bend angle and with the former having a first, relatively large bend radius in the illustrated configuration due to every-other axial balloon being inflated, or due to inflation with a limited quantity of inflation fluid. In segment 434b, all but the distal-most four balloons may be inflated, resulting in a smaller bend radius positioned adjacent segment 434a, with a relatively straight section of the catheter distal of the bend. Segment 434c may have balloons with four different bend orientations at a relatively high axial density, here having selected transverse balloons (such as 6 +X balloons and 2 −Y balloons) inflated so as to urge the catheter to assume a shape with a first bend component away from the septal plane and a second bend component laterally away from the plane of the bends of segments 434a and 434b. Segment 434d may comprise an axial elongation segment, with opposed balloons in fluid communication with the one or more inflation fluid supply lumen of this segment. Axial positioning of the end of the catheter may thus be accurately controlled (within the range of motion of the segment) by appropriate transmission of inflation fluid. Advantageously, such specialized segments may limit the number of fluid channels (and the cost, complexity and/or size of the catheter) needed to achieve a desired number of degrees of freedom and a desired spatial resolution. It should be understood that alternative segment arrangements might be employed for delivery of a prosthetic heart valve or the like, including the use of three segments. The valve might be positioned using a three-segment system by, for example, inserting the catheter so that the septum is positioned along the middle of the three segments, ideally with the catheter traversing the septum at or near the middle of the middle segment.

Figure 14:
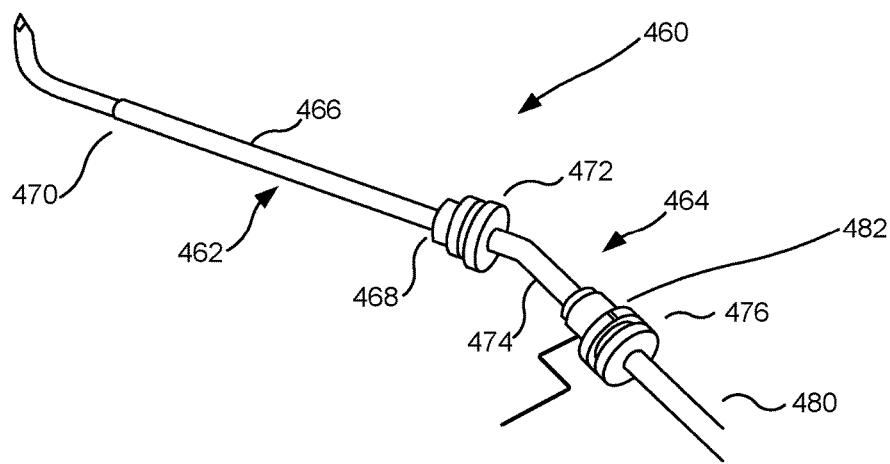
FIGS. 14 and 15 are a perspective view showing an exemplary introducer sheath/input assembly having a flexible joystick for receiving movement commands using relative movement between hands or fingers of a user, and a schematic cross-section of the sheath/input assembly, respectively.

Referring now to FIG. 14, a perspective view of an exemplary introducer sheath/input assembly for use in the systems of FIGS. 1 and 8 can be seen in more detail. Introducer/input assembly 460 generally includes an introducer sheath assembly 462 and an input assembly 464. Introducer 462 includes an elongate introducer sheath 466 having a proximal end 468 and a distal end 470 with an axial lumen extending therebetween. A proximal housing 472 of introducer 462 contains an introducer hemostasis valve. Input 464 includes a flexible joystick shaft 474 having a distal end slidably extending into the lumen of introducer housing 472, and a proximal end affixed to an input housing 476 containing an input valve. A lumen extends axially through input 464, and an articulatable catheter 480 can be advanced through both lumens of assembly 460. A cable or other data communication structure of assembly 460 transmits movement commands from the assembly to a processor of the catheter system so as to induce articulation of the catheter within the patient. More specifically, when the catheter system is in a driven articulation mode, and a clutch input 482 of introducer/input assembly 460 is actuated, movement of input housing 476 relative to sheath housing 472 induces articulation of one or more articulatable segment of catheter 480 near the distal end of the catheter, with the catheter preferably having any one or more of the articulation structures described herein. The valves within the housings of introducer/input assembly may be actuated independently to axially affix catheter 480 to introducer 462, and/or to input 464.

Figure 16:
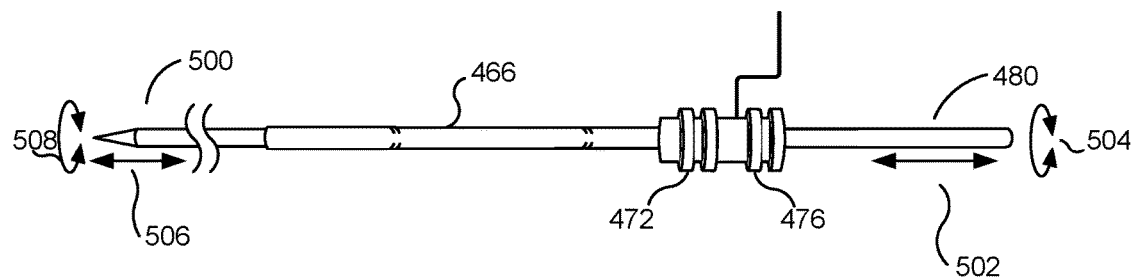
FIGS. 16 and 16A schematically illustrate use of the sheath/input assembly of FIG. 14 in a manual mode.
Figure 15:
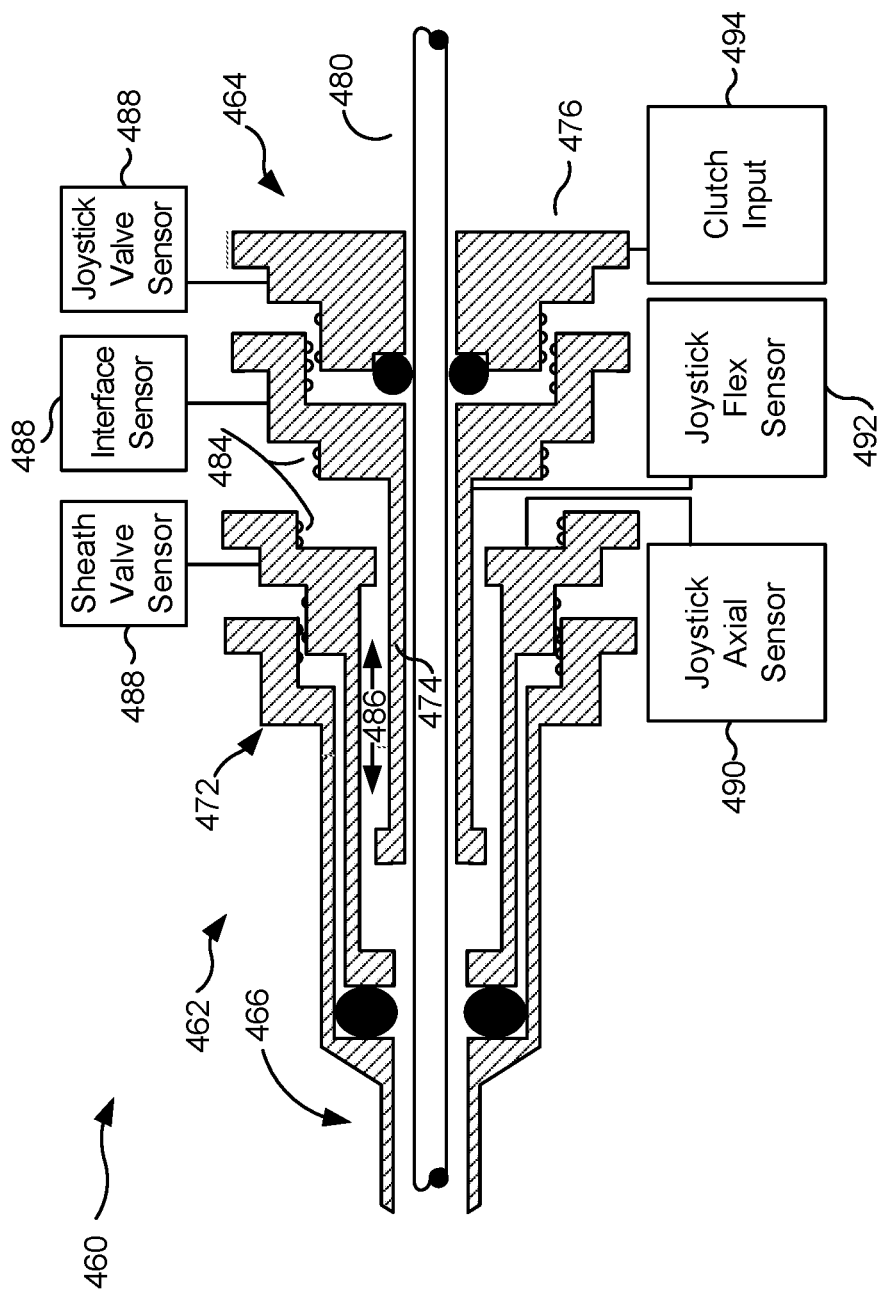
Figure 16A:
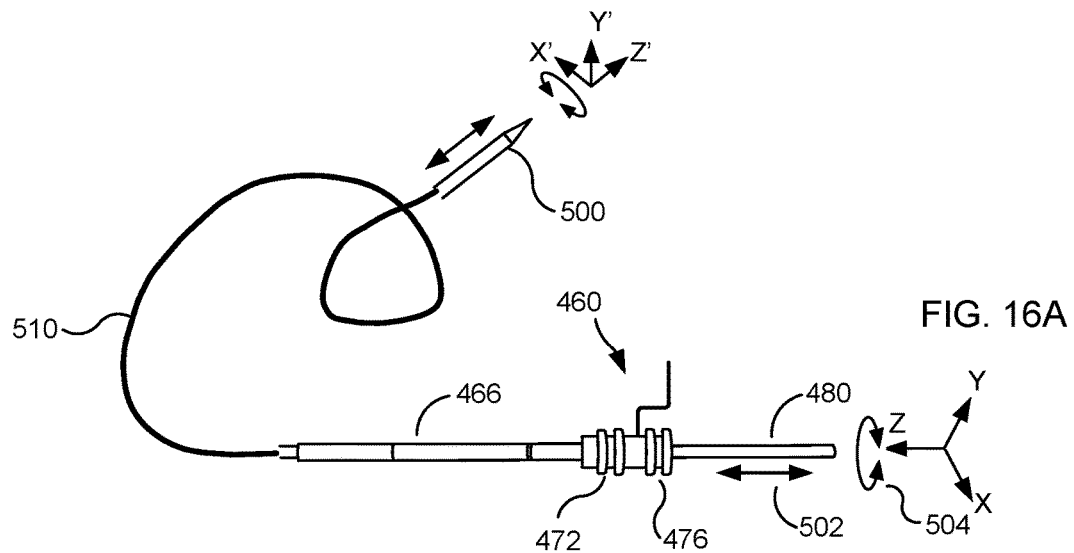

Referring now to FIGS. 1, 8, 14-16J, and Table 1, introducer/input assembly 460 can be used during operation of the catheter system in multiple different modes. Table 1 summarizes exemplary system configuration and operation of some exemplary modes, and FIG. 15 schematically illustrates components of introducer assembly 462 that can be used to help implement those modes. FIGS. 16 and 16A schematically illustrate manual movement of system components during manual manipulation of the catheter, in an exemplary manual mode. FIGS. 16B-16E schematically illustrate exemplary 3-D movement input commands and associated automated changes in articulation state of the articulated catheter. FIGS. 16F-16H schematically illustrate a combination of measured manual movement of the catheter body through the introducer and automated changes in articulation state of the articulation catheter in an exemplary follow-a-curve mode, and can also help to understand an exemplary axial elongation recovery mode. FIGS. 16I and 16J schematically illustrate measured manual axial movement and locally varying a stiffness of the catheter so as to tailor trackability/pushability of the overall catheter.

TABLE 1

|  | Manual Operation | Follow a Curved Path | 3-D Powered Position/Orientation Movement |
|---|---|---|---|
| Introducer Valve | Open | Open* | Fixed |
| Input Valve | Open | Fixed* | Open |
| Introducer/Input Interface | Fixed | Open | Open |
| Comments | Manual insertion and rotation adjacent introducer analogous to standard catheter manipulation. May use with a set distal deflection, and/or with set locally adjusted catheter stiffness. | Combines measured manual axial movement and powered lateral deflection. Path may be predefined, sensed from guidewire or lumen, or defined by catheter shape state. May start with axial elongation recovery. | Proximal catheter body is stationary relative to insertion sheath and surrounding tissue, analogous to a soft-tissue-mounted robotic manipulator base. |

Referring now to FIGS. 15 and 16, introducer/input assembly 460 can be used in a manual mode by affixing the introducer housing 472 to the input housing 476, and by opening the valves of both so that catheter 480 can rotate and slide axially through the coaxial lumens of introducer 462 and input 464. The housings can be affixed together using a releasable input/introducer interface 484, with exemplary interfaces comprising corresponding threads, a Luer lock, or the like. Flexible joystick 474 may extend into or through introducer housing 472, with the joystick being rotatable about the lumen and axially slidable within a range of movement limited by the interface 484 and slide limiting stops 486. Note that the flexible joystick may optionally slide within a rigid distal extension of introducer housing 472, allowing the system user to grasp the extension outside the patient to help inhibit movement or bending of the sheath 466 within the access site. Alternatively, the flexible joystick may be extendable distally within the flexible sheath toward or even into the patient.

The valves may comprise elastomeric valve bodies such as O-rings or the like which are axially compressed when closed (so that they are pushed radially inward into axial restraining engagement with the outer surface of the catheter) and axially released when opened (so as to or allow axial sliding of the catheter body therethrough). Hence, the valve housings may comprise threads, Luer locks, hemostat-like lockable pinch handles, or the like, and may alternatively comprise fluid inflatable or electrically powered valve actuators. When open, sliding engagement between the valve bodies and the catheter may help maintain hemostasis, and that an additional hemostatis structure (such as a duck bill valve body, a slit foam valve body, or the like) may be included along one or both lumens and/or between the flexible joystick and the surrounding introducer housing to promote hemostasis around smaller diameter guidewires, prior to insertion of the catheter, when the valves are in different configurations, etc.

As the catheter system mode and drive signals sent to inflation fluid drives or other actuation components may vary in correlation with the configurations of the introducer valve, input valve, and interface, sensors 488 may be associated with any one or more of these, with these sensors transmitting signals corresponding to the configuration of the associated structure and facilitating use of their manual reconfiguration as an input to the system processor to alter the mode of the catheter system. Regardless, in the exemplary embodiment, a plurality of sensors are used to sense movements of catheter system components of or adjacent the introducer/input assembly 460, and to transmit movement command inputs in response. For example, an axial movement command sensor 490 can be mounted to the introducer 462, input 464, and/or catheter 480 and can transmit signals corresponding to an axial displacement or movement of the input (and/or catheter) relative to the introducer. Exemplary axial sensors may comprise electrical coils, hall effect sensors, optical sensors (optionally similar to those of an optical computer mouse), or the like, and will preferably measure axial displacement of the input housing relative to the introducer housing, so that the introducer housing operates as an input base. A lateral movement command sensor 492 similarly measures lateral and/or angular displacement relative to the lumenal axis of the introducer housing. Lateral sensor 492 may be mounted to the flexible joystick, input housing, and/or catheter 480, and optionally comprises an optical Fiber Bragg Grating flex sensor or flex circuit flex sensor extending along the flexible shaft of the flexible joystick 474. Lateral sensor 492 may hence comprise relatively simple cost-effective optical fibers or other components that send optical or electrical signals to be processed using re-usable processing structures, allowing the introducer/input assembly to be single-use items and avoiding the dangers of sterilization and re-use. Lastly, a clutch input 494 may comprise a simple switch, ideally a normally off switch which operates to inhibit automated articulation in response to movement of the input structures unless a button is held down or the like.

Referring now to FIGS. 16 and 16A, operation of the catheter system in the manual mode is suitable for rapid manual movements through easily navigated portions of the lumen, and may provide tactile feedback to the system operator. Axial insertion 502 and rotation 504 of catheter 480 near the introducer sheath, and can effect corresponding axial and rotational movements 506, 508 of a distal end 500 of the catheter. However, where the catheter extends along a tortuous 3-D path 510 as shown schematically in FIG. 16A, there may be significant differences between the manual input movements and those exhibited by the distal end of the catheter. Note that this manual mode can be performed without many of the components of introducer/input assembly 460, for example, using a simple introducer prior to attachment of the input assembly or the like. Note also that the orientations of the input movements 502, 504 and output movements 506, 508 may be quite different, particularly when the output movements are viewed on a display that is offset from the patient. While physicians skilled with catheters and guidewires can readily handle these differences, there can be advantages to increasing the orientational alignment, particularly by rotationally aligning (or allowing the system user to provide a desired rotational alignment) between the X-Y input orientations and the X'-Y' output orientation alignments. Though complex paths are omitted from the illustrated automated articulation modes that follow, the exemplary systems and methods help provide such input-output rotational alignment.

Figure 16B:
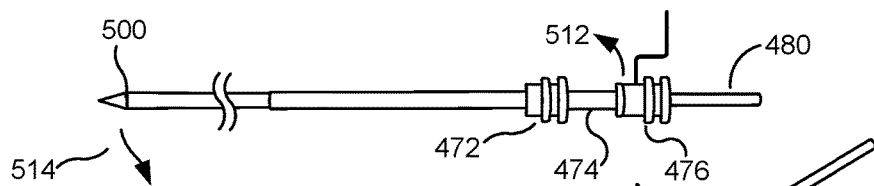
FIGS. 16B-16E schematically illustrate use of the sheath/input assembly of FIG. 14 in a 3-D input mode, in which flexing of the flexible joystick induces X-Y lateral deflection of the distal articulable portion of the catheter, and in which axial sliding of the joystick relative to the introducer sheath induces axial elongation of the articulable portion.

Referring now to FIGS. 15 and 16B, the catheter system may be used in an automated 3-D mode by closing the introducer valve (so that catheter 480 is held in a stationary axial and rotational position by the valve of the introducer). The valve of the input is opened and the interface between the introducer and input is separated so that the input can be moved relative to the introducer within the range of axial motion of the flexible joystick 474 and the lateral flexibility of the joystick and the catheter shaft extending therethrough. Movement command signals are not effective prior to actuation of the clutch, so that the system user can position the input relative to the introducer at a desirable initial relative position and orientation. Input housing 476 may, for example, be rotatable about the axis of the lumen therethrough relative to the introducer sheath housing 472. Where the lateral displacement sensor comprises a flex sensor affixed to the flexible joystick, rotation of the input can be used to orient the X-Y lateral deflections 512 in alignment with the displayed images of output movements, optionally using one or more small test lateral input movement commands. Regardless, while the clutch input is depressed, lateral input 512 causes joystick 474 to flex and transmit associated sensor signals to a processor of the system. The processor determines appropriate drive signals to send to an appropriate balloon inflation valve (or other actuation system components) so that distal end 500 is urged toward a lateral deflection output movement 514, the results of which are illustrated in FIG. 16B. Note that flexing of the shaft in a transverse lateral direction would result in the distal end being urged to similarly move in a transverse lateral direction, thereby providing X-Y deflection input and output. Note also that the output movement may correspond in magnitude to the input command movement, but will often differ in size. For example, output displacement distances may be proportional to but smaller than input displacements; inputs and outputs may have similar orientations but may not have a constant proporationality; output displacement angles may be smaller than, the same as, or larger than input flex angles; and/or the like.

Figure 16C:
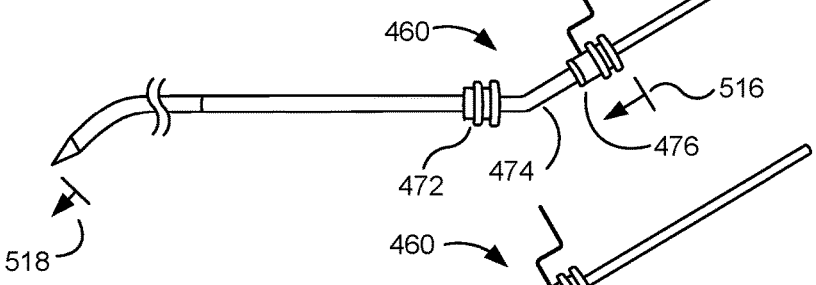
Figure 16D:
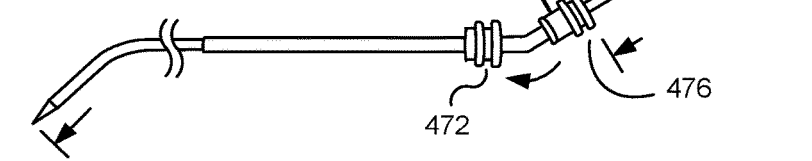

Referring now to FIGS. 16C and 16D, along with (or instead of) X-Y lateral deflection, introducer/input assembly may be used to accept axial (Z) input movement commands, with the assembly accommodating simultaneously in the exemplary 3-D mode. While the clutch input is depressed, input housing 476 may be moved toward introducer housing 472 so as to provide an axial input movement command 516. Flexible joystick 474 slides into introducer housing 472, and the axial sensor sends corresponding axial command signals to the process that result in an axial output movement 518. Note that some systems may help orientationally align these axial inputs and outputs. For example, an orientation of a display image may be rotated using image processing to help align displayed axial movements of distal end 500 with the input; and/or a flexibility of the sheath between the introducer housing and the patient may allow the system user to help align the axial inputs with the associated displayed axial movements. Many other systems may rely on the system user to accommodate axial input/output orientational disparity. In the exemplary embodiment illustrated, axial alignment is not provided (so that Z' may differ from Z), but if an initial test input command indicates the input and outputs lack a desired rotational alignment, the user may simply rotate input housing 476 relative to introducer housing 472. Re-testing and refining of rotational alignment (if desired) should provide the desired lateral (X-Y) alignment quickly, which will help the user to maintain accurate control despite the lack of axial alignment. Other systems may have a rotational input or knob that provides an electronic signal to achieve a similar lateral orientational alignment based on user input.

Figure 16E:
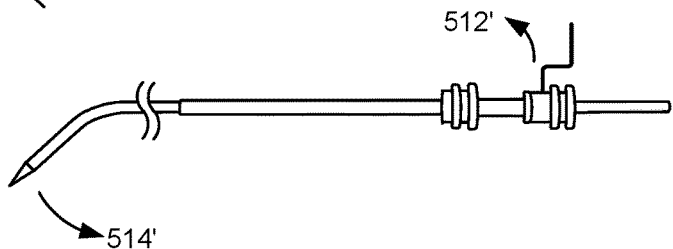

As can be understood with reference to FIGS. 16D and 16E, overall input movement commands may be received (and implemented) by the catheter system as a series of partial movements. To initiate the beginning of a first movement command, the user can actuate the clutch by pressing a clutch button or the like. The processor may store a configuration of the input when the clutch is actuated, and may derive drive signals to seek to perform the commanded movement relative to that initial configuration. When the input approaches an end of its range of motion (which may be imposed by the input device, the anatomy of the patient, the comfort of the physician, or the like) prior to achieving a desired configuration of the catheter, the system user may release the clutch. The system processor may then maintain the articulated portion of the catheter in the configuration or state it was in when the clutch was released, and the system user can return the input (without actuating the clutch button) back toward a middle of a range of motion of the input. The clutch button can then be actuated to again input a portion of the desired overall movement command 512'; the system may in response initiate the remainder of (or another portion of) the desired movement 514'. This can be analogous to lifting up a computer mouse from the edge of the desk prior to getting a cursor to the desired position, moving it back toward the middle of the desk, and putting it back down to allow continued cursor movement.

Referring now to FIGS. 16F and 16G, to initiate a movement of a distal end 500 in an exemplary follow-a-curve mode, catheter 480 can be axially affixed to input housing 476 by closing the input valve, and may allowed to slide relative to introducer housing 472 by opening the introducer valve, with the interface between the valves being detached. A goal of this movement may be (for example) for the catheter tip and body to at least approximately follow a curving 3-D path 520, with the path having a first curved path segment 520a that differs in radius of curvature and/or orientation of curvature from that of a second path segment 520b, both of which may differ from those of another path segment 520c, and so on. To accommodate the desired movement, the articulated portion of the catheter may have a distal-most first articulated segment 522a and a second articulated segment 522b, and may also have a third articulated segment 522c, and optionally one or more additional articulated segments, with these segments typically being axially coupled and independently articulable.

Curve 520 may be defined in a number of different ways. Optionally, curve 520 may be determined prior to initiating a particular axial movement, such as by determining a desired path through a 3-D surface model of the body lumen or volume (such as a blood/tissue boundary along a chamber of the heart). Curve 520 might also be defined by a structure, such as by a guidewire over which catheter 480 is to be advanced. In some embodiments, curve 520 may be generated while the catheter is advancing, such as by using flexible joystick 474 to input a lateral position or curvature of the path associated with the concurrent axial joystick configuration. In many embodiments, segments proximal of the distal most first segment 522a may be driven from their current configuration toward a configuration (actual or commanded or a combination of both) of the distally adjacent segment. Note that in some embodiments, the axial locations of the segments along the elongate body may change or overlap. Regardless, while some embodiments of catheter systems used to implement some or all of the modes described herein may include articulation portions extending proximally from a distal end of the distal-most articulated segment all the way to the access site, many embodiments will rely on passive (un-articulated) proximal portions that extend proximally from the articulated portion and/or segments within the patient body, and that such a passive proximal portion will often be bent laterally along the curving path proximal of the articulated portion. Manual insertion of catheter 480 can be used to provide distal advancement of both the articulated portion and any passive proximal portion along curving path 420 by sensing the manual axial displacement of the catheter via the axial sensor of introducer/input assembly 460, and by driving the articulated segments of the catheter (one or more of 522a, 522b, 522c . . . ), toward a curvature configuration corresponding to that of an adjacent path segment (one or more of 520a, 520b, 520c).

Referring to FIGS. 16F and 16G, the lateral driving of the articulated segments may occur during axial movement, and/or between incremental axial movements. One or more of the articulated segments may be driven so as to assume a curvature associated with an approaching segment before the catheter segment and curve segment are aligned, or once they are aligned. Nonetheless, lateral articulation may be initiated by depressing the clutch of the input and manually moving the input housing 476 relative to the introducer housing 472. Once the input is at or near the end of its range of motion (as seen in FIG. 16G), the clutch can be released. As the valves configurations may be reversed to allow the input to be retracted proximally without moving catheter 480, it may be advantageous to couple clutch release to powered valve actuators for this mode. Regardless, as seen in FIGS. 16G and 16H, input housing 476 can be withdrawn and a new axial displacement increment initiated (with corresponding lateral deflection of articulation segments 522a, 522b, etc.) so that the distal end of the catheter substantially follows along path 520. Note that if any motion in this mode is initiated (by depressing the clutch input, for example) the system processor may determine if any articulation segment of the catheter is in a partially or fully elongated configuration. If one or more of the segments is elongated beyond a desired configuration, and if the catheter is at least initially advanced distally, the processor may transmit axial drive signals so that the elongated segment(s) are retracted axially back to the desired length configuration in correlation with the manual distal movement so as to have the catheter ready for a future driven elongation movement. Once the elongate lengths of the segments are in their desired states, such elongation recovery can be terminated.

Referring now to FIGS. 16I and 16J, yet another mode of movement with the catheter systems described herein may employ partial inflation of articulation balloons so as to locally decrease a lateral stiffness of the catheter so as to tailor a pushability and/or trackability of the catheter for a particular body lumen, and ideally for the axial relationship of the catheter relative to bends of the lumen. Trackability, pushability, torqueability, and crossability of are known characteristics of catheters which may be quantitatively determined subjectively (by asking a number of users to rate the catheters for one or more of these characteristics), empirically (by measuring movement inputs and outputs in a controlled test), and/or analytically (by modelling interaction of the catheter and resulting catheter performance based on characteristics or properties of the catheter structure). Pushability generally reflects the ability of a distal end of the catheter to advance distally within a bending lumen in response to an axial insertion performed from proximally of the lumen, while trackability generally reflects the ability of the distal end of the catheter to follow a path through a bending lumen (optionally as defined by a guidewire or the luminal wall) in response to axial insertion. Both pushability and trackability can vary with a number of different characteristics of the catheter structure (both often improving with increased outer lubricity, for example), but in at least some circumstances they may contradict each other. For example, pushability may be enhanced by increasing an axial stiffness of at least an axial segment of a catheter, while trackability may be enhanced by decreasing that axial stiffness. The fluid articulated catheters described herein may help overcome this challenge for a particular body lumen, because the axial stiffness of the catheter segments can be independently varied by varying balloon pressure, optionally without applying pressure so as to impose lateral bends in any particular direction (absent environmental forces against the catheter).

In FIGS. 16I and 16J, a body lumen has a first bend B1 and a second bend B2 with a straight section between the bends. Good overall pushability and trackability of the catheter in the position of FIG. 16I may benefit from a catheter structure with high lateral flexibility (low stiffness) along catheter segment 520b (proximal of and along bend B1), and a relatively high stiffness (low flexibility) along catheter segments 520a and 520c (extending along straight lumen segments. As the catheter advances distally so that the distal end nears bend B2, trackability may benefit from increasing the flexibility of segment 520a, while pushability and trackability may overall benefit by decreasing the stiffness of segment 520c (as it approaches or reaches bend B1), and increasing the stiffness of segment 520b (as it leaves bend B2 and/or extends along the straight section. By identifying highly curved and straighter segments of the path, by measuring axial insertion of the catheter, and adjusting a pressure of balloons of the segments, for example, so that catheter segments approaching or along greater curvature are less stiff (often by partial balloon inflation), and so that catheter segments approaching or along straighter path portions are more stiff (such as by compete deflation or inflation of the balloons of those segments).

Figure 17:
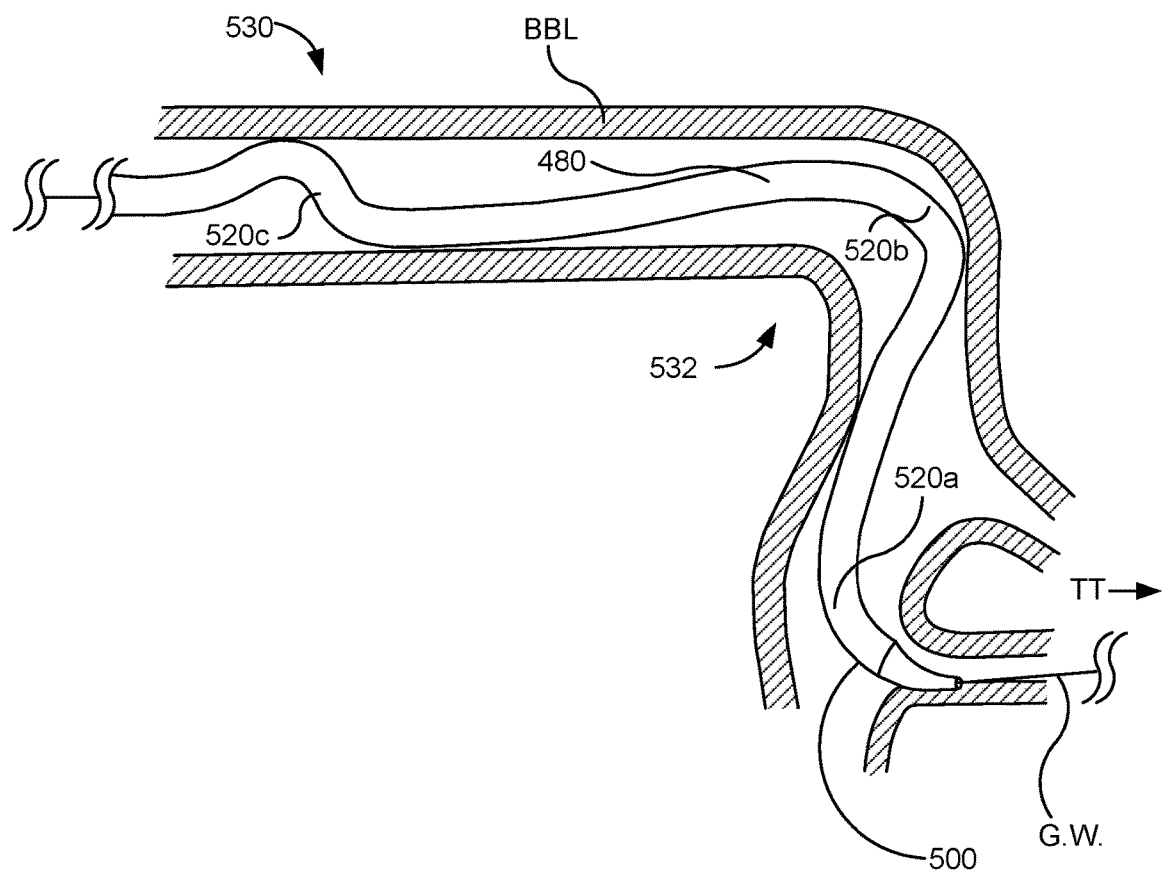
FIG. 17 schematically illustrates lateral deflection of an articulated catheter to provide gentle and releasable anchoring of the catheter within the body lumen, use of an anchored catheter as a base for 3-D steering of a catheter, and sensing of a curved path distal of and end of a catheter body by detecting deflection of soft distal guide tip against a lumen wall and/or guidewire.

Referring now to FIG. 17, two different anchor modes of catheter 480 can be understood. In this embodiment, it is desired to align distal end 500 of catheter 480 with a target tissue TT that is accessed via a branching body lumen BBL. To access the target tissue and/or to produce the desired alignment, catheter 480 may advance over a guidewire GW, or may be self-guiding, and will use lateral deflection and axial elongation of a distal articulable catheter segment 520a as generally described above. The system user has here determined it would be desirable to anchor the catheter 480 proximally of segment 520a, for example, so that the distal segment of the catheter will move with physiological movement near the target tissue TT, so that the distal segment of the catheter is isolated from movement proximal of the anchor location, to stabilize segment 520a during articulation, or the like. To provide a desired anchoring engagement between an outer surface of catheter 480 and the luminal wall at a first anchoring location 530 extending along a relatively straight section of the branching body lumen BBL, catheter articulation segment 520c may be driven so as to impose at least one bend and preferably so as to impose opposed bends, sinusoidal bends, a helical bend, or the like. Anchoring engagement at a bent location 532 of the body lumen can be provided by driving articulation segment 520b toward a catheter bend configuration having a bend angle which is greater than that of the body lumen bend. Note that FIG. 17 also illustrates lateral deflection of a flexible tip 534 of catheter 480 as imposed by guidewire GW, the lumen wall, or both. Such a flexible tip having a flex sensor (optionally an optical fiber or flex circuit) can measure such deflection and generate signals that may be used as a distal path curve sensor, as can be understood above.

Figure 18:
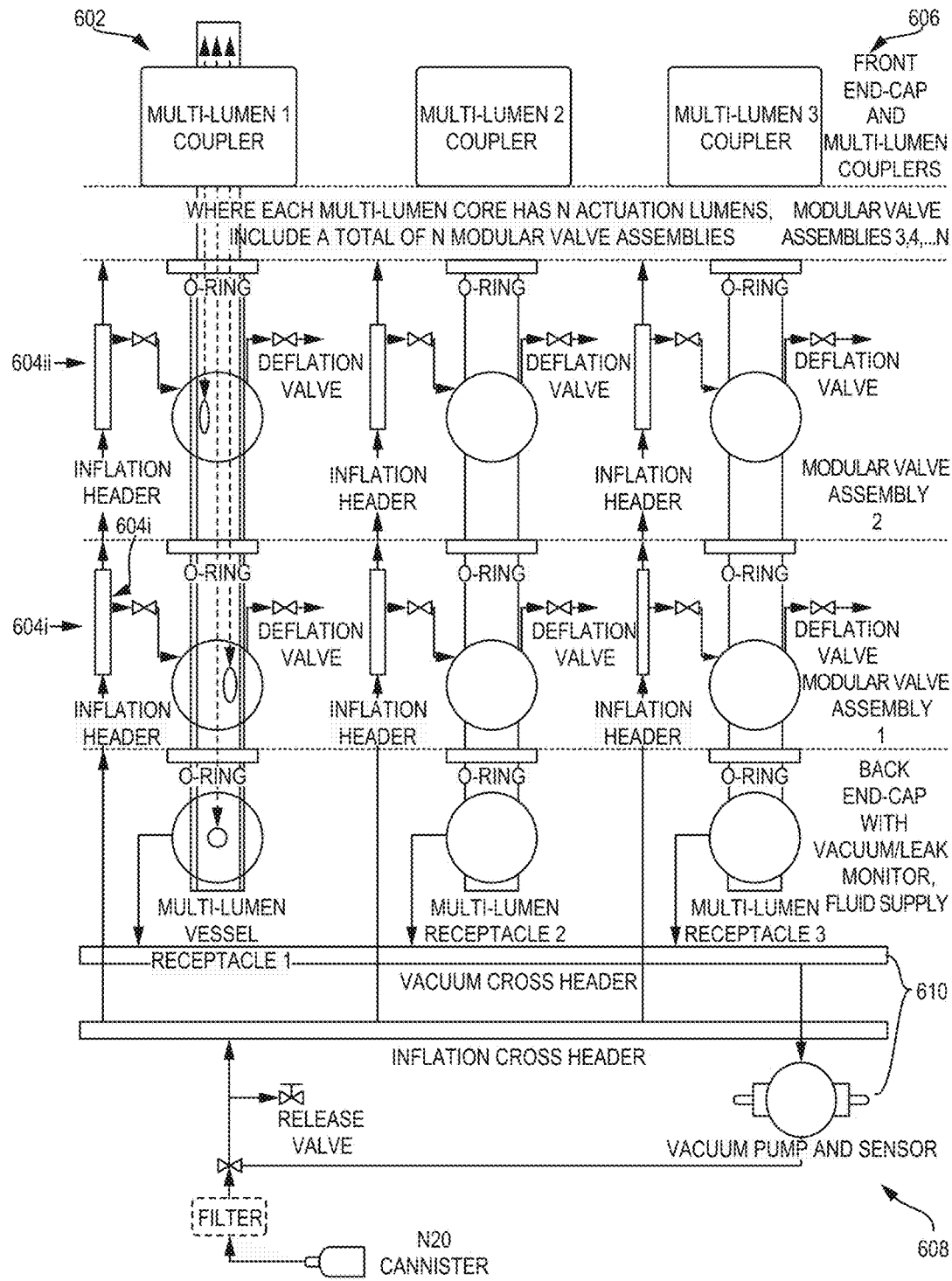
FIG. 18 is a simplified schematic of a modular manifold having a stack of valve plate assemblies through which a multi-lumen connector extends so as to provide controlled fluid flow to and from balloons of an array.

Referring now to FIG. 18, a simplified manifold schematic shows fluid supply and control components of an alternative manifold 602. As generally described above, manifold 602 has a plurality of modular manifold units or valve assembly plates 604*i*, 604*ii*, . . . stacked in an array. The stack of valve plates are sandwiched between a front end cap 606 and a back end-cap 608, and during use the proximal portion of the multi-lumen conduit core(s) extend through apertures in the front cap and valve plates so that the proximal end of the core is adjacent to or in the back cap, with the apertures defining a multi-lumen core receptacle. The number of manifold units or modules in the stack is sufficient to include a plate module for each lumen of each of the multi-lumen core(s). For example, where an articulatable structure has 3 multi-lumen core shafts and each shaft has 6 lumens, the manifold assembly may include a stack of 6 plates. Each plate optionally includes an inflation valve and a deflation valve to control pressure in one of the lumens (and the balloons that are in communication with that lumen) for each multi-lumen shaft. In our 3-multi-lumen shaft/6 lumen each example, each plate may include 3 inflation valves (one for a particular lumen of each shaft) and 3 deflation valves (one for that same lumen of each shaft). As can be understood with reference to the multi-lumen shaft shown in receptacle 1 of FIG. 18, the spacing between the ports along the shaft corresponds to the spacing between the fluid channels along the receptacle. By inserting the core shaft fully into the multi-lumen shaft receptacle, the plate channel locations can be registered axially with the core, and with the ports that were drilled radially from the outer surface of the multi-lumen core. The processor can map the axial locations of the valves along the receptacle with the axial locations of the ports along the core shafts, so that a port into a particular lumen of the core can be registered and associated with a fluid channel of specific inflation and deflation valves. One or more inflation headers can be defined by passages axially through the valve-unit plates; a similar deflation header (not shown) can also be provided to monitor pressure and quantity of fluid released from the lumen system of the articulated device. O-rings can be provided adjacent the interface between the plates surrounding the headers and receptacles. Pressure sensors (not shown) can monitor pressure at the interface between each plate and the multi-lumen receptacle. It should be noted that a wide variety of alternative manifold and catheter coupler structures might also be used, including manifold systems in which a stacked plate connector system is used for interfacing with the catheter, and in which an array of ports extend laterally from the connector to provide a quick-disconnect interface with a reusable valve assembly (as shown in FIGS. 29-30C and described below).

Along with monitoring and controlling inflation and deflation of all the balloons, manifold 602 can also include a vacuum monitor system 610 to verify that no inflation fluid is leaking from the articulated system within the patient body. A simple vacuum pump (such as a syringe pump with a latch or the like) can apply a vacuum to an internal volume or chamber of the articulated body surrounding the balloon array. Alternative vacuum sources might include a standard operating room vacuum supply or more sophisticated powered vacuum pumps. Regardless, if the seal of the vacuum chamber degrades the pressure in the chamber of the articulated structure will increase. In response to a signal from a pressure sensor coupled to the chamber, a shut-off valve can automatically halt the flow of gas from the canister, close all balloon inflation valves, and/or open all balloon deflation valves. Such a vacuum system may provide worthwhile safety advantages when the articulated structure is to be used within a patient body and the balloons are to be inflated with a fluid that may initially take the form of a liquid but may vaporize to a gas. A lumen of a multi-lumen core shaft may be used to couple a pressure sensor of the manifold to a vacuum chamber of the articulated structure via a port of the proximal interface and an associated channel of the manifold assembly, with the vacuum lumen optionally comprising a central lumen of the multi-lumen shaft and the vacuum port being on or near the proximal end of the multi-lumen shaft.

Many of the flexible articulated devices described above rely on inflation of one or more balloons to articulate a structure from a first resting state to a second state in which a skeleton of the flexible structure is resiliently stressed. By deflating the balloons, the skeleton can urge the flexible structure back toward the original resting state. This simple system may have advantages for many applications. Nonetheless, there may be advantages to alternative systems in which a first actuator or set of actuators urges a flexible structure from a first state (for example, a straight configuration) to a second state (for example, a bent or elongate configuration), and in which a second actuator or set of actuators are mounted in opposition to the first set such that the second can actively and controllably urge the flexible structure from the second state back to the first state. Toward that end, exemplary systems described below often use a first set of balloons to locally axially elongate a structural skeleton, and a second set of balloons mounted to the skeleton to locally axially contract the structural skeleton. Note that the skeletons of such opposed balloon systems may have very little lateral or axial stiffness (within their range of motion) when no balloons are inflated.

Figure 19:
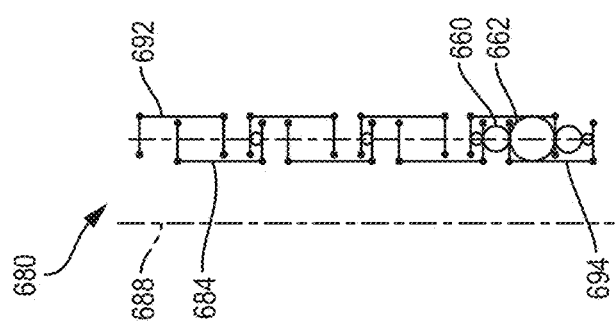

Referring now to FIG. 19, a simplified exemplary C-channel structural skeleton 680 includes an axial series of C-channel members or frames 682, 684 extending between a proximal end (toward the bottom of the page) and a distal end (toward the top of the page) of the skeleton, with each rigid C-channel including an axial wall, a proximal flange, and a distal flange 642. The opposed major surfaces of the walls are oriented laterally, and the opposed major surfaces of the flanges are oriented axially (and more specifically distally and proximally, respectively. The C-channels alternate in orientation so that the frames are interlocked by the flanges. Hence, axially adjacent frames overlap, with the proximal and distal surfaces of two adjacent frames defining an overlap offset. The flanges also define additional offsets, with these offsets being measured between flanges of adjacent similarly oriented frames.

Balloons are disposed in the channels of each C-frame 682, 684 (only some of which are shown). Although the balloons themselves may (or may not) be structurally similar, the balloons are of two different functional types: extension balloons 660 and contraction balloons 662. Both types of balloons are disposed axially between a proximally oriented surface of a flange that is just distal of the balloon, and a distally oriented surface of a flange that is just proximal of the balloon. However, contraction balloons 662 are also sandwiched laterally between a first wall of a first adjacent C-channel 682 and a second wall of a second adjacent channel 684. In contrast, extension balloons 660 have only a single wall on one lateral side; the opposite sides of extension balloons 660 are not covered by the frame (though they will typically be disposed within a flexible sheath or other components of the overall catheter system). When extension balloons 660 are fully inflated, they push the adjacent flange surfaces apart so as to increase the axial separation between the associated frames. Contraction balloons 662 are disposed in a C-channel with an extension balloon, and as the size of the channel will not significantly increase, the contraction balloons will often be allowed to deflate at least somewhat with expansion of the extension balloons. Hence, offsets between adjacent similar frames (682, 682) will be urged to expand, and contraction offsets between differently oriented frames (682, 684) will be allowed to decrease. In contrast, when skeleton 680 is to be driven toward an axially contracted configuration, the contraction balloons 662 are inflated, thereby pushing the flanges of the overlapping frames axially apart to force the contraction overlap to increase and axially pull the local skeleton structure into a shorter configuration. To allow the contraction balloons 662 to expand within a particular C-channel, the expansion balloons 660 can be allowed to deflate. A number of alternative frame arrangements having opposed extension/contraction balloons can also be provided, as can be understood with reference to Provisional U.S. Application No. 62/296,409 filed Feb. 17, 2016, entitled "Local Contraction of Flexible Bodies using Balloon Expansion for Extension-Contraction Catheter Articulation and Other Uses".

Note that whichever extension/contraction skeleton configuration is selected, the axial change in length of the skeleton that is induced when a particular subset of balloons are inflated and deflated will often be local, optionally both axially local (for example, so as to change a length along a desired articulated segment without changing lengths of other axial segments) and—where the frames extend laterally and/or circumferentially—laterally local (for example, so as to impose a lateral bend by extending one lateral side of the skeleton without changing an axial length of the other lateral side of the skeleton). Note also that use of the balloons in opposition will often involve coordinated inflating and deflating of opposed balloons to provide a maximum change in length of the skeleton. There are significant advantages to this arrangement, however, in that the ability to independently control the pressure on the balloons positioned on either side of a flange (so as to constrain an axial position of that flange) allows the shape and the position or pose of the skeleton to be modulated. If both balloons are inflated evenly at with relatively low pressures (for example, at less than 10% of full inflation pressures), the flange may be urged to a middle position between the balloons, but can move resiliently with light environmental forces by compressing the gas in the balloons, mimicking a low-spring force system. If both balloons are evenly inflated but with higher pressures, the skeleton may have the same nominal or resting pose, but may then resist deformation from that nominal pose with a greater stiffness.

Referring again to FIG. 19, a C-frame skeleton 680 has two different generally C-frames or members: a C-frame 682, and a bumper C-frame 684. C-frame 682 and bumper frame 684 both have channels defined by walls 644 and flanges 648 with an axial width to accommodate two balloon assemblies. Bumper frame 684 also has a protrusion or nub that extends from one flange axially into the channel. The adjacent axial surfaces of these different frame shapes engage each other at the nub, allowing the frames to pivot relative to each other and facilitating axial bending of the overall skeleton, particularly when using helical frame members.

Figure 20:
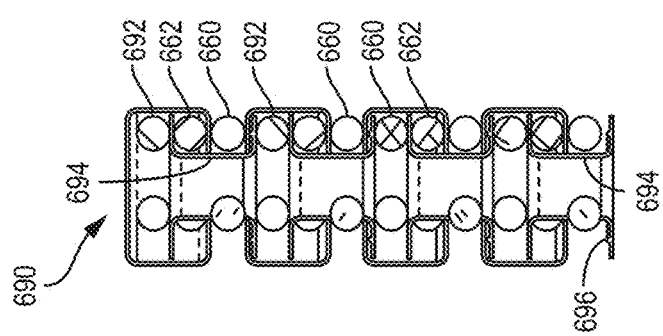
FIGS. 19 and 20 are a schematic illustration of an exemplary axial expansion/contraction skeleton with axial expansion and axial contraction balloons; and a corresponding cross-section of a skeleton having an axial series of annular members or rings articulated by the axial expansion and axial contraction balloons, respectively.

Referring now to FIGS. 19 and 20, a relationship between the schematic extension/retraction frame illustration of FIG. 19 and a first exemplary three dimensional skeleton geometry can be understood. To form an axisymmetric ring-frame skeleton structure 690 from the schematic modified C-frame skeleton 680 of FIG. 19, the geometry of frame members 682, 684 can be rotated about an axis 688, resulting in annular or ring frames 692, 694. These ring frames retain the wall and flange geometry described above, but now with annular wall and flanges being interlocked. The annular C-frames 682, 684 were facing different directions in schematic skeleton 680, so that outer C-frame ring 692 has an outer wall (sometimes being referred to as outer ring frame 692) and a channel that opens radially inwardly, while bumper C-frame ring 694 has a channel that is open radially outwardly and an inner wall (so that this frame is sometimes referred to as the inner ring frame 694). Ring nub 696 remains on inner ring frame 694, but could alternatively be formed on the adjacent surface of the outer ring frame (or using corresponding features on both). Note that nub 696 may add more value where the frame deforms with bending (for example, the frame deformation with articulation of the helical frame structures described below) as the deformation may involve twisting that causes differential angels of the adjacent flange faces. Hence, a non-deforming ring frame structure might optionally omit the nub in some implementations.

Figure 23:
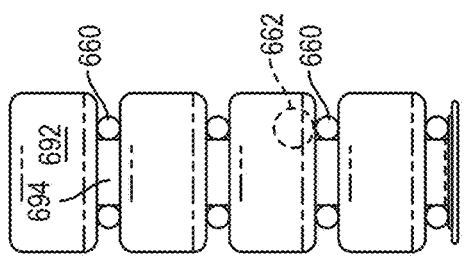
FIGS. 21-23 are illustrations of elongate flexible articulated structures having annular skeletons with three opposed sets of balloons, and show how varying inflation of the balloons can be used to axially contract some portions of the frame and axially extend other portions to bend or elongate the frame and to control a pose or shape of the frame in three dimensions.
Figure 22:
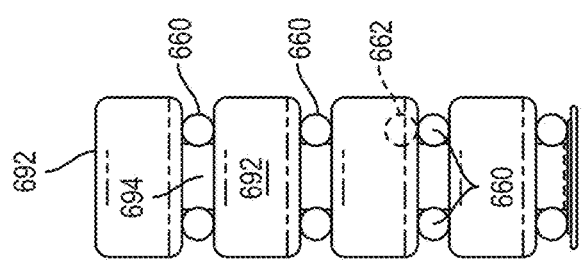
Figure 21:
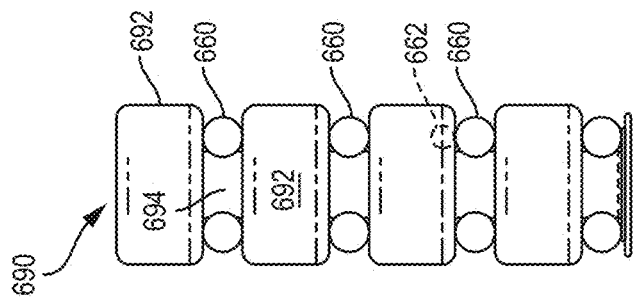

Referring now to FIGS. 21-23, uniform axial extension and contraction of a segment of ring-frame skeleton 690 is performed largely as described above. To push uniformly about the axis of the ring frames, three balloons are distributed evenly about the axis between the flanges (with centers separated by 120 degrees). The balloons are shown here as spheres for simplicity, and are again separated into extension balloons 660 and contraction balloons 662. In the straight extended configuration of FIG. 21, the extension balloons 660 of the segment are all fully inflated, while the contraction balloons 662 are all fully deflated. In an intermediate length configuration shown in FIG. 22, both sets of balloons 660, 662 are in an intermediate inflation configuration. In the short configuration of FIG. 23, contraction balloons 662 are all fully inflated, while extension balloons 660 are deflated. Note that the state of the balloons remains asymmetrical, so that the lengths on all lateral sides of the ring frame skeleton 690 remain consistent and the axis of the skeleton remains straight. Lateral bending or deflection of the axis of ring-frame skeleton 690 can be accomplished by differential lateral inflation of subsets of the extension and contraction balloons. More specifically, there are three balloons distributed about the axis between each pair of articulated flanges, so that the extension balloons 660 are divided into three sets. Similarly, there are three sets of contraction balloons. The balloons of each set are aligned along the same lateral orientation from the axis. Each axially aligned set of extension balloons along a particular segment can be coupled to an associated inflation fluid channel, and each axially aligned set of contraction balloons can be coupled to an associated inflation channel so that there are a total of 6 lumens or channels per segment (providing three degrees of freedom and three orientation-related stiffnesses). Other segments may have separate fluid channels to provide separate degrees of freedom, and alternative segments may have fewer than 6 fluid channels. Regardless, by selectively deflating the extension balloons of a first lateral orientation and inflating the opposed contraction balloons, a first side of ring frame skeleton 690 can be shortened. By selectively inflating the extension balloons of the other orientations and by selectively deflating the contraction balloons of those other orientations, the laterally opposed portion of ring frame skeleton 690 can be locally extended, causing the axis of the skeleton to bend. By modulating the amount of elongation and contraction distributed about the three opposed extension/contraction balloon orientations, the skeleton pose can be smoothly and continuously moved and controlled in three degrees of freedom.

While it is possible to include balloons between all the separated flanges so as to maximize available extension forces and the like, there may be advantages to foregoing kinematically redundant balloons in the system for compactness, simplicity, and cost. Toward that end, ring frame skeletons having 1-for-1 opposed extension and contraction balloons can provide the same degrees of freedom and range of motion as provided by the segments of FIGS. 19-23 (including two transverse X-Y lateral bending degrees of freedom and an axial Z degree of freedom), and can also control stiffness, optionally differentially modulating stiffness of the skeleton in different orientations in 3D space. The total degrees of freedom of such a segment may appropriately be referenced as being 4-D (X, Y, Z, &S for Stiffness), with the stiffness degree of freedom optionally having 3 orientational components (so as to provide as many as 5-D or 6-D. Regardless, the 6 fluid channels may be used to control 4 degrees of freedom of the segment.

As can be understood with reference to FIGS. 23A-23H, elongate flexible bodies having ring-frame skeletons 690' with larger numbers of inner and outer ring frames 692, 694 (along with associated larger numbers of extension and retraction balloons) will often provide a greater range of motion than those having fewer ring frames. The elongation or Z axis range of motion that can be provided by balloon articulation array may be expressed as a percentage of the overall length of the structure, with larger percentage elongations providing greater ranges of motion. The local changes in axial length that a balloon array may be able to produce along a segment having ring frames 690, 690' (or more generally having the extension contraction skeleton systems described herein) may be in a range of from about 1 percent to about 45 percent, typically being from about 2½ percent to about 25 percent, more typically being from about 5 percent to about 20 percent, and in many cases being from about 7½ percent to about 17½ percent of the overall length of the skeleton. Hence, the longer axial segment length of ring frame skeleton 690' will provide a greater axial range of motion between a contracted configuration (as shown in FIG. 23C) and an extended configuration (as shown in FIG. 23A), while still allowing control throughout a range of intermediate axial length states (as shown in FIG. 23B).

Figure 23G:
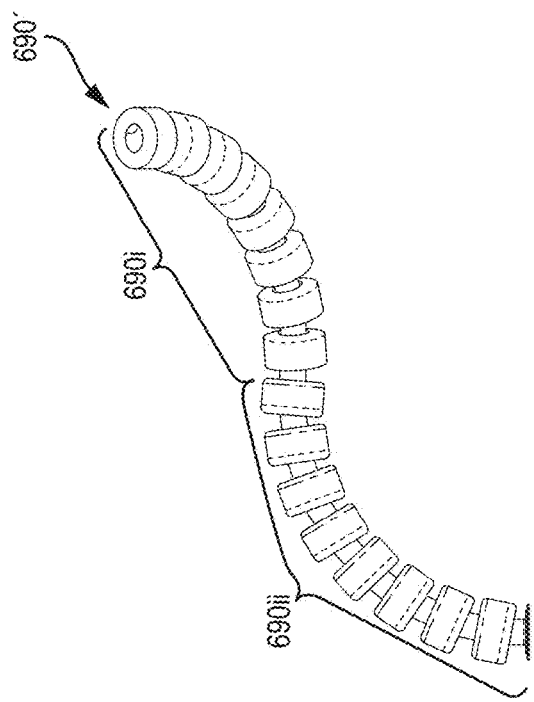
Figure 23H:
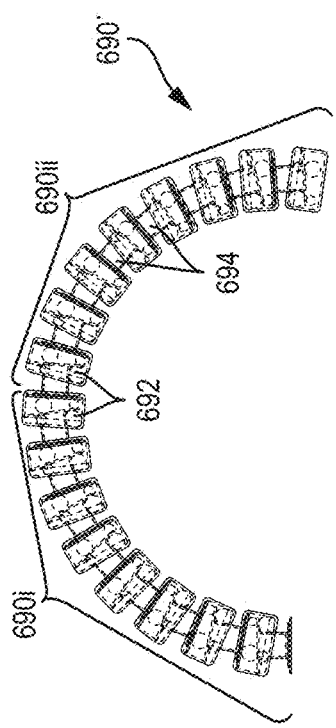
Figure 23F:
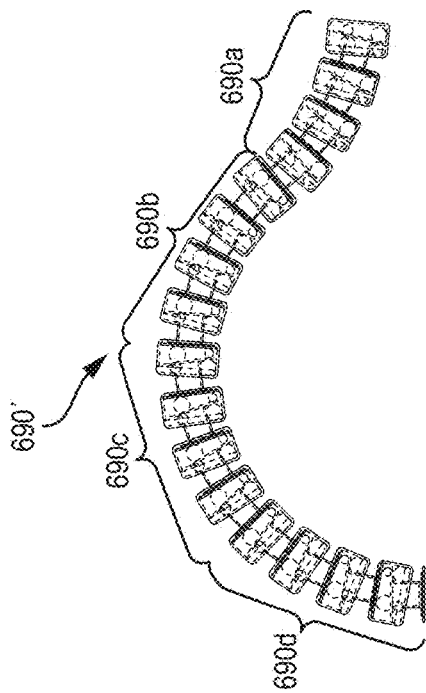

As can be understood with reference to FIG. 23F, setting the balloon pressures so as to axially contract one side of a ring frame skeleton 690' (having a relatively larger number of ring frames) and axially extend the other side laterally bends or deflects the axis of the skeleton through a considerable angle (as compared to a ring frame skeleton having fewer ring frames), with each frame/frame interface typically between 1 and 15 degrees of axial bend angle, more typically being from about 2 to about 12 degrees, and often being from about 3 to about 8 degrees. A catheter or other articulated elongate flexible body having a ring frame skeleton may be bent with a radius of curvature (as measured at the axis of the body) of between 2 and 20 times an outer diameter of the skeleton, more typically being from about 2.25 to about 15 times, and most often being from about 2.4 to about 8 times. While more extension and contraction balloons 660, 662 are used to provide this range of motion, the extension and contraction balloon subsets may still each be supplied by a single common fluid supply lumen. For example, 6 fluid supply channels may each be used to inflate and deflate 16 balloons in the embodiment shown, with the balloons on a single lumen being extension balloons aligned along one lateral orientation.

As can be understood with reference to ring frame skeleton 690' in the straight configuration of FIG. 23A, in the continuously bent configuration of FIG. 23F, and in the combined straight and bent configuration of FIGS. 23D & 23E, exemplary embodiments of the elongate skeleton 690' and actuation array balloon structures described herein may be functionally separated into a plurality of axial segments 690*i*, 690*ii*. Note that many or most of the skeleton components (including frame members or axial series of frame members, and the like) and actuation array components (including the substrate and/or core, some or all of the fluid channels, the balloon outer tube or sheath material, and the like), along with many of the other structures of the elongate flexible body (such as the inner and outer sheaths, electrical conductors and/or optical conduits for diagnostic, therapeutic, sensing, navigation, valve control, and other functions) may extend continuously along two or more axial segments with few or no differences between adjacent segments, and optionally without any separation in the functional capabilities between adjacent segments. For example, an articulated body having a two-segment ring frame skeleton 690' system as shown in FIG. 23F may have a continuous axial series of inner and outer ring frames 692, 694 that extends across the interface between the joints such that the two segments can be bent in coordination with a constant bend radius by directing similar inflation fluid quantities and pressures along the fluid supply channels associated with the two separate segments. As can be understood with reference to FIG. 23E, other than differing articulation states of the segments, there may optionally be few or no visible indications of where one segment ends and another begins.

Despite having many shared components (and a very simple and relatively continuous overall structure), functionally separating an elongate skeleton into segments provides tremendous flexibility and adaptability to the overall articulation system. Similar bend radii may optionally be provided with differing stiffnesses by applying appropriately differing pressures to the opposed balloons 660, 662 of two (or more) segments 690*i*, 690*ii*. Moreover, as can be understood with reference to FIG. 23D, two (or more) different desired bend radii, and/or two different lateral bend orientations and/or two different axial segments lengths can be provided by applying differing inflation fluid supply pressures to the opposed contraction/extension balloon sets of the segments. Note that the work spaces of single-segment and two-segment systems may overlap so that both types of systems may be able to place an end effector or tool at a desired position in 3D space (or even throughout a desired range of locations), but multiple-segment systems will often be able to achieve additional degrees of freedom, such as allowing the end effector or tool to be oriented in one or more rotational degrees of freedom in 6D space. As shown in FIG. 23H, articulated systems having more than two segments offer still more flexibility, with this embodiment of ring frame skeleton 690' having 4 functional segments 690*a*, 690*b*, 690*c*, and 690*d*. Note that still further design alternatives may be used to increase functionality and cost/complexity of the system for a desired workspace, such as having segments of differing length (such as providing a relatively short distal segment 690*a* supported by a longer segment having the combined lengths of 690*b*, 690*c*, and

690*d*. While many of the multi-segment embodiments have been shown and described with reference to to planar configurations of the segments where all the segments lie in a single plane and are either straight or in a fully bent configuration, it should also be fully understood that the plurality of segments 690*i*, 690*ii*, etc., may bend along differing planes and with differing bend radii, differing axial elongation states, and/or differing stiffness states, as can be understood with reference to FIG. 23G.

Catheters and other elongate flexible articulated structures having ring frame skeletons as described above with reference to FIGS. 20-23H provide tremendous advantages in flexibility and simplicity over known articulation systems, particularly for providing large numbers of degrees of freedom and when coupled with any of the fluid supply systems described herein. Suitable ring frames may be formed of polymers (such as nylons, urethanes, PEBAX, PEEK, HDPE, UHDPE, or the like) or metals (such as aluminum, stainless steel, brass, silver, alloys, or the like), optionally using 3D printing, injection molding, laser welding, adhesive bonding, or the like. Articulation balloon substrate structures may initially be fabricated and the balloon arrays assembled with the substrates in a planar configuration as described above, with the arrays then being assembled with and/or mounted on the skeletons, optionally with the substrates being adhesively bonded to the radially inner surfaces of the inner rings and/or to the radially outer surfaces of the outer rings, and with helical or serpentine axial sections of the substrate bridging between ring frames. While extension and retraction balloons 660, 662 associated with the ring frame embodiments are shown as spherical herein, using circumferentially elongate (and optionally bent) balloons may increase an area of the balloon/skeleton interface, and thereby enhance axial contraction and extension forces. A huge variety of modifications might also be made to the general ring-frame skeletal arrangement and the associated balloon arrays. For example, rather than circumferentially separating the balloons into three lateral orientations, alternative embodiments may have four lateral orientations (+X, −X, +Y, and −Y) so that four sets of contraction balloons are mounted to the frame in opposition to four sets of extension balloons. Regardless, while ring-frame skeletons have lots of capability and flexibility and are relatively geometrically simple so that their functionality is relatively easy to understand, alternative extension/contraction articulation systems having helical skeleton members (as described below) may be more easily fabricated and/or more easily assembled with articulation balloon array components, particularly when using the advantageous helical multi-lumen core substrates and continuous balloon tube structures described above.

First reviewing components of an exemplary helical frame contraction/expansion articulation system, FIGS. 24A-24E illustrate actuation balloon array components and their use in a helical balloon assembly. FIGS. 24F and 24G illustrate exemplary outer and inner helical frame members. After reviewing these components, the structure and use of exemplary helical contraction/expansion articulation systems (sometimes referred to herein as helical push/pull systems) can be understood with reference to FIGS. 25 and 26.

Figure 24A:
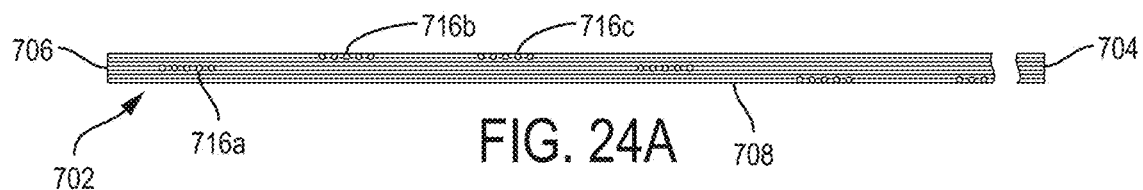
FIGS. 24A-24G illustrate components of another alternative elongate articulated flexible structure having axial expansion balloons and opposed axial contraction balloons, the structures here having helical skeleton members and helical balloon assemblies.
Figure 24B:
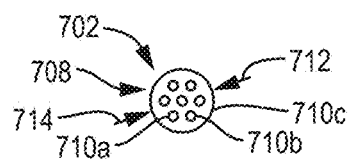

Referring now to FIGS. 24A and 24B, an exemplary multi-lumen conduit or balloon assembly core shaft has a structure similar to that of the core described above with reference to FIGS. 14 and 15. Core 702 has a proximal end 704 and a distal end 706 with a multi-lumen body 708 extending therebetween. A plurality of lumens 710*a*, 710*b*, 710*c*, . . . extend between the proximal and distal ends. The number of lumens included in a single core 702 may vary between 3 and 30, with exemplary embodiments have 3, 7 (of which one is a central lumen), 10 (including 1 central), 13 (including 1 central), 17 (one being central), or the like. The multi-lumen core will often be round but may alternatively have an elliptical or other elongate cross-section as described above. When round, core 702 may have a diameter 712 in a range from about 0.010" to about 1", more typically being in a range from about 0.020" to about 0.250", and ideally being in a range from about 0.025" to about 0.100" for use in catheters. Each lumen will typically have a diameter 714 in a range from about 0.0005" to about 0.05", more preferably having a diameter in a range from about 0.001" to about 0.020", and ideally having a diameter in a range from about 0.0015" to about 0.010". The core shafts will typically comprise extruded polymer such as a nylon, urethane, PEBAX, PEEK, PET, other polymers identified above, or the like, and the extrusion will often provide a wall thickness surrounding each lumen of more than about 0.0015", often being about 0.003" or more. The exemplary extruded core shown has an OD of about 0.0276"", and 7 lumens of about 0.004" each, with each lumen surrounded by at least 0.004" of the extruded nylon core material.

Referring still to FIGS. 24A and 24B, the lumens of core 702 may have radial balloon/lumen ports 716*a*, 716*b*, 716*c*, . . . , with each port comprising one or more holes formed through the wall of core 702 and into an associated lumen 710*a*, 710*b*, 710*c*, . . . respectively. The ports are here shown as a group of 5 holes, but may be formed using 1 or more holes, with the holes typically being round but optionally being axially elongate and/or shaped so as to reduce pressure drop of fluid flow therethrough. In other embodiments (and particularly those having a plurality of balloons supplied with inflation fluid by a single lumen), having a significant pressure drop between the lumen and the balloon may help even the inflation state of balloons, so that a total cross section of each port may optionally be smaller than a cross-section of the lumen (and/or by limiting the ports to one or two round lumens). Typical ports may be formed using 1 to 10 holes having diameters that are between 10% of a diameter of the associated lumen and 150% of the diameter of the lumen, often being from 25% to 100%, and in many cases having diameters of between 0.001" and 0.050". Where more than one hole is included in a port they will generally be grouped together within a span that is shorter than a length of the balloons, as each port will be contained within an associated balloon. Spacing between the ports will correspond to a spacing between balloons to facilitate sealing of each balloon from the axially adjacent balloons.

Regarding which lumens open to which ports, the ports along a distal portion of the core shaft will often be formed in sets, with each set being configured to provide fluid flow to and from an associated set of balloons that will be distributed along the loops of the core (once the core is bent to a helical configuration) for a particular articulated segment of the articulated flexible body. When the number of lumens in the core is sufficient, there will often be separate sets of ports for different segments of the articulated device. The ports of each set will often form a periodic pattern along the axis of the multi-lumen core 702, so that the ports provide fluid communication into M different lumens (M being the number of different balloon orientations that are to be distributed about the articulated device axis, often being 3 or 4, i.e., lumen 710*a*, lumen 710*b*, and lumen 710*c*) and the pattern repeating N times (N often being the number of contraction balloons along each orientation of a segment).

Hence, the multi-lumen core conduit can function as a substrate that supports the balloons, and that defines the balloon array locations and associated fluid supply networks described above. Separate multi-lumen cores 702 and associated balloon arrays may be provided for contraction and expansion balloons.

As one example, a port pattern might be desired that includes a 3×5 contraction balloon array for a particular segment of a catheter. This set of ports might be suitable when the segment is to have three lateral balloon orientations (M=3) and 5 contraction balloons aligned along each lateral orientation (N=5). In this example, the distal-most port 716*a* of the set may be formed through the outer surface of the core into a first lumen 710*a*, the next proximal port 716*b* to lumen 710*b*, the next port 716*c* to lumen 710*c*, so that the first 3 (M) balloons define an "a, b, c" pattern that will open into the three balloons that will eventually be on the distal-most helical loop of the set. The same pattern may be repeated 5 times (for example: a, b, c, a, b, c, a, b, c, a, b, c, a, b, c) for the 5 loops of the helical coil that will support all 15 contraction balloons of a segment to the fluid supply system such that the 5 contraction balloons along each orientation of the segment are in fluid communication with a common supply lumen. Where the segment will include expansion balloons mounted 1-to-1 in opposition to the contraction balloons, a separate multi-lumen core and associated balloon may have a similar port set; where the segment will include 2 expansion balloons mounted in opposition for each contraction balloon, two separate multi-lumen cores and may be provided, each having a similar port set.

If the same multi-lumen core supplies fluid to (and supports balloons of) another independent segment, another set of ports may be provided axially adjacent to the first pattern, with the ports of the second set being formed into an M'×N' pattern that open into different lumens of the helical coil (for example, where M'=3 and N'=5: d, e, f, d, e, f, d, e, f, d, e, f, d, e, f), and so on for any additional segments. Note that the number of circumferential balloon orientations (M) will often be the same for different segments using a single core, but may be different in some cases. When M differs between different segments of the same core, the spacing between ports (and associated balloons mounted to the core) may also change. The number of axially aligned contraction balloons may also be different for different segments of the same helical core, but will often be the same. Note also that all the balloons (and associated fluid lumens) for a particular segment that are on a particular multi-lumen core will typically be either only extension or only contraction balloons (as the extension and contraction balloon arrays are disposed in helical spaces that may be at least partially separated by the preferred helical frame structures described below). A single, simple pattern of ports may be disposed near the proximal end of core shaft 702 to interface each lumen with an associated valve plate of the manifold, the ports here being sized to minimized pressure drop and the port-port spacing corresponding to the valve plate thickness. Regardless, the exemplary core shown has distal ports formed using groups of 5 holes (each having a diameter of 0.006", centerline spacing within the group being 0.012"), with the groups being separated axially by about 0.103".

Figure 24C:
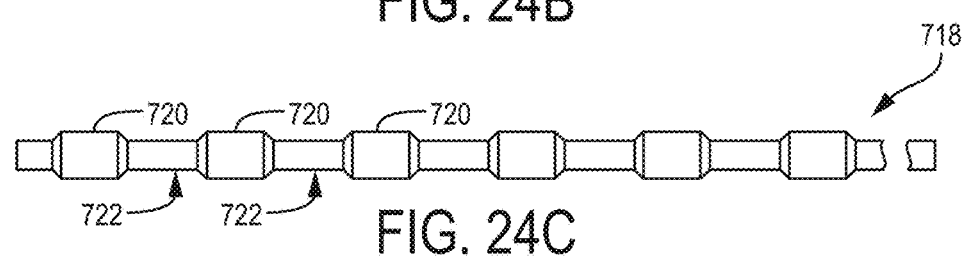
Figure 24D:
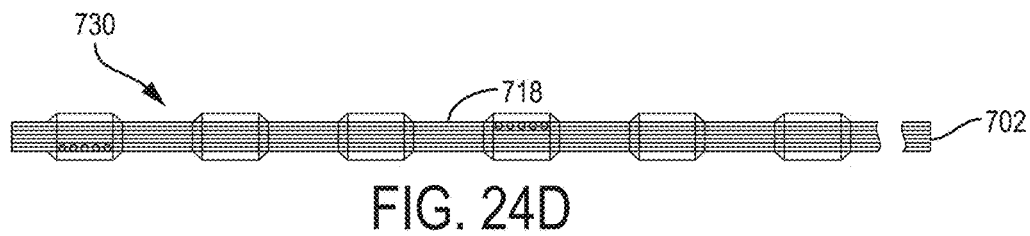
Figures 1, 24E:
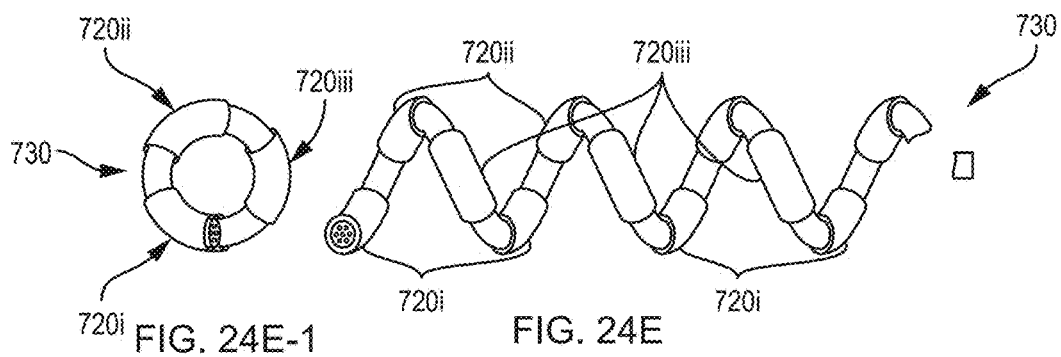
Figure 24F:
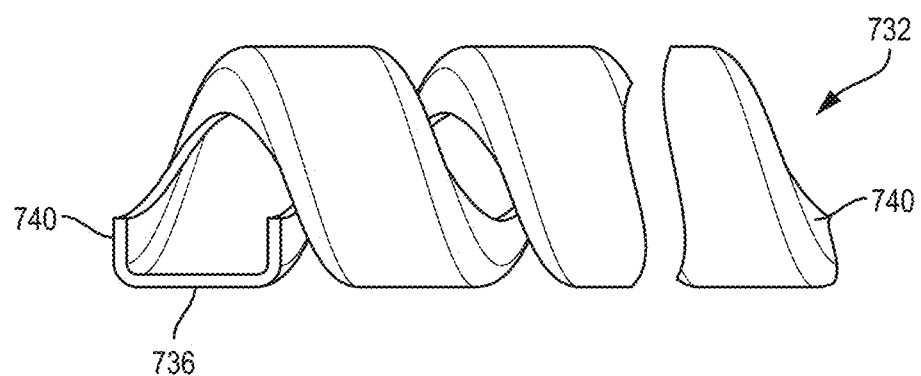
Figure 24G:
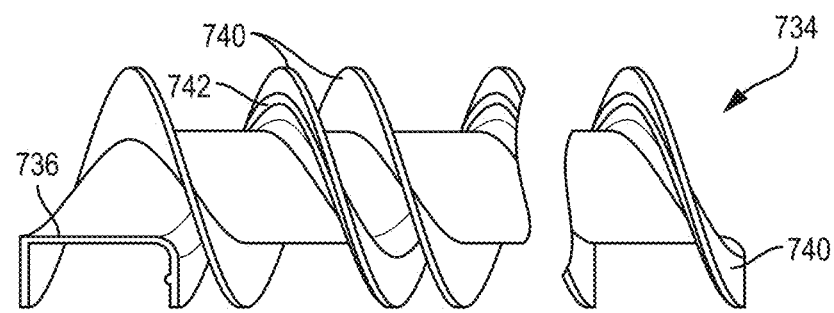

Referring now to FIGS. 24C and 24D, a continuous tube of flexible balloon wall material 718 may be formed by periodically varying a diameter of tube wall material to form a series of balloon shapes 720 separated by smaller profile sealing zones 722. Balloon tube 718 may include between about 9 and about 290 regularly spaced balloon shapes 720, with the sealing zones typically having an inner diameter that is about equal to the outer diameters of the multi-lumen helical core shafts 702 described above. In some embodiments, the inner diameters of the sealing zones may be significantly larger than the outer diameters of the associated cores when the balloon tube is formed, and the diameters of the sealing zones may be decreased (such as by heat shrinking or axially pull-forming) before or during assembly of the balloon tube and core shaft. The sealing zone may have a length of between about 0.025" and about 0.500", often being between about 0.050" and about 0.250". Decreasing the length of the sealing zone allows the length of the balloon to be increased for a given catheter size so as to provide larger balloon/frame engagement interfaces (and thus greater articulation forces), while longer sealing zones may facilitate assembly and sealing between balloons so as to avoid cross-talk between articulation channels.

Referring still to FIGS. 24C and 24D, the balloon shapes 720 of the balloon tube 718 may have diameters that are larger than the diameters of the sealing zones by between about 10% and about 200%, more typically being larger by an amount in a range from about 20% to about 120%, and often being from about 40% to about 75%. The thickness of balloon tube 718 will often vary axially with the varying local diameter of the tube, the locally large diameter portions forming the balloon shapes optionally being in a range from about 0.00008' (or about 2 microns) to about 0.005", typically being from about 0.001" and about 0.003". Balloon tube 718 may initially be formed with a constant diameter and thickness, and the diameter may be locally expanded (by blow forming, by vacuum forming, by a combination of both blow forming and vacuum forming, or by otherwise processing the tube material along the balloon shapes 720), and/or the diameter of the balloon tube may be locally decreased (by heat shrinking, by axial pull-forming, by a combination of both heat shrinking and pull forming, or by otherwise processing the tube material along the sealing zones), with the tube material often being processed so as to both locally expand the diameter along the desired balloon shapes and to locally contract the diameter along the sealing zones. Particularly advantageous techniques for forming balloon tubes may include the use of extruded polymer tubing corrugators, including the vertical small bore corrugators commercially available from Unicore, Corma, Fraenkische, and others. Suitable custom molds for such pipe corrugators may be commercially available from GlobalMed, Custom Pipe, Fraenkische, and others. Still more advanced fabrication techniques may allow blow or vacuum corrugation using a robotic shuttle corrugator and custom molds, particularly when it is desirable to change a size or spacing of balloons along a continuous tube. It should be noted that while a single continuous balloon tube is shown, a plurality of balloon tubes (each having a plurality (or in some cases, at least one) balloon shape) can be sealingly mounted onto a single core. Regardless, the sealing zones will often have a material thickness that is greater than that of the balloon shapes.

The balloon shapes 720 of the balloon tube 718 may each have a relatively simple cylindrical center section prior to assembly as shown. The tapers between the balloon center sections and the sealing zones can take any of a variety of shapes. The tapers may, for example, be roughly conical, rounded, or squared, and will preferably be relatively short so as to allow greater balloon/frame engagement for a given landing zone length. More complex embodiments may also be provided, including forming the balloon shapes with curved cylindrical center sections, optionally while corrugating or undulating the surfaces of the tapers so that the balloon tube overall remains relatively straight. The lengths of each center section is typically sufficient to define an arc-angle of from 5 to 180 degrees about the axis of the desired balloon assembly helix, more typically being from about 10 to about 50 degrees, the lengths of the center sections often being in a range from about 0.010" to about 0.400" for medical applications, more typically being from about 0.020" to about 0.150", and many times being in a range from about 0.025" to about 0.100". The exemplary balloon shapes may have an outer diameter of about 0.051" over a total balloon length (including the tapers) of about 0.059"

As can be understood with reference to FIGS. 24C, 24D, 24E, and 24E-1, balloon tube 718 may be sealingly affixed to core 702, and the core/balloon tube assembly may then be formed into a desired helical shape. The balloon tube may be sealed over the helical core using adhesive (such as any of those described above, often including UV-cured adhesives) thermal bonding, laser bonding, die bonding, and/or the like. Sealing of the balloons may also benefit from a compression structure disposed over the balloon material to help maintain tube/core engagement when the balloons are inflated. Suitable compression structures or techniques may include short sections of heat-shrink materials (such as PET) shrunk onto the sealing zones, high-strength filament windings wrapped circumferentially around the sealing zones and adhesively bonded, swaging of metallic ring structures similar to marker bands over the sealing zones, small bore crimp clamps over the sealing zones, heat-shrinking and/or pull forming the balloon tube onto the core, or the like. Any two or more of these may also be combined, for example, with the balloon tube being adhesively bonded to the core tube by injecting adhesive into the balloon tube around the sealing zone, heat shrinking the balloon tube and a surrounding PET sleeve over the sealing zone, and then swaging a metallic marker band over the sealing PET sleeve (so that the sleeve provides strain relief). Regardless, ports 716 will preferably be disposed within corresponding balloon shapes 720 and will remain open after the balloon/core assembly 730 is sealed together in the straight configuration shown in FIG. 24D. Shape setting of the balloon/core assembly from the straight configuration to the helically curved configuration of FIG. 24E can be performed by wrapping the assembly around and/or within a mandrel and heating the wrapped assembly. Helical channels may be included in the mandrel, which may also have discrete balloon receptacles or features to help ensure alignment of sets of balloons along the desired lateral balloon axes. Regardless, shape setting of the core/balloon assembly can help set the M different lateral orientations of the balloons, so that the balloons of each set 720$i$, 720$ii$, 720$iii$ are aligned (as can be understood with reference to FIGS. 24E and 24E-1).

Referring now to FIGS. 24F and 24G, exemplary inner and outer helical C-channel frames, 732 and 734 respectively, can be seen. Inner helical frame 732 and outer helical frame 734 incorporate the modified C-channel frame 680 of FIG. 22a, but with the C-channels defined by axially continuous helical walls 736 with flanges 740 along their proximal and distal helical edges. The helical flanges are axially engaged by opposed balloons and allow inflation of the balloons to locally axially contract and/or extend the skeleton and catheter (or other articulatable body) in a manner that is analogous to the annular flanges of the ring frames described above. An optional helical nub 742 protrudes axially into the channel of inner ring frame 734 to allow the frames to pivot against each other along a flange/flange engagement, so that the nub could instead be included on the flange of the outer frame or on both (or may comprise a separate structure that is axially sandwiched between the flanges of the two frames). Alternative embodiments may forego such a pivotal structure altogether.

Referring now to FIGS. 25A-25D, a segment of an exemplary flexible extension/contraction helical frame articulation structure 750 (sometimes referred to herein as a push/pull helical structure) incorporates the components of FIGS. 24A-24G, and provides the functionality of the annular extension/contraction frame embodiments of FIGS. 22B-22I. Push/pull structure includes a skeleton defined by inner and outer helical frames 732, 734, and also includes three balloon/core assemblies 730$a$, 730$b$, and 730$c$, respectively. Each balloon/core assembly includes a set of balloons at three lateral orientations, 720$i$, 720$ii$, and 720$iii$. Balloon/core assembly 730$b$ extends along a helical space that is axially between a flange of the inner frame and a flange of the outer frame, and that is radially between a wall of the inner frame and a wall of the outer frame, so that the frames overlap along this balloon/core assembly. Hence, when balloons 720 of balloon/core assembly 730 inflate, they push the adjacent flanges apart and increase the overlap of the frames, inducing axial contraction of the skeleton, such that the balloons of this assembly function as contraction balloons. In contrast, balloon/core assemblies 730$a$ and 730$c$ are radially adjacent to only inner frame 732 (in the case of assembly 730$a$) or outer frame 734 (in the case of assembly 730$b$). Expansion of the balloons 720 of assemblies 730$a$, 730$c$ pushes axially against frames so as to decrease the overlap of the frames, and acts in opposition to the inflation of balloons 720 of assembly 730$b$. Hence, balloons 720 of assemblies 730$a$, 730$c$ function as extension balloons.

Referring now to FIGS. 25A-25C, when all the contraction balloons 720 of assembly 730$b$ are inflated and all the extension balloons of assemblies 730$a$, 730$c$ are deflated, the push/pull structure 750 is in a straight short configuration as shown in FIG. 25A. Even partial inflation of the extension balloons and even partial deflation of the contraction balloons articulates push/pull structure 750 to a straight intermediate length configuration, and full inflation of all extension balloons of assemblies 730$a$, 730$c$ (along with deflation of the contraction balloons) fully axially elongates the structure. As with the ring push/pull frames, inflating contraction balloons 720$ii$ along one lateral orientation of assembly 730$b$ (with corresponding deflation of the extension balloons 720$ii$ of assemblies 730$a$, 730$b$) locally decreases the axial length of the skeleton along that side, while selective deflation of contraction balloons 720$i$ of assembly 730$b$ (with corresponding inflation of extension balloons 720$i$ of assemblies 730$a$ and 730$c$) locally increases the length of the skeleton, resulting in the fully laterally bent configuration of FIG. 25E. Note that extension and contraction balloons along the 720$iii$ orientation may be inflated and deflated with the extension and contraction orientation balloons of orientation 720$ii$ so as to keep the curvature in the plane of the drawing as shown. Stiffness of the structure may be modulated uniformly or locally (with axial and/or orientation variations) as described above regarding the ring frame embodiments. Similarly, the number of extension and contraction balloons along each orientation (which will often be associated with the number of loops of assemblies 730$a$, 730$b$, etc) may be determined to provide the desired range of motion, resolution, and response. As described with reference to the push/pull ring frame embodiments, the overall articulated portion of the structure will often be separated into a plurality of independently controllable segments.

Figure 25F:
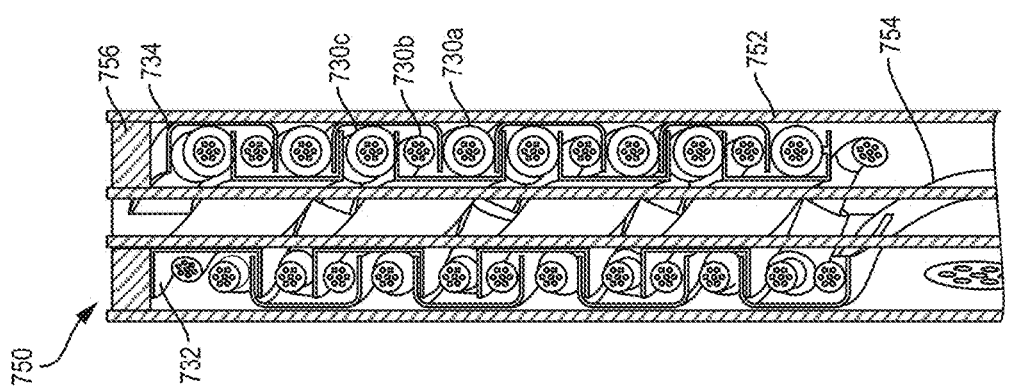

Referring now to FIG. 25F, push/pull structure 750 will often include an outer flexible sheath 752 and an inner flexible sheath 754. Sheaths 752, 754 may be sealed together at a distal seal 756 distal of the inflation lumens and balloons of assemblies 730, and one or more proximal seal (not shown) may be provided proximal of the balloons and/or near a proximal end of the catheter structure, so as to provide a sealed volume surrounding the articulation balloons. A vacuum can be applied to this sealed volume, and can be monitored to verify that no leaks are present in the balloons or inflation lumen system within a patient body.

Figure 26B:
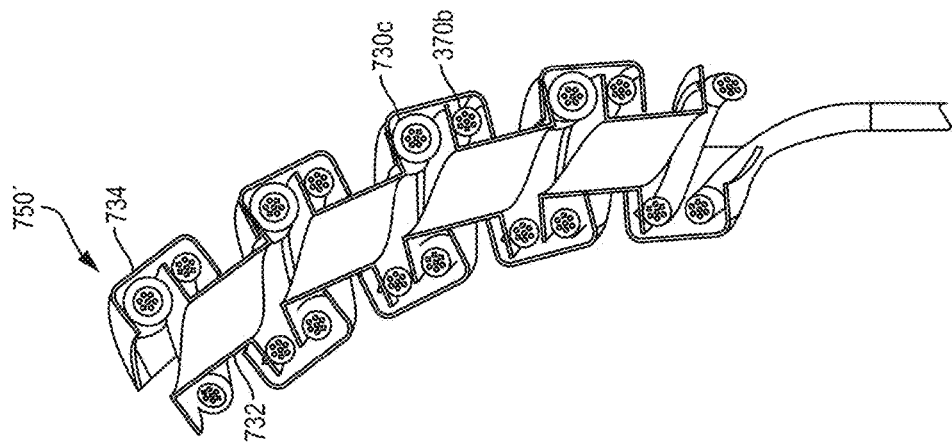
FIGS. 26A and 26B illustrate alternative articulated structures similar to those of FIG. 25, here with two balloon assemblies supported in opposition along the frames.
Figure 26A:
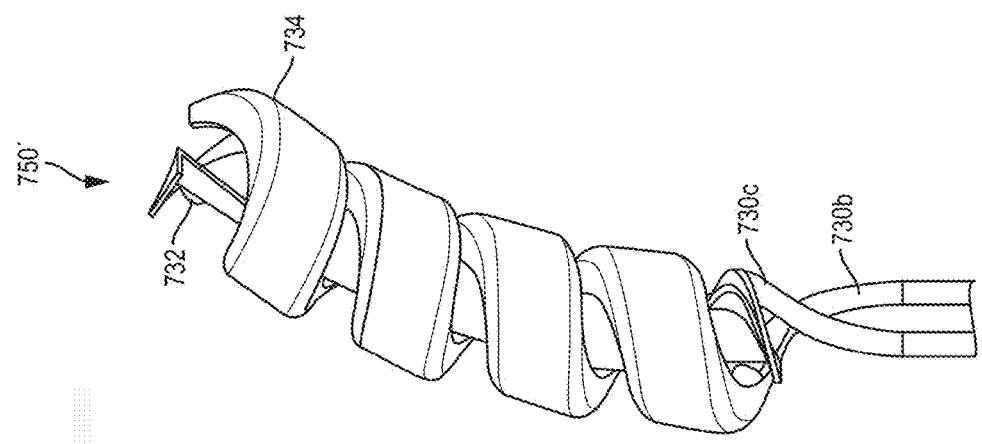

Referring now to FIGS. 26A and 26B, an alternative push/pull structure omits one of the two extension balloon assemblies 730a, 730c, and uses a 1-to-1 extension/contraction balloon opposition arrangement as described above with reference to FIGS. 23A and 23B. Note that this embodiment retains balloon assembly 730c that is radially adjacent to outer frame 734 (so that no balloons are visible even with the sheath removed). Alternative embodiments may retain assembly 730a and forego assembly 730c (so that balloons could be seen through a clear sheath, for example).

A variety of catheter sizes and capabilities may be provided, with the number of segments often being related to the size and lumens of the cores shaft. Core shaft 702 has an outer diameter of about 0.028" and 7 lumens, with 6 peripheral lumens having an inner diameter of about 0.004" readily available for formation of associated ports and use in transmitting inflation fluid to and from balloons. A central lumen might be used, for example, in monitoring of the vacuum system to verify integrity of the system. Core shaft 702 can be used, for example, in a 14-15 Fr catheter system having two segments that are each capable of providing up to 120 degrees of bending (or alternatively more or less depending on the number of balloons ganged together on each channel), with such a system optionally capable of providing a bend radius sufficient to fit a 180 degree bend of the catheter within a space of 3 inches or less, ideally within 2½ inches or less, and in some cases within 2 inches or less. Such a system may be beneficial for structural heart therapies, for example, and particularly for mitral valve delivery, positioning, and/or implantation. Other therapies may benefit from smaller catheter profiles, and do not need the bending forces available from a 15 Fr catheter. Electrophysiology therapies such as AFib ablation from within an atrium of the heart may be good examples of therapies which would benefit from the degrees of freedom that can be provided in small structures using the systems described herein. Scaling the 15 Fr system down for a 7-8 Fr ablation catheter might make use of a directly scaled core having half the overall outer diameter and half the lumen inner diameter of core 702, as the pressure-containing stresses in the material would scale with the lumen diameters. However, there may be cost benefits to maintaining minimum lumen wall thicknesses that are above 0.002", preferably at or above 0.0025", and ideally at or above about 0.003". Toward that end, and to provide 6 contraction or extension lumens for two 3D push/pull segments along a common helical core along with a desirably small bend radius, it may be beneficial to use radially elongate core 764 having a 6 lumens that are all surrounded by at least 0.003" of material. Still further advantages may be provided by applying the smaller lumen and wall thickness dimensions of 7 Fr core to a 15 Fr catheter core size, as it results in a 12 inflation lumen core 766. A large 13$^{th}$ lumen of this embodiment may help enhance flexibility of the segments, and can again be used to monitor system integrity using a vacuum system. The 12 lumens may allow, for example, a continuous push/pull structure to have 4 independently controllable 3D shape (4D shape+stiffness) segments. A 16 inflation lumen core may be provided by combining the smaller lumen and wall thickness with a radially elongate cross-section, allowing 5 independently controllable 3D segments. It should be understood that still further numbers of lumens at smaller profiles are possible using known and relatively low cost multilumen extrusion techniques.

It should be understood that still further alternative embodiments may take advantage of the beneficial components and assemblies described herein. For example, as can be understood from the disclosure above regarding many of the flexible structures of FIGS. 3-12, inflation of a balloon may be resiliently opposed by a helical spring or other biasing structure so that the spring deflates the balloon and urges a flexible body back toward a pre-balloon-inflation state when the inflation fluid is released from the balloon. Rather than relying on 6 dedicated opposed expansion and contraction balloon channels for each segment (providing independent contraction and expansion along each lateral orientation) in the push/pull ring frame and push/pull helical frame embodiments described above, two or more of the channels (from the same segments or from different segments) may be grouped together to act as a common bailing structure or fluid spring. As an example, all the contraction balloons along two adjacent segments might open to a single lumen that is inflated to less than full pressure. Modulating pressure to the different sets of extension balloons may still allow the extension balloons to articulate each segment with three independent degrees of freedom, as the grouped contraction balloons could selectively be overpowered by the extension balloons (like the coil springs) or may be allowed to deflate the extension balloons. In some embodiments, rather than relying on partial pressure of extension or contraction balloons, an elastomeric material may be mounted over the core of some or all of the extension or contraction balloons of a segment so as to passively oppose a set of the balloons.

Figure 27:
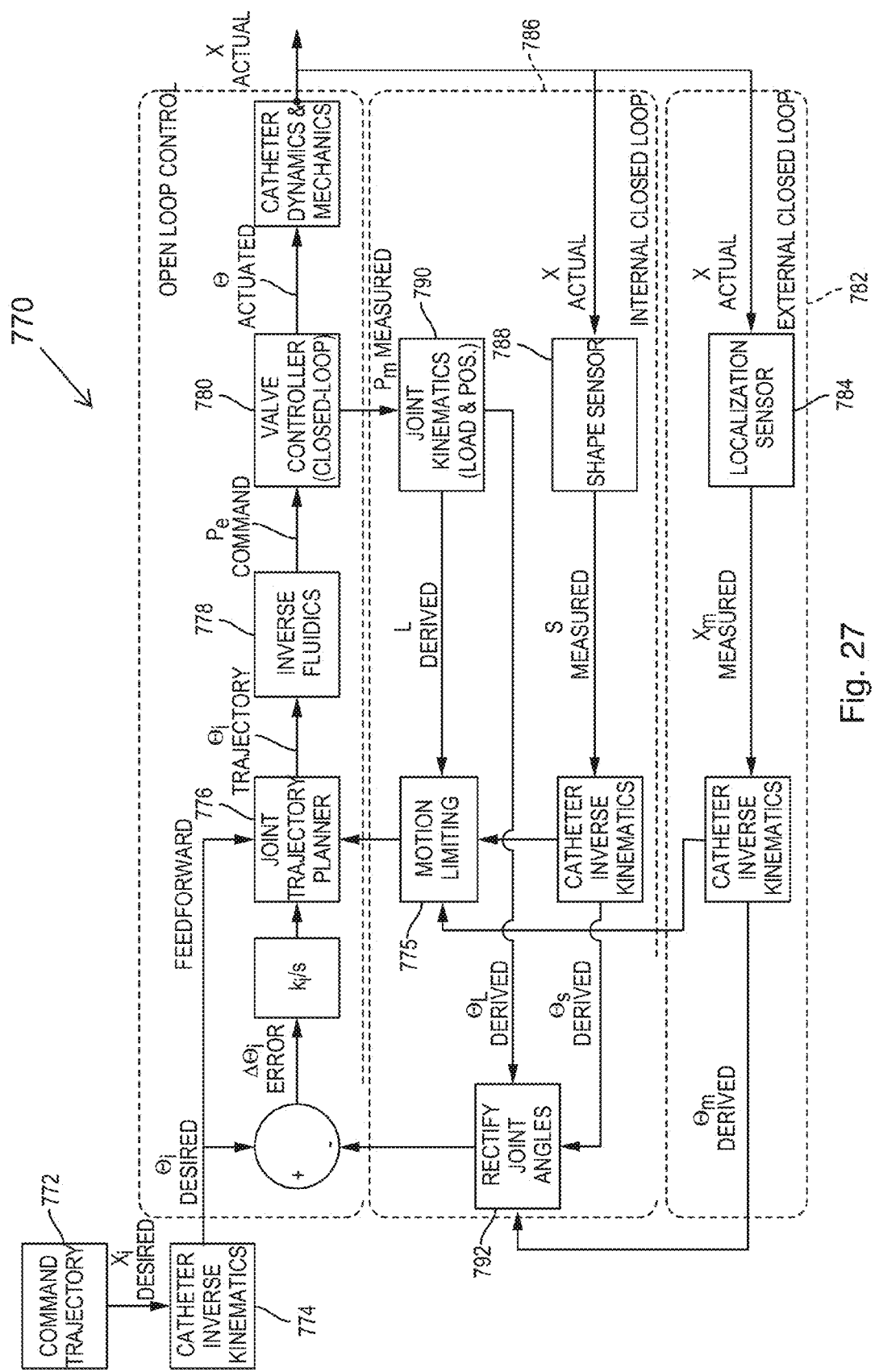
FIG. 27 schematically illustrates control system logic for using the fluid drive systems described herein to articulate catheters and other elongate flexible structures per input provided by a system user.

Referring now to FIG. 27, an articulation controller 770 for directing inflation fluid to and from the actuation balloons of the systems will typically have hardware and/or software configured and programmed to generally seek to cause the articulable structure to assume a new actual position or state $X_{actual}$ in response to a commanded trajectory 772 input by a system user. Many of the articulated flexible structures described herein may be included in robotic systems that can be analyzed and controlled using techniques associated with continuum robots, and the articulated structures will often be under-constrained with more joints then can be directly controlled by the system using standard controller. These excess or redundant degrees of freedom are often managed and made to cooperate using an internal compliance that directs the joints to be at a similar angle relative to the next joint within the segment. These equal joint angles may help lead the system toward a lowest potential energy state for the system. Other alternative goals for the excess joints of the system are described herein. The processor of the system will typically have software modules to determine the next desired position or state of the articulatable structure $X_{iDesired}$, and will apply inverse catheter kinematics 774 to determine the next desired joint state $\Theta_{iDesired}$. A difference between an actual joint state and the next desired joint state is determined to define a joint error, and the desired joint state can be fedforward to a joint trajectory planner 776 along with the joint error to define a joint error trajectory. This joint trajectory can be used in an inverse fluidic calculation 778 to determine command signals that can be fed into a closed-loop valve controller 780 so as to provide an actuated joint state. In some embodiments, closed loop control of the valves may depend on pressure sensing, and may be used to control to specific pressures as determined by valve inverse kinematics. The catheter dynamics and mechanics reaction to the actuated joint state (with the associated environment interactions with the catheter such as tissue forces and the like) result in a new actual position or state $X_{actual}$ of the articulated catheter system.

Feedback on the actual position or state of the articulated system to the controller may be omitted in some embodiments, but other embodiments may benefit from such feedback to provide more precise movements and better correlation (from the system user's perspective) between the command inputs and the actual changes in state. Toward that end, the controller may optionally use one or more closed loop feedback pathways. In some embodiments, a feedback system that is partially or fully external to the articulated structure 782 may sense the actual position or state of the catheter or other articulated structure using a localization sensor 784, such as an electromagnetic navigation system, an ultrasound navigation system, image processing coupled to 3D imaging (such as biplanor fluoroscopy, magnetic resonance imaging, computed tomography, ultrasonography, stereoscopic cameras, or the like; where the imaging modality may optionally also be used to produce images presented to the system user for image guided articulation). In many embodiments, the feedback will be provided using signals obtained from the articulated system itself under an internal closed loop feedback system 786. To obtain a measured shape or state of the articulated structure, a variety of known sensor technologies may be employed as an articulated structure shape sensor 788, including optical fiber shape sensors (such as those using fiber Bragg gratings), electrical shape sensors (such as those which use elastically deformable circuit components), or the like. The measured and/or sensed signals may be processed using inverse kinematics to derive associated measure and/or sensed joint states. Furthermore, balloon array pressure signals will often be available from the pressure sensors of the system, along with information correlating the pressures with the joint or shape state of the articulated system. The history of inflation fluid directed to and exhausted from the articulation balloons may also be used to help determine an estimated inflation fluid quantity present in each balloon (or set of balloons on a common inflation lumen). Where balloons are mounted in opposition or in parallel, the pressure and inflation fluid quantity of these related balloons on separate channels may also be available. Some or all of this pressure information may be processed using a joint kinematics processor 790 to determine a pressure-derived joint position or state (including a derived position of the pressure-articulated joints making up the flexible structure kinematic chain $\Theta_{LDevived}$). The pressure information, preferably along with internal localization information and/or external localization information, may also be used by the joint kinematic processor 790 to derive the loads on the joints, for determining of motion limits 775 as used by the joint trajectory planner 776, and the like. Where more than one is available, the external localization-based feedback joint state, the internal shape-sensor based joint state, and the pressure-derived joint state may be rectified 792 and the rectified (or otherwise any available) joint state compared to the desired joint state to determine the joint error signal.

Figure 28:
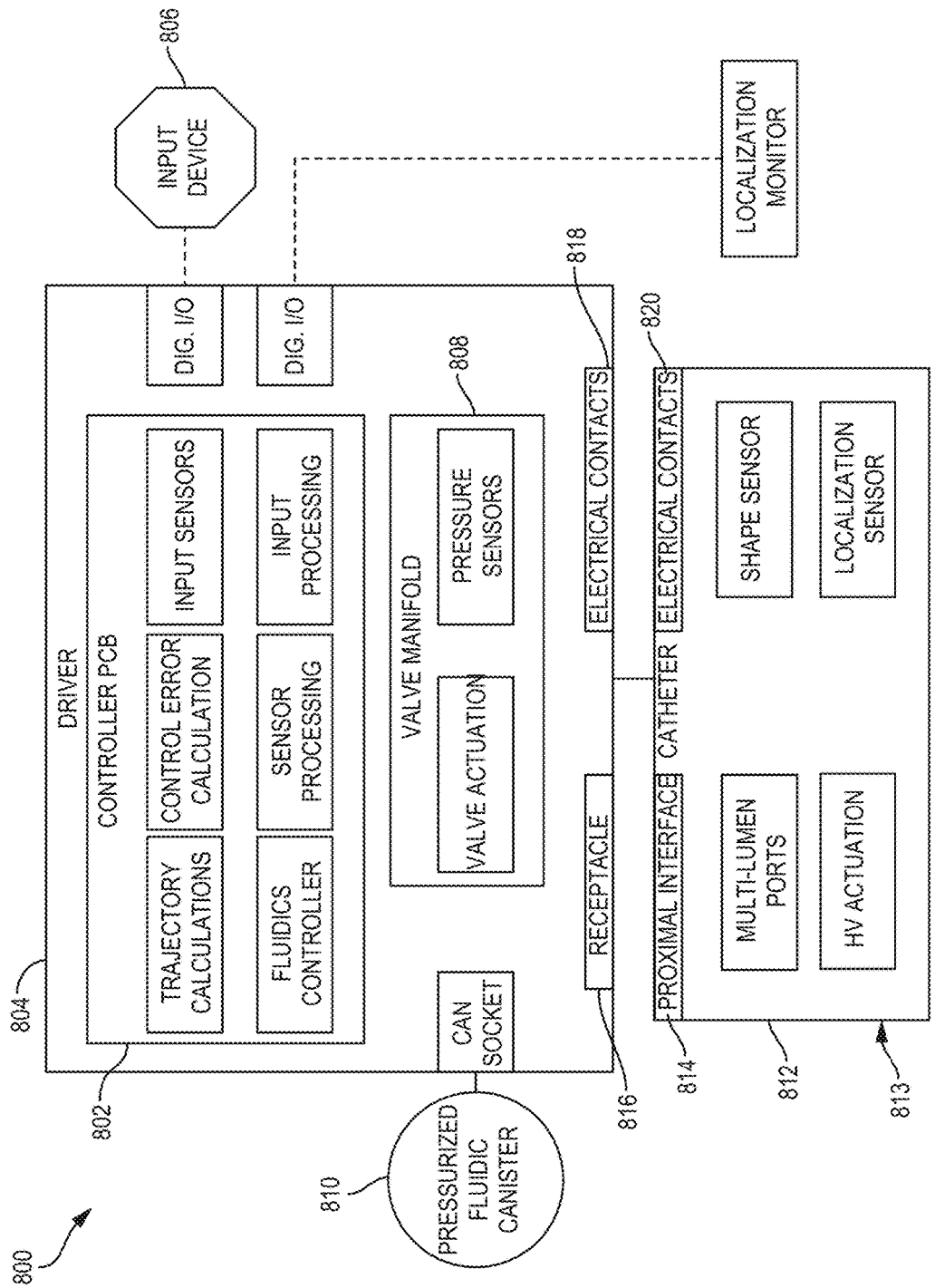
FIG. 28 schematically illustrates a data acquisition and processing system for use within the systems and methods described herein.

Referring now to FIG. 28, an exemplary data processing structure 800 for controlling the shape of a catheter or other articulated elongate flexible bodies described herein can be understood. Much of the data processing occurs on a controller board 802 of reusable driver 804, with the driver optionally comprising a hand-held capital equipment unit. The input device 806 may optionally include a separate workstation with wired or wireless data telemetry (so as to allow, for example, an interventional cardiologist or the like to perform a portion of the procedure while separated from the radiation field of a fluoroscopy system), or input device 806 may be a user interface integrated into the hand-held driver, or both. Preferably, the valve manifold 808 will comprise one of the modular plate manifold structures described herein, and will be contained within the hand-held driver unit 804. Canister 810 may be affixed to the driver (directly or by coupling of the catheter to the driver), and will often be included within a hand-held proximal assembly of deployment system that includes the driver, the proximal interface of the catheter, and other proximal components of the catheter (such as the heart valve actuation or deployment device 813, or the like) during use. Similarly, a battery of the system (not shown) may be integrated into the driver 804, may be mounted to the proximal interface of the catheter, or both.

A catheter 812 or other elongate flexible body for use with driver 804 will generally have a proximal interface 814 that mates with a receptacle 816 of the driver. As can be understood with reference to the descriptions above, the mating of the proximal interface with the receptacle will often provide sealed fluid communication between a balloon array of the catheter and the valves of the manifold assembly. Coupling of the proximal interface with the receptacle may also result in coupling of electrical contacts of the driver 818 with electrical contacts of the catheter 820, thereby facilitate access to internal shape sensor data, external localization data (which may employ a powered fiducial on the catheter and an external electromagnetic sensor system, or the like). Still further communications between the catheter and the driver may also be facilitated, including transmission of catheter identification data (which may include a catheter type for configuration of the controller, a unique catheter identifier so as to help inhibit undesirable and potentially deleterious re-use of the catheter, and the like). As an alternative to (or in addition to) electrical communication of this data, catheter 812 may have an RFID, bar code, or other machine-readable tag on or near proximal interface 814, and driver 804 may include a corresponding reader one or near receptacle 816.

Referring to FIGS. 27 and 28, the input device 806 and/or input sensors associated with processor board 802 may also be used to generate processor mode signals, for example, to switch between any of the system modes described herein. Input device 806 may, for example, include a mode button or switch which allows the mode of the processor to be selected from among a group of modes such as a manual movement mode, an automated movement mode, a follow-the-curve mode, an axial recovery mode, any of the other operational modes described herein (or any subset thereof). In some embodiments, the processor mode may change in response to sensor signals. For example, in response to a movement sensor indicating that a proximal housing containing the manifold or the like is being manually moved with a movement above a threshold (such as a movement that is sufficient to be transmitted distally along the catheter body into the patient), the processor may change from an automated movement mode to a manual movement mode. This may allow, for example, the system user to manually reposition the catheter without having to wait to input a mode command. The system may, in response to mode change command or sensor signal associated with the beginning of a manual repositioning of the distal portion of the catheter, identify a pre-move position of the distal portion of the catheter. The system can also identify a post-move position of the distal portion, and can use the difference between the pre- and post-move positions to update a transformation between the input and the output so as to maintain coordination for the user. Optionally, sensed movements of the proximal housing may be used during manual movement to derive articulation commands, such as by sensing axial movement of the housing so as to estimate axial movement of the catheter body through the introducer sheath (instead of or in addition to measuring relative motion between the introducer and catheter) for calculating lateral deflection axial propagation when in a follow-the curve mode.

Figure 29A:
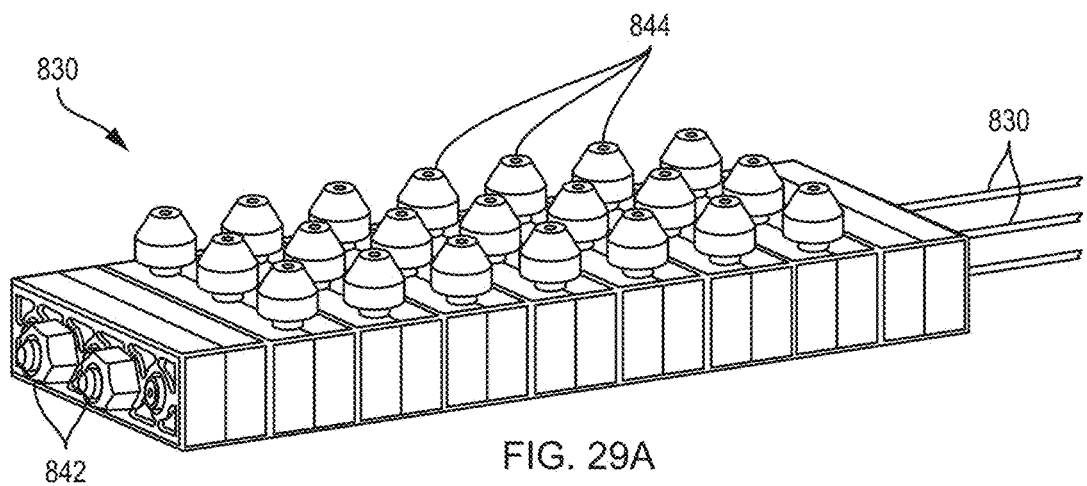
FIGS. 29A-30 illustrate an alternative interface for coupling a modular fluid manifold to a plurality of multi-lumen shafts so as to provide control over articulation of a catheter along a plurality of segments, each having a plurality of degrees of freedom, along with portions of some of the plate modules of the manifold, with the plate modules here having a receptacle member that helps couple the layers of the plates to posts of the interface.
Figure 29B:
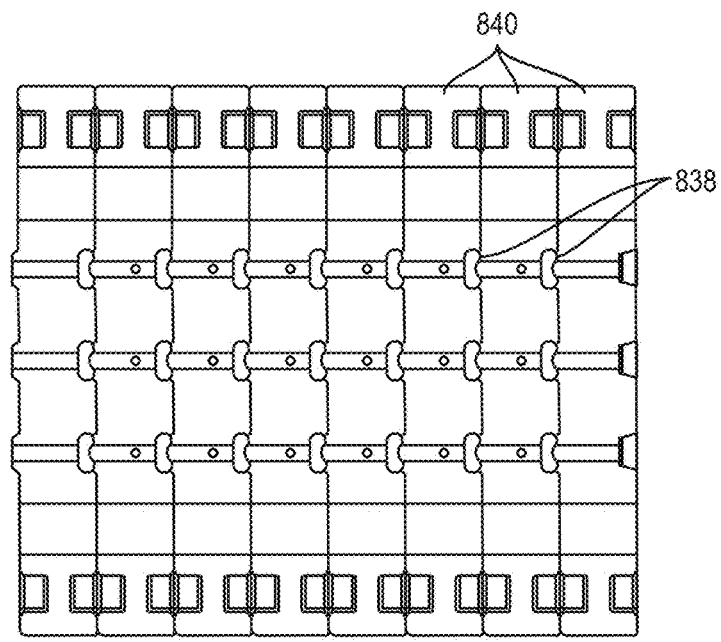
Figure 29C:
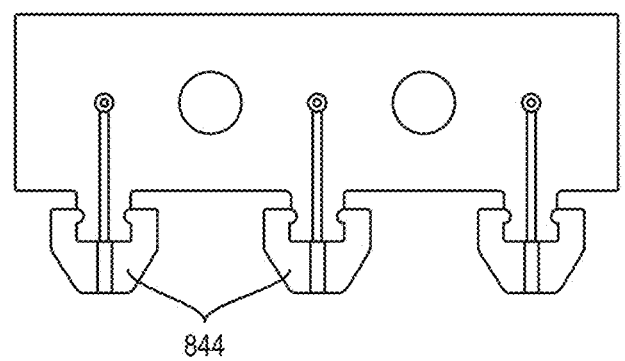
Figure 30:
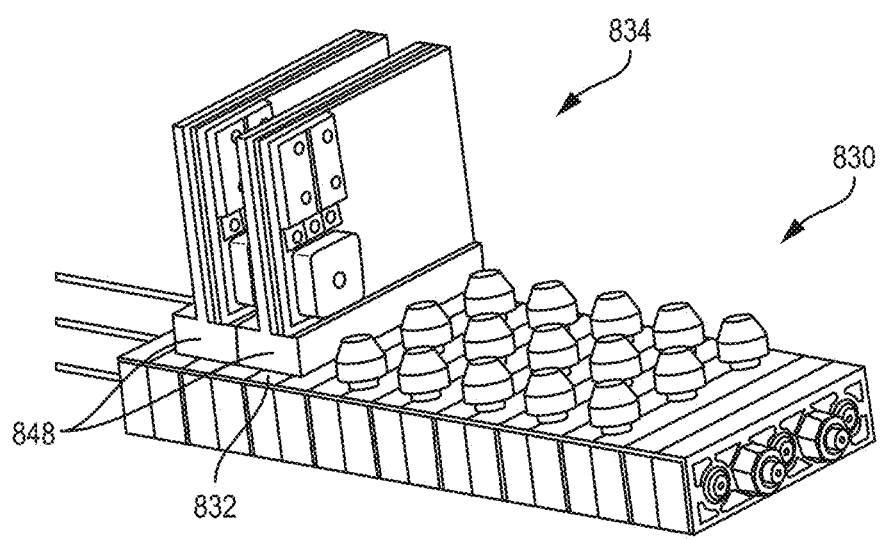

Referring now to FIGS. 29A-30, an alternative proximal interface 830 of the catheter can be understood, along with how it can be mated to an alternative receptacle 832 of an alternative modular manifold 834. Proximal interface 830 provides sealed communication between axially separated ports of up to three multi-lumen shafts 836, with the ports of the multi-lumen shafts being sealed by axially compressing O-rings 838 or other deformable sealing bodies interleaved between more rigid interface members 840. Threaded compression members 842 maintain axial sealing compression between a proximal-most interface member and a distal-most interface member. Posts 844 of interface members 840 extend laterally and parallel to each other. Each interface member 840 includes a post 844 for each multi-lumen shaft, and the number of interface members included in proximal interface 830 is the same as the number of independently used lumens in each multi-lumen shaft, so that the posts form an array with the total number of posts being equal to the total number of independent multi-lumen channels in the articulated structure. Lumens extend radially from the ports of the multi-lumen shaft, through the posts 844, and to an interface port surrounded by a cap of deformable seal material.

Referring to FIG. 30, receptacle 832 of manifold assembly 834 has a series of indentations that correspond with posts 844 of proximal interface 830. The indentations have surfaces that correspond to the posts and seal to the deformable caps with the interface ports each in sealed fluid communication with an associated channel of an associated plate module. In this embodiment, the receptacle surfaces of each plate modules is on a receptacle member 848. The receptacle members support plate layers with channels formed between the layers, with MEMS valves and pressure sensors mounted to the plates as described above. Here, however, the plates of adjacent plate modules may not be in direct plate-plate contact, so that the supply and exhaust flows may extend axially through the receptacle members, through the proximal interface, or through another structure of the manifold assembly.

Figure 30A:
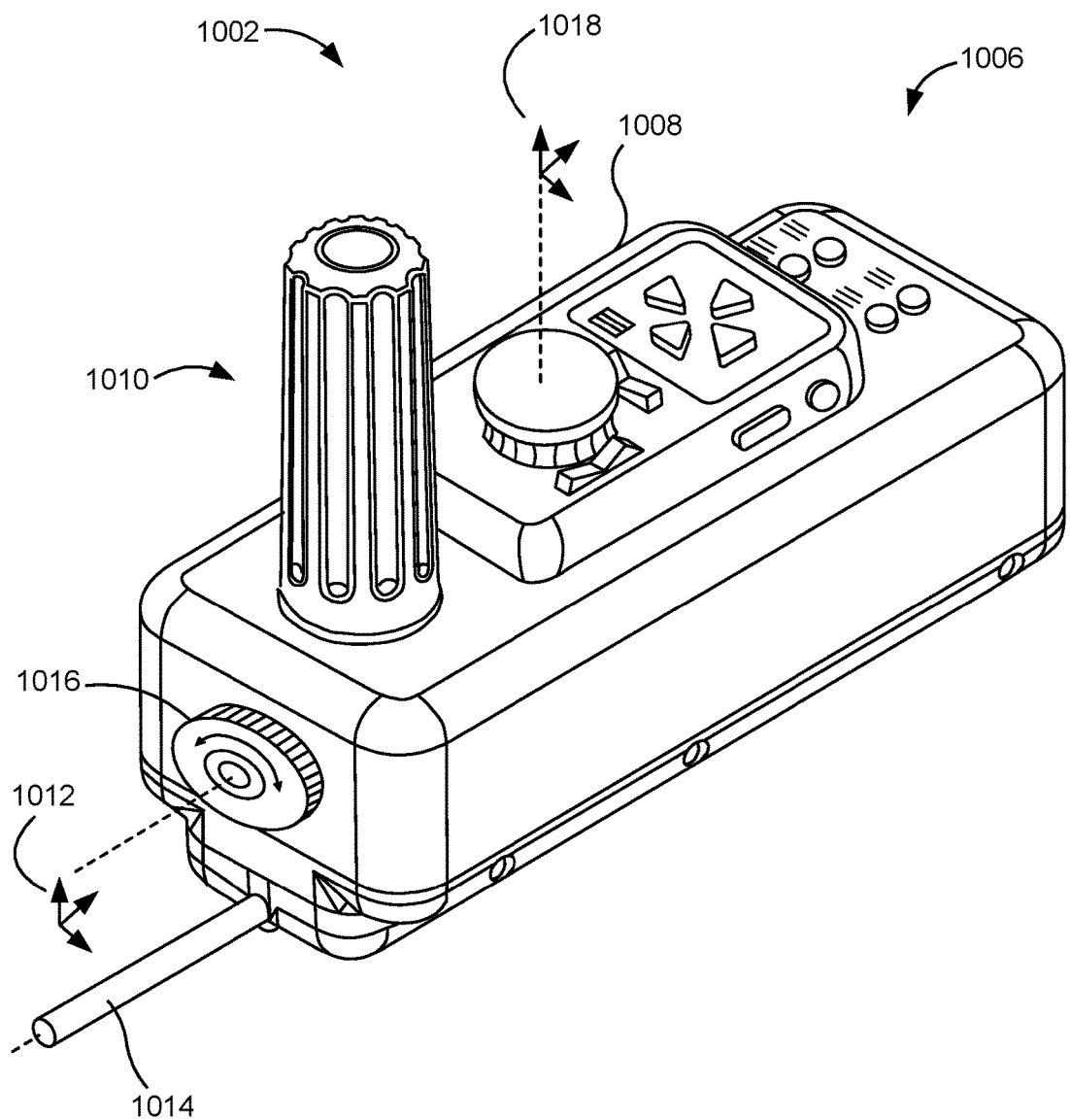
FIGS. 30A and 30B illustrate alternative housings containing fluid manifolds, along with an exemplary input mountable to a manifold housing.
Figure 30B:
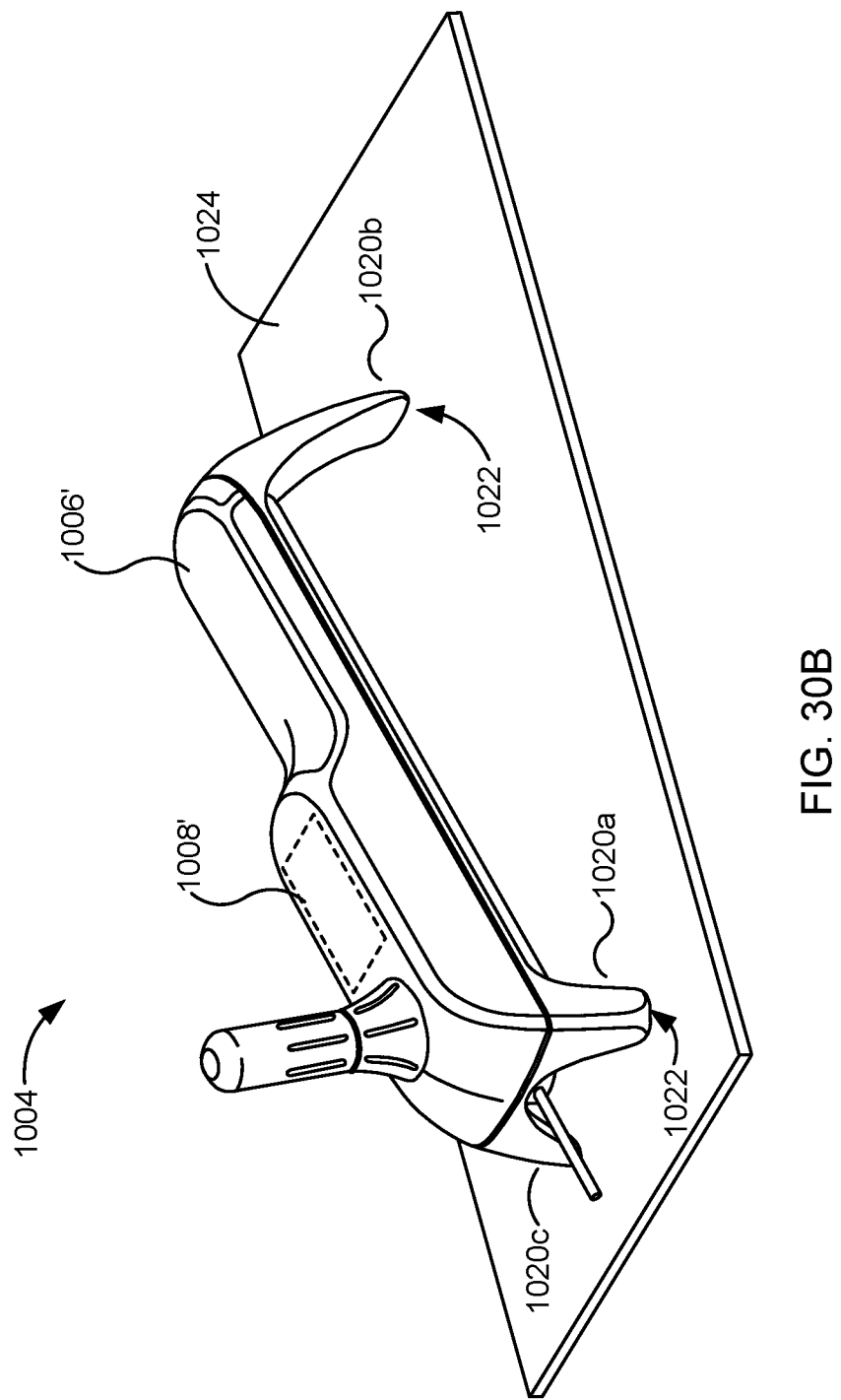

Referring to FIGS. 30A and 30B, exemplary alternative proximal housings 1002, 1004 are shown. Proximal housing 1002 here includes a manifold housing 1006 and an input housing 1008, with the input housing optionally releasably mountable onto the manifold housing, typically using quick disconnect mechanical couplers, electrical/mechanical connectors, magnetic and/or magnetically guided couplers, or the like. Alternative systems may have the input and manifold housings integrated or permanently affixed together, or separate structures (either or both optionally being separately mountable to a base station). When detachable, the manifold housing 1006 and input housing 1008 may each contain associated components of the processor system (such as one or more manifold PCB board for the manifold housing, and one or more user interface board for the input housing) and a battery or other power source. The user interface processor components of input housing 1008 can optionally be coupled with the processor components of the manifold by wireless telemetry when separated; if/when the input is releasably mounted to the manifold, data and power may optionally be transmitted between the processor components included in the two different housing via a detachable coupler that engages when the housings are mated together.

Referring to FIG. 30A, manifold housing 1006 is coupled to flexible catheter 1014 via a detachable catheter coupler or base, and a disposable pre-pressurized gas/liquid inflation fluid canister 1010 is also detachably supported by the manifold housing. Manifold housing 1006 has an associated manifold reference frame 1012 and is configured to be held in space by a hand of the system user while the user inputs movement commands using the hand holding the manifold and/or the other hand. The user holding manifold housing 1006 may also manually manipulate the distal end of the catheter by axially moving the catheter through the insertion sheath and in/out of the patient body, optionally (at least in part) using the hand holding the manifold housing by moving the manifold housing toward and away from the patient. The user may also rotate the manifold about the axis of the catheter so as to manually rotate the distal end of the catheter. As keeping an axis of the canister within a range of angles from upright may facilitate steady flows of inflation fluid, a twist input 1016 may be mounted to manifold housing 1006 with the twist input configured to receive rotational input about a twist input axis 1018 that extends along the axis of the catheter adjacent the manifold. In response to this twist input, the processor may be configured to articulate the catheter so that one, some, or all bends of the articulatable distal portion of the catheter precess about the distal catheter axis, with the precess angles corresponding to a twist angle input. This may allow the user to manually use a combination of axial movements of the catheter with twist in a manner analogous to manipulation of an unarticulated guide catheter or the like with much better torsional correlation between the input and output, with less torsional whipping, and the like. As can be more fully understood with reference to FIGS. 32A-35E and the associated text, gross movement of manifold housing 1006 in the hand of the user may be sensed and used as an input for catheter articulation, with movement sensing optionally being provided by sensors supported by the manifold housing itself, by sensors supported by the input housing while the input housing is mounted on the manifold housing, or by both.

Referring still to FIG. 30A, when separable housings are provided, while selected components of the user interface (input, display, sound, etc.) may optionally be mounted to manifold housing 1006, movement command input components may be primarily or entirely supported by input housing 1008. Input housing 1008 may include, for example, a joystick and/or trackball for entry of movement commands in a plurality of degrees of freedom, with an exemplary input having an at least 3D joystick (and ideally a 6D joystick) configured to receive movement commands in some or all of input roll, pitch, yaw, along with X, Y, and Z translation (all in an input reference frame 1018. Suitable 6D joysticks may be commercially available from 3Dconnexion (including the SpaceNavigator™ 3D motion controller) and other suppliers, and such 3D input devices may be particularly well suited for providing movement commands as velocity (translation and/or rotation) input vectors. Gross movement of the input housing may be well suited for providing positional (translation and/or rotation) input vectors. Additional or alternative user interface components may include buttons associated with articulation orientations, toggle switches for adjusting input/output orientation(s), a touch screen, a clutch button, a processor mode button, a display, a touch screen, and/or the like. To help align input vectors with output motion vectors of the articulated catheter, the user may at least roughly align input housing 1008 (and/or manifold housing 1006) with the gross anatomy of the patient, with the internal tissue of the patient targeted for treatment (optionally as that tissue is shown in a display), or with a distal portion of the catheter (optionally as shown in a display). Toward that end, input housing 1008 may be elongate (to facilitate axial alignment between the input and the elongate articulated catheter distal portion) and have visual and/or tactile features that differentiate the input proximal, distal, vertical, and lateral orientations (such as one or more axially offset user interface components and differentiated vertical thickness and lateral width). Some or all of the user interface components, the wireless telemetry circuitry, the sensor structures, the processor components, the battery, and/or the like of input housing 1008 may be commercially available for or adapted from those of standard smart phones and other consumer mobile computing devices.

Referring to FIG. 30B, proximal housing 1004 includes an alternative manifold housing 1006' and will typically include a user interface 1008'. User interface 1008' may include user interface components of the input housing 1008 described above, which may be integrated into manifold housing 1006', or may be supported by an input housing detachably mountable on manifold housing 1006' or kept separate. Manifold housing 1006' has legs 1020a, 1020b, 1020c, with the bottom surfaces 1022 of the legs together defining a base surface that is stabile on a flat support surface 1024. The bottom surface of the legs support the catheter above the support surface and orient the catheter adjacent the manifold so that the axis of the catheter angles distally downward toward an introducer sheath. Support surface 1024 will typically comprise the top of a small (less than 0.5 square meter), generally horizontal table that can be cantilevered over the patient, with the table either supported by lockable wheels or being mountable to a side-rail of the operating table. Advantageously, the user can manually manipulate the catheter by grasping and moving the catheter body distal of the manifold housing 1006', and/or by grasping and moving manifold housing 1006'. Axial manual movement of the catheter shaft through the introducer sheath can be accommodated by axial sliding of bottom surfaces 1022 over the flat surface. Flexing of the catheter body between the proximal housing and input sheath may accommodate any change in angle associated with the sliding movement, and/or the flat surface may optionally be tilted downward distally (toward the insertion sheath and the angle of the catheter body near the proximal housing, allowing more even leg lengths) to decrease proximal bending of the catheter with axial movement. Rotation of a twist input 1016 (see FIG. 30A) mounted to housing 1006' near the catheter can mimic manual rotation of the catheter shaft, or the user can lift and manually rotate the manifold housing and catheter shaft. Still further alternative arrangements may be provided, including stand systems that hold the manifold and allow rotation about the catheter axis, catheter/manifold couplers that accommodate relative rotation, and the like. Regardless, the user can readily alternate between manual advancement and other manipulation of the catheter within the patient body and automated manipulation of the distal articulated portion of the catheter within the patient using the drive system that is contained entirely within housing 1006' and the catheter mounted thereon. Optionally, the processor may switch between automated and manual modes in response to movement sensors mounted to manifold housing 1006' (optionally by mounting of an input housing thereon). Related articulated catheter systems may have similar user interface capabilities but quite different drive systems, including catheter systems having pull-wires actuated by electrical motors (optionally with no fluid manifold in the proximal housing) or by syringe pumps pistons driven using fluid inflation/deflation valves and a gas/liquid canister similar to those described above. When separable input and drive system housings are provided, once the catheter is generally in position the user may move input housing 1008' to a desired location so as to, for example, limit user orthopedic strain and/or exposure to radiation from fluoroscopic or other imaging systems.

Referring now to FIGS. 31A-31D, an alternative balloon-articulated structure 850 having a single multi-lumen core may be particularly well suited for smaller profile applications, such as for microcatheters having sizes down to 2 or 3 Fr, guidewires, or the like. Articulated structure 850 generally has a proximal end 852 and a distal end 854 and may define an axis therebetween. A frame 856 of the structure is shown by itself in FIG. 31C and is generally tubular, having a series of loops 858 interconnected by axial struts 860. Two struts may be provided between each pair of adjacent loops, with those two struts being circumferentially offset by about 180 degrees; axially adjacent struts between nearby loop pairs may be offset by about 90 degrees, facilitating lateral bending of the frame in orthogonal lateral bending orientations. As will be understood from many of the prior frame structures described herein, apposed surface region pairs between loops 858 will move closer together and/or farther apart with lateral bending of frame 850, so that a balloon can be used to control the offsets between these regions and thereby the bending state of the frame.

Figure 31A:
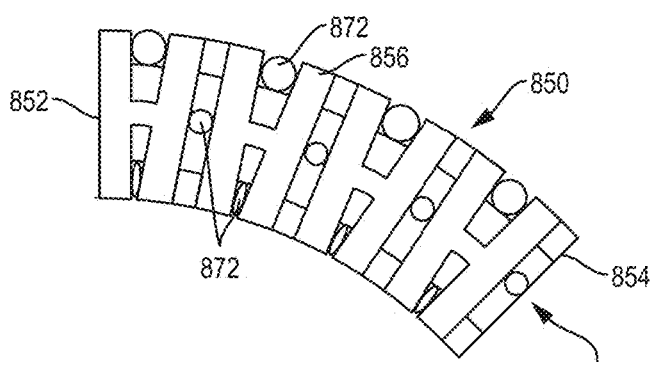
FIGS. 31A-31D illustrate an alternative articulatable structure having a single multi-lumen core with balloons extending eccentrically from the core, along with details of the structure's components and assembly.
Figure 31B:
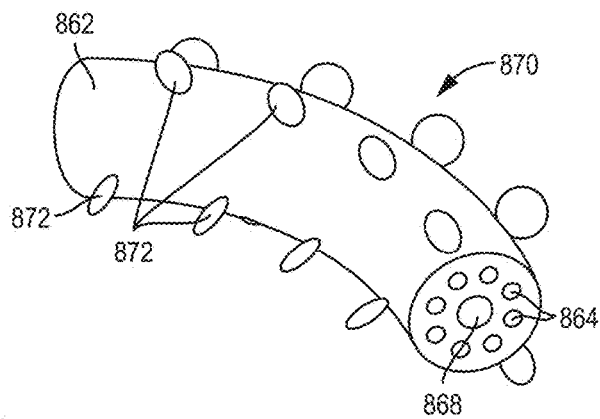
Figure 31C:
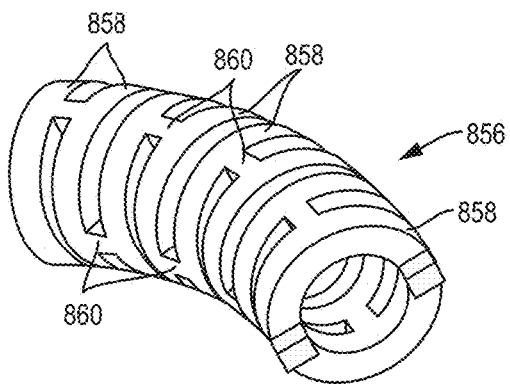
Figure 31D:
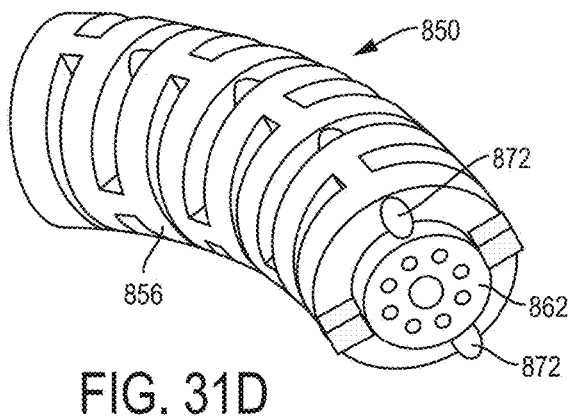

A multi-lumen core 862 is shown by itself in FIG. 31B, and extends axially within the lumen of frame 856 when used (as shown in FIG. 31D). Core 862 includes a plurality of peripheral lumens 864 surrounding a central lumen 868. Central lumen 868 may be left open as a working channel of articulated structure 850, to allow the articulated structure to be advanced over a guidewire, for advancing a guidewire or tool through the articulated structure, or the like. An array 870 of eccentric balloons 872 is distributed axially and circumferentially about the multi-lumen core, with the array again taking the form of an M×N array, with M subsets of balloons being distributed circumferentially, each of the M subsets being aligned along a lateral bending orientation (M here being 4, with alternative embodiments having 1, 2, 3, or other numbers of circumferential subsets as described above). Each of the M subsets includes N balloons, with N typically being from 1 to 20. The N balloons of each subset may be in fluid communication with an associated peripheral lumen 864 so that they can be inflated as a group. Eccentric balloons 872 may optionally be formed by drilling ports between selected peripheral lumens 864 to the outer surface of the body of the core, and by affixing a tube of balloon wall material affixed over the drilled body of multi-lumen core 862, with the inner surface of the balloon tube being sealingly affixed to an outer surface of the multi-lumen body of the core. Alternatively, eccentric balloons may be integral with the multi-lumen core structure, for example, with the balloons being formed by locally heating an appropriate region of the multi-lumen core and pressurizing an underlying lumen of the core to locally blow the material of the multi-lumen body of the core radially outwardly to form the balloons. Regardless, the balloons extend laterally from the body of the multi-lumen core, with the balloons optionally comprising compliant balloons, semi-compliant balloons, or non-compliant balloons. The shape of the inflated balloons may be roughly spherical, hemispherical, kidney shaped (curving circumferentially about the axis of the core), cylindrical (typically with a length:diameter aspect ratio of less than 3:1, with the length extending radially or circumferentially), or some combination of two or more of these.

When multi-lumen core 862 is assembled with frame 856 (as in FIGS. 31A, 31C, and 31D), the body of the multi-lumen core is received in the lumen of the frame and balloons 872 are disposed between the apposed surfaces of loops 858. By selectively inflating one subset of balloons 872 aligned along one of the lateral bending orientations, and by selectively deflating the opposed subset of balloons (offset from the inflated balloons by about 180 degrees), the axis of articulatable structure 850 can be curved. Controlling inflation pressures of the opposed balloon subsets may vary both a curvature and a stiffness of articulatable structure 850, with increasing opposed inflation pressures increasing stiffness and decreasing opposed inflation pressures decreasing stiffness. Varying inflation of the laterally offset balloon sets (at 90 and 270 degrees about the axis, for example) may similarly variably curve the structure in the orthogonal bending orientation and control stiffness in that direction. The profile of the single-core assembly may be quite small, with an exemplary embodiment having an outer diameter of frame 856 at about 1.4 mm, an outer diameter of the body of multi-lumen core 862 of about 0.82 mm, and an inner diameter of the peripheral lumens 864 of about 0.10 mm. The multi-lumen core body and balloons may comprise polymers, such as any of the extrusion or balloons materials described above, and the frame may comprise a polymer or metal structure, the frame optionally being formed by molding, cutting lateral incisions in a tube of material, 3D printing, or the like. Note that the exemplary multi-lumen core structure includes 8 peripheral lumens while the illustrated segment makes use of 4 lumens to articulate the segment in two degrees of freedom; a second segment may be axially coupled with the shown segment to provide additional degrees of freedom, and more lumens may be provided when still further segments are to be included.

Figure 32A:
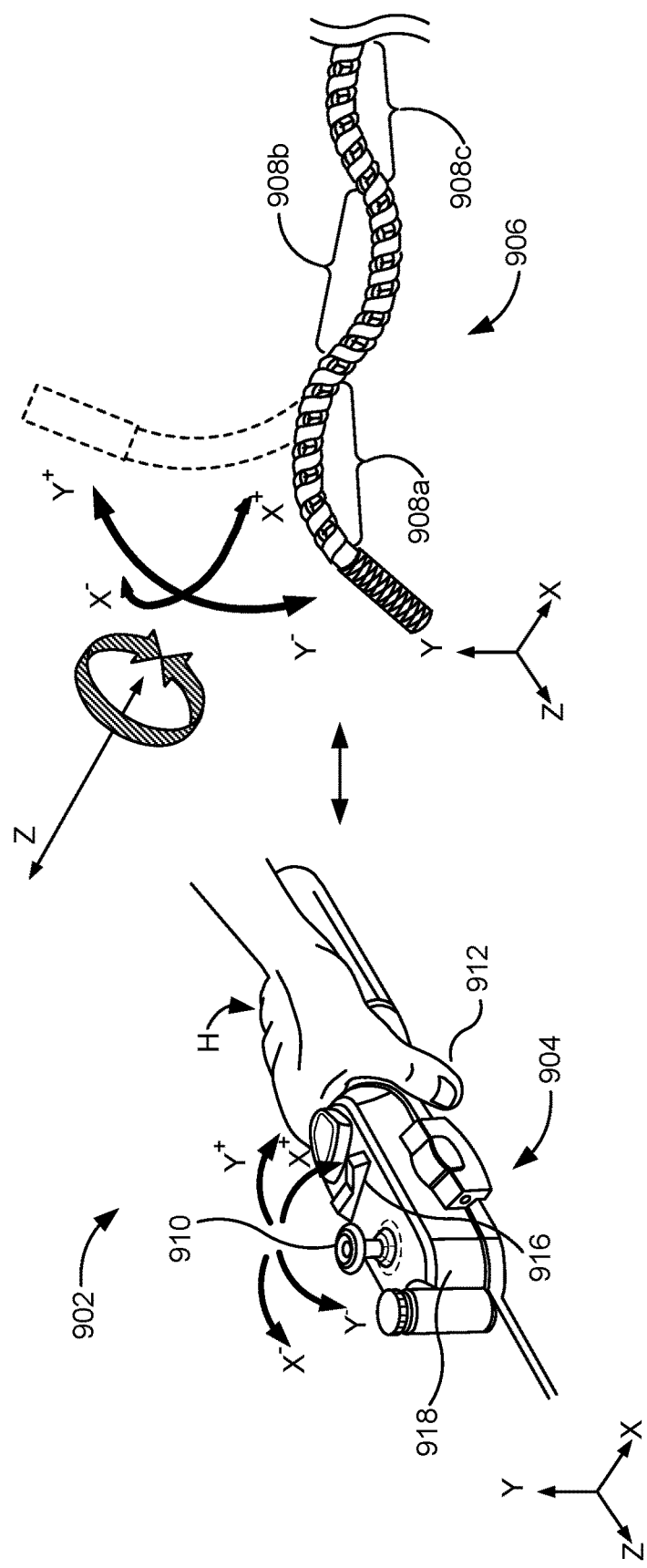
FIGS. 32A and 32B illustrate a hand-held housing having a joystick and how a movement command can be input by the hand holding the housing by manipulating the joystick with a thumb of hand, and also schematically illustrate rotational alignment of the movement command with the distal portion of an articulated catheter about the axis of the catheter.

Referring now to FIG. 32A, an articulation system 902 includes a housing input device 904 and an articulated catheter 906 having 3 independently articulatable segments 908a, 908b, 908c. Each segment may have 3 articulated degrees of freedom, including lateral bending in X and Y orientations, and axial elongation in a Z orientation. To control lateral bending of, for example, a distal segment 908a, housing input device 904 may, for example, have an X-Y joystick 910 that is configured to be manipulated by a thumb 912 of a hand H that is holding the housing input device. Ease of use of the input device may be enhanced by alignment between the X-Y joystick 910 and the X-Y articulation of the catheter 906 that is induced by movement of the joystick. The preferred alignment is between the movement command as entered into the input device and the resulting automated movement of segment 908a, 908b, and/or 908c, per the perception of the surgeon, so that the relationship is comfortable or intuitive. The surgeon may primarily perceive movement at the distal end of the catheter from an image obtained by way of fluoroscopy (or some other remote imaging modality) and displayed to the surgeon on a screen or other display device. The desired alignment is typically not directly associated with a true alignment between the catheter tip and the input device, so that the actual orientation of the catheter tip and input device may be at any relative angle. The perception of orientation is related to the relative orientation of the monitoring or imaging field (aka. monitor and camera position/angle) and to the display of the catheter tip image to the surgeon. Suitable alignment may be achieved using a rotational alignment input 916 to electronically rotate the X-Y lateral articulation axes of distal segment 908a, intermediate segment 908b, and/or proximal segment 908c about the Z or elongate axis of the distal segment. Segments 908a, 908b and 908c may be rotationally affixed together about the Z axis, so that providing alignment with any may achieve alignment with all three. Regardless, one or more additional joysticks or other input structures could be provided to provide control over the other degrees of freedom of articulated catheter 906. Alternatively, input for at least some articulation degrees of freedom may be provided by moving a housing 918 of housing input device 904 with hand H, significantly simplifying the user interface and allowing a single hand of the user to provide intuitive input commands for 3, 4, 5, 6, 7, or even 8 (for example, with the inclusion of X-Y joystick 910 or the like) or more articulated degrees of freedom of catheter 906, the articulated degrees of freedom sometimes called the degrees of freedom in joint space.

Figure 32B:
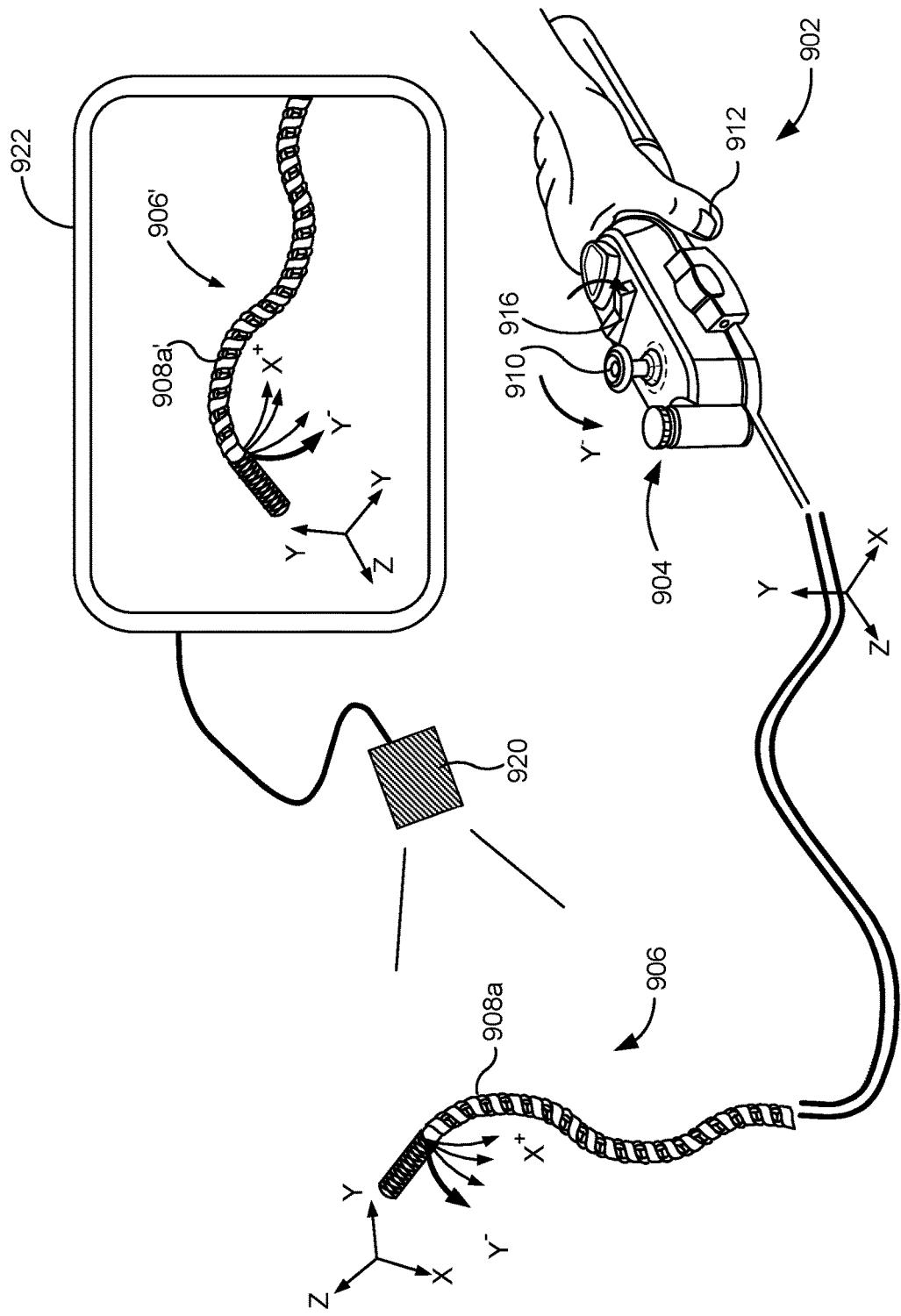

Referring now to FIG. 32B, and here addressing the rotational alignment of joystick 910 using rotational alignment input 916, an image capture device 920 such as fluoroscopy system, MRI system, computer tomography system, ultrasound system, infrared or optical camera, or the like may obtain an image of at least a distal portion of catheter 906. An image 906' of catheter 906 (including an image 908a' of distal segment 908a) may be shown on a display 922, with the user generally directing movement of the catheter with reference to the images of the catheter and adjacent tissue structures as shown in the display. As image capture device 920 may be at a different orientation than the user relative to the catheter and tissue structures, and as the display may be at a still different orientation than both, absent alignment structures an input command in a desired orientation (for example, in the Y− orientation) may result in a displayed articulation of distal segment 908a in an arbitrary orientation (for example, in the X+ orientation).

A variety of components and approaches can be included to improve input/output correlation. Catheter image 906' will generally have an elongate shape and a visible distal end, and gross correlation between input housing device 904 and the image of the catheter may optionally be provided by an elongate shape of the housing input, and in some cases by having the user manually orient the housing so that the elongate shape of the housing roughly corresponds with an orientation of the catheter shown in the display. Manually establishing alignment may be facilitated by an elongate image of the distal portion of the catheter (so that an orientation of the axis of the catheter can be visually identified, optionally with reference to a recognizable distal catheter end), along with the elongate input housing shape (so that the axis of the input housing can be readily identified and manually rotated into alignment with the catheter axis in the image, optionally with reference to a tactile differentiation between the proximal and distal ends of the input). Such manual alignment may be analogous to the aligning of a computer mouse with a display, and the alignment may be revised after manual or automated movements of the catheter. Alternative automated alignment systems may make use of FBG or other catheter shape sensors, image capture and/or image processing software (such as that used in the EchoNavigator™ system commercially available from Phillips or others for fusing ultrasound and fluoroscopic image data), surgical navigation systems (including the StealthStation™ system from Medtronic or other systems having electromagnetic localization components), and the like. Regardless, rotational correlation between the articulations of distal segment image 908a' and joystick 910 may optionally be provided, enhanced, or confirmed by making a series of small test articulation input commands (for example in the Y− orientation) to the joystick while holding housing 918 (see FIG. 32A) in a fixed orientation, observing the displayed orientation of distal segment 908a' articulation (for example, initially in the X+ orientation), and providing input corrective input by actuating rotational alignment input 916 (for example, resulting in incremental rotation of the lateral bending X-Y axes about the Z axis of catheter 906 and/or distal segment 908a (see FIG. 32A).

Note that absolute correlation between the input and output orientations need not be provided or sought, as rough correlation may be sufficient to allow intuitive operation of the system 902. Note also that a variety of alternative input and adjustment inputs or mechanisms may be provided, including using trackballs, touchpads, joysticks, or a variety of alternative X-Y articulation input devices; using thumbwheels, toggles, slides, or a variety of alternative rotational alignment inputs; and/or using image recognition or relative position information regarding the display and input housing to calculate transforms that provide the desired input/output rotational correlation. It should be understood that the X-Y articulation that may be electronically rotated about the Z axis of the catheter need not involve any actual rotation of the various articulation balloons or other articulation structures; typically, the mathematical transforms of the controller and/or valve drivers will simply be revised so that alternative balloon subsets will be inflated to generate lateral bending in differing orientations (though mechanical rotation may be used in some embodiments). It should also be understood that the correlation between the lateral bending orientations may, in some input control configurations, be altered by roll 926 of housing 918, while the correlations may not be altered with others. For example, moving the whole control body or housing as a means of control may help align command/visual axes. However, in some embodiments (including integrated manifold/input embodiments having a pre-pressurized liquid/gas canister) it may be desirable to maintain the input in an upright orientation. In such embodiments that also have rollers or a joystick mounted on the controller, repositioning of the controller housing may not coordinate or be intuitive with the catheter tip, and/or it may be awkward to reach or handle the inputs at these other physical orientations.

Figure 33A:
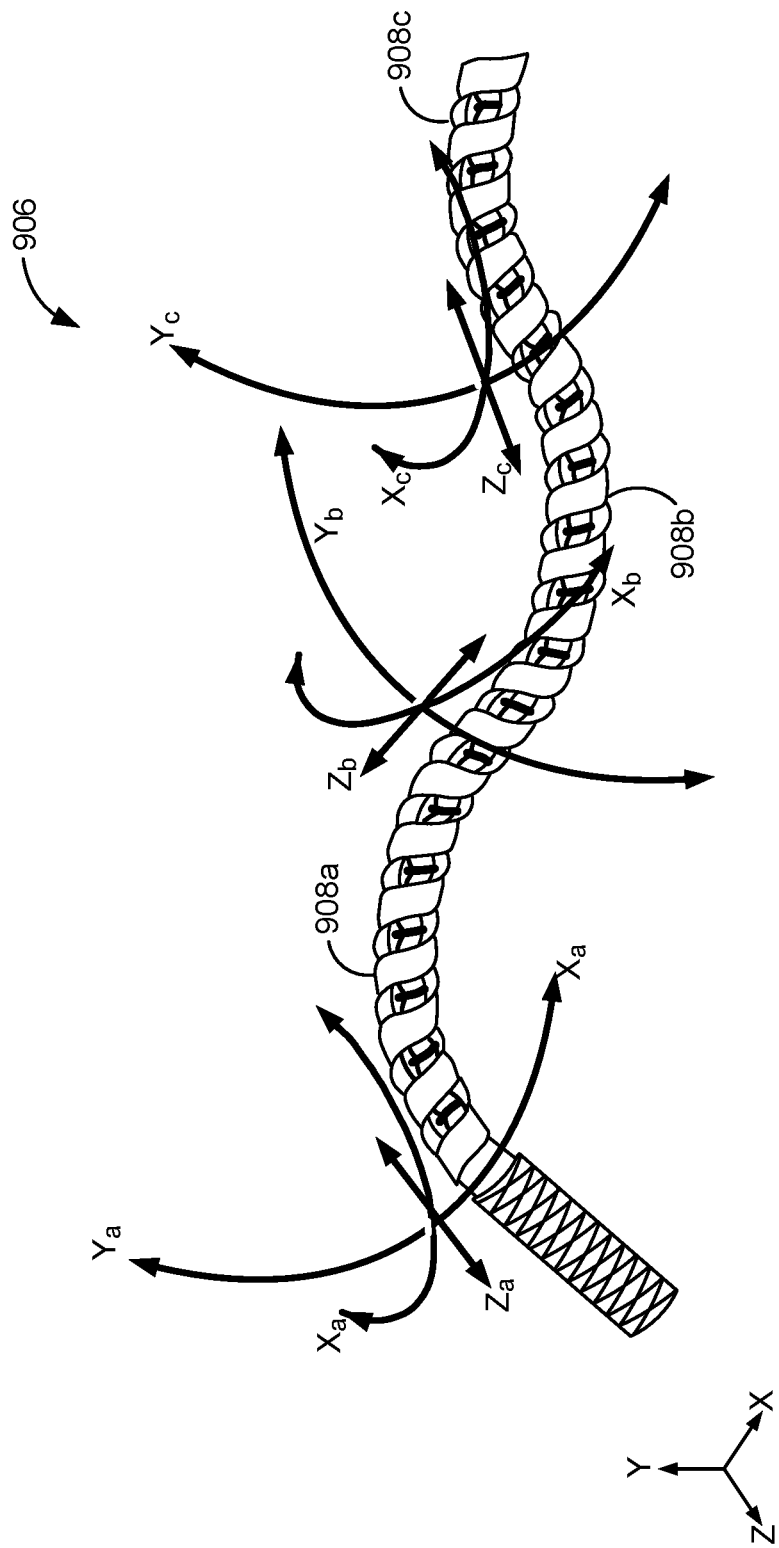

Referring now to FIG. 33A, regardless of how the user interacts with the system to achieve lateral bending of distal segment 908a, it will be beneficial to include user interface components which help take advantage of the enhanced dexterity of the system that is available from the large numbers of degrees of freedom provided by flexible elongate articulated structure 906. More specifically, distal segment may be configured to provide lateral bending in Xa and Ya orientations, along with axial elongation in a Za orientation, thereby allowing articulation in 3 degrees of freedom. Intermediate segment 908b may similarly be configured for articulation in Xb, Yb, and Zb orientations, while proximal segment 908c may be configured for articulation in Xc, Yc, and Zc orientations. Other segments may provide additional degrees of freedom. For 3 segment catheter 906, where each segment has 3 degrees of freedom, a joystick (or other X-Y input) that receives movement commands for lateral bending of the distal segment may be helpful, but the system may benefit from additional input mechanisms. Table 2 is a partial top-level mapping of input and articulation degrees of freedom of input housing system 902, which may be helpful for identifying additional input structures and techniques.

TABLE 2

| INPUT | | OUTPUT | |
|---|---|---|---|
| Joystick | Xjoystick | Xa | Segment A |
|  | Yjoystick | Ya |  |
| Housing |  | Za |  |
|  |  | Xb | Segment B |
|  |  | Yb |  |
|  |  | Zb |  |
|  |  | Xc | Segment C |
|  |  | Yc |  |
|  |  | Zc |  |

While rotational alignment input 916 does provide an input for assisting alignment of the input command movements and displayed articulations, once alignment is established that input may not be used during active articulation. Fortunately, alignment of the orientation about the Z axis of the distal segment should also result in rotational alignment about the Z axes of the other segments (as all of the segments are rotationally coupled together, and can be substantially rotationally aligned), so that a single rotational alignment procedure may be sufficient. Regardless, as suggested by Table 2, it may be beneficial for movement of housing 918 of housing input device 904 to be used as an input for entering movement commands so as to generate articulation of catheter 906. It should be noted that there may (or may not) be more degrees of freedom in the articulated segments of the catheter than there are inputs from the user. Mechanical constraints from the tissue along the catheter may make use of some or all of these potentially excess degrees of freedom. Alternatively, the processor may use the available degrees of freedom to further one or more goal that improves system performance (such as minimizing drive fluid use, driving the system toward a state having desirable stiffness characteristics, minimizing non-anchoring tissue engagement forces, or the like). Suitable control arrangements for using the flexibility of kinematic systems having more than the minimum required degrees of freedom for a task often analyze the available alternatives that might fulfil a primary movement command as a null-space, and suitable controllers for taking advantage of the large numbers of the degrees of freedom that may be provided by the catheters described herein can be determined from public null-space control literature.

There are a wide variety of correlations that might be used to complete the mapping of Table 2, some of which are reviewed below. In general, however, housing 918 can be moved in H (an integer from 1 to 6) degrees of freedom to define input commands, and those H input degrees of freedom can be used to provide input movement commands for at least H articulation degrees of freedom of catheter 906.

For example, where the input command sensor system generates signals responsive to movement of housing H in 6 degrees of freedom, those 6 housing degrees of freedom may be used to calculate command movements for at least 6 articulation degrees of freedom. Additional input structures can be included on the housing or other input devices for articulation degrees of freedom that are not associated with movement of the housing (including joystick 910 or further additional input devices), or the controller may determine commands to take advantage of what might otherwise be excess or redundant degrees of freedom of the articulated structure. As a couple of simple examples, the processor may distribute axial elongation evenly among the segments, or may seek to maintain one or two of the segments in a nominal or mid-length configuration (in which lateral and/or vertical bending may be most nearly planar), or may maintain a position along the catheter with limited lateral displacement (such as to pass through the septal wall or the like).

Referring now to FIGS. 33B and 33C to review the six potential input degrees of freedom of housing 918, the orientational degrees of freedom include pitch 924 (here rotation about the X axis of housing input device 904), roll 926 (rotation about the Z axis), and yaw 928 (rotation about the Y or vertical axis). Translational degrees of freedom include axial translation along the Z axis 930, up or down translation along the Y axis 932, and lateral translation along the X axis 934.

Figure 34:
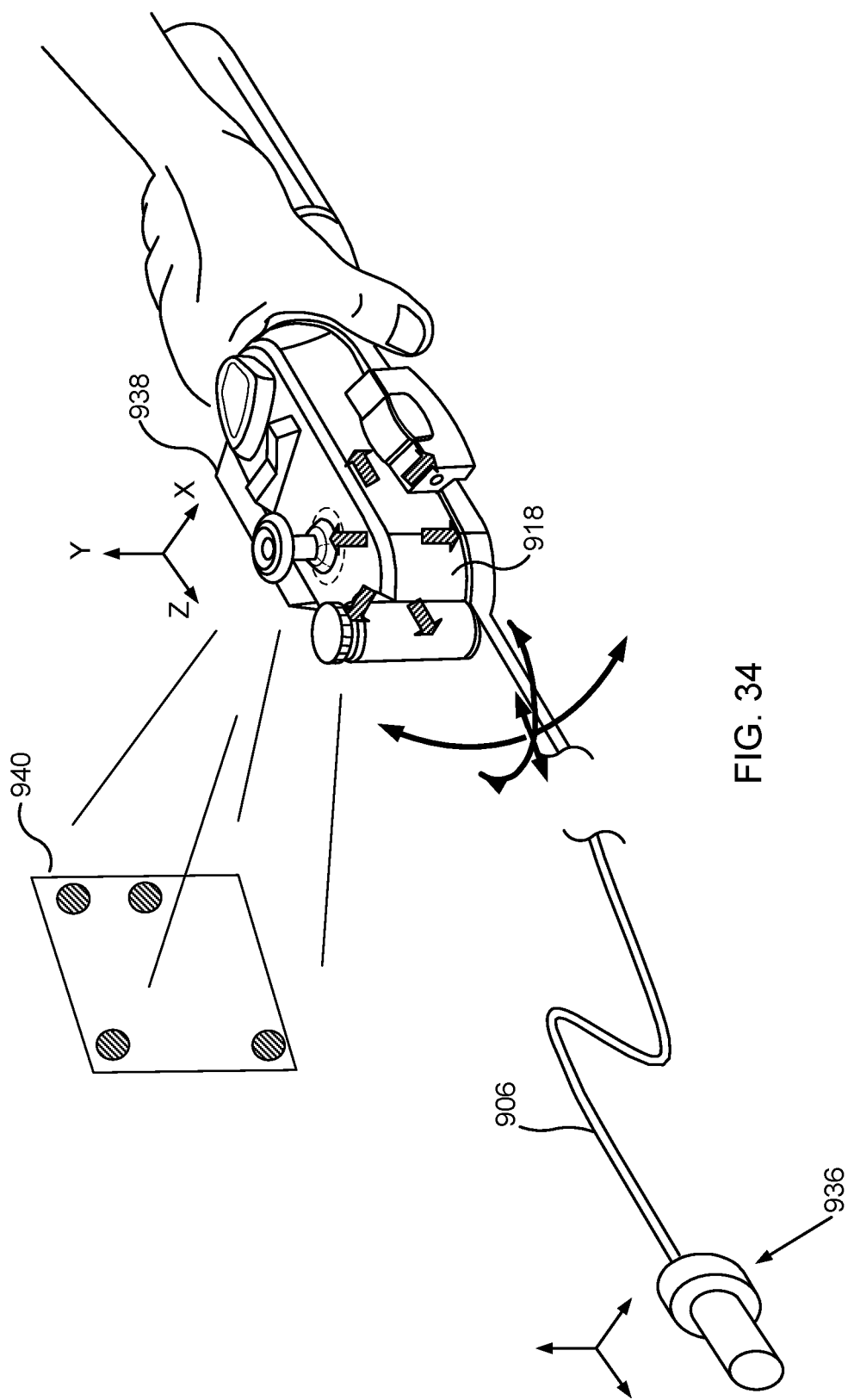
FIG. 34 schematically illustrates sensing of a movement of the input housing using an FBG sensor, an accelerometer, a gyroscope, and/or a camera.

Referring now to FIG. 34, a number of alternative sensor structures and systems may be used to generate signals indicative of movement of housing 918. As can be understood from the description above, a proximal portion of catheter 906 extending between housing 918 and an introducer sheath 936 (or the access site into the patient) may have a shape sensor such as a fiber Bragg grating (FBG), flexible electrical components printed on the structures of the catheter, or the like. Electromagnetic navigation structures may be included in the housing, or the housing may have markers (such as high-contrast spheres, printed QR codes, identifiable symbols, or the like) to facilitate optical localization of the housing using commercially available stereoscopic navigation systems. In some embodiments, most or all of the active components of the housing movement sensor system may be contained in the housing, for example, by including the FBG optical and processing components in the housing. As another example, rather than relying on external stereoscopic imaging for housing locations images, an image capture device 938 (such as a high definition camera, and infrared camera, a stereoscopic camera, or the like) may be mounted to housing 918, with the processor in the housing performing image processing to derive housing movement data. Suitable image capture devices may include the RealSense 3D camera system available from Intel, the Structure IO system available from Occipital, Inc., and the like. One or more reference marker 940 may be mounted at a fixed location to facilitate calculation of movement data using techniques similar to those developed and described for indoor navigation using cell phone image data. Other technologies developed for cell phones may be employed as a housing movement sensor, including MEMS accelerometers, MEMS gyroscopes, MEMS inertial navigation units (INU's), and the like. As some clinical settings for use of catheter 106 may have electromagnetic noise that could interfere with a magnetometer of an INU, it may be beneficial to adjust for drift of accelerometers and/or gyroscopes using data from a shape sensing FBG, an image sensor, or the like. Suitable signal processing for use in calculating a pose and/or movement of housing using data from MEMS sensors and image data may be found, for example, in one or more of the following references:

http://www.ncbi.nlm.nih.gov/pmc/articles/PMC4695469/
https://www.researchgate.net/publication/261267019_Indoor_navigation_system_using_image_and_sensor_data_processing_on_a_smartphone
http://www.doc.ic.ac.uk/teaching/distinguished-projects/2013/a.chandgadkar.pdf
http://www.google.com/patents/WO2014128507A2?cl=en
https://www.researchgate.net/publication/261551014_An_inertial_and_QR_code_landmarks-based_navigation_system_for_impaired_wheelchair_users A range of alternative motion sensing systems that have been well described in numerous references may be used, with many of the technologies being commercially available or readily assembled from open source components. Visual Odomotry (VO), Simultaneous Localization and Mapping (SLAM, including visual-inertial variants), fiducial and markerless camera pose tracking, inertial and optical data fusion, and the like have been well developed for augmented reality and other applications, and suitable analytical tools may be commercially available from Vicon, Kudan, and others, or obtained from the ARToolKit open source library or other sources, with many of these tools being suitable for use with sensors that are configured to be included in a mobile device such as a smartphone, tablet, or the like. Regardless, combining of data from a 1, 2, or 3 D accelerometer, a 1, 2, or 3 D gyroscope, a shape sensor coupled to catheter 906, and/or image capture device 938 can sense movement of housing 918 so as to receive 2, 3, 4, 5, or 6 movement command input degrees of freedom. The input degrees of freedom may include any one or more of the three orientational degrees of freedom, or any one or more of the three translational degrees of freedom, or both.

Figure 35A:
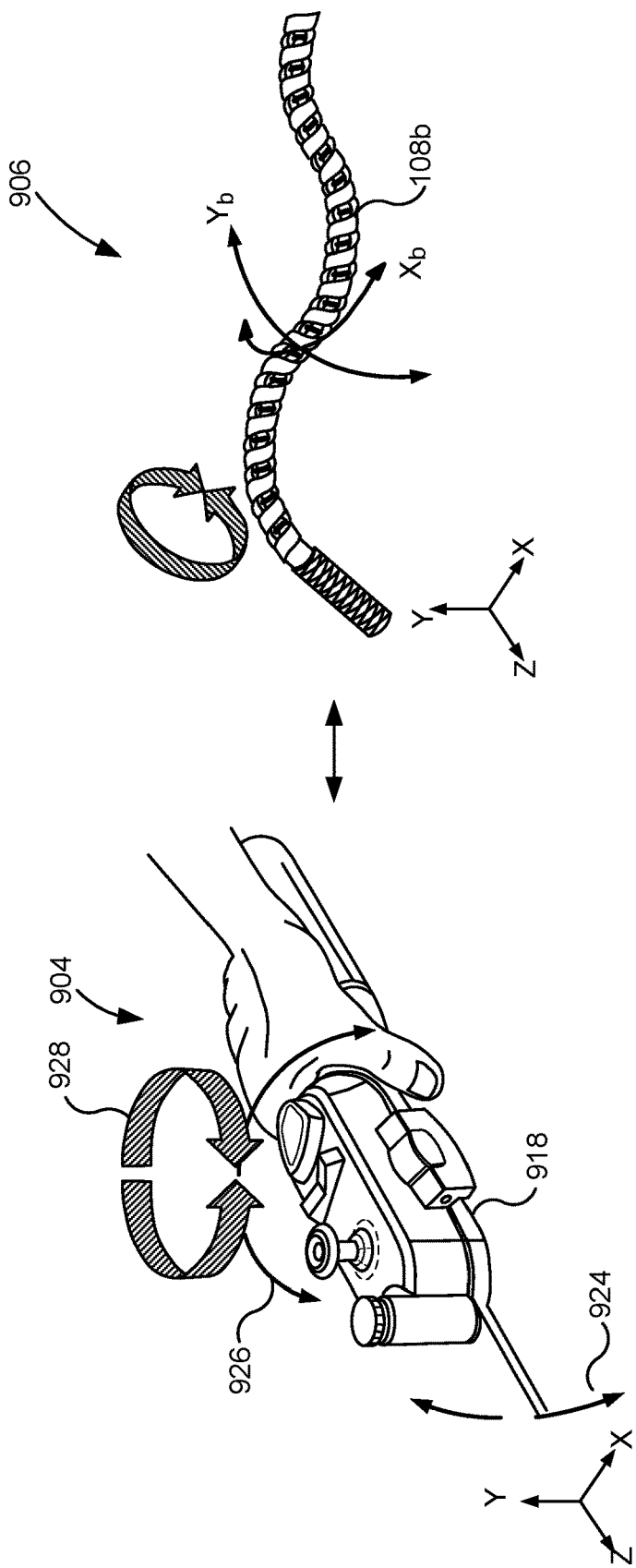
Figure 35B:
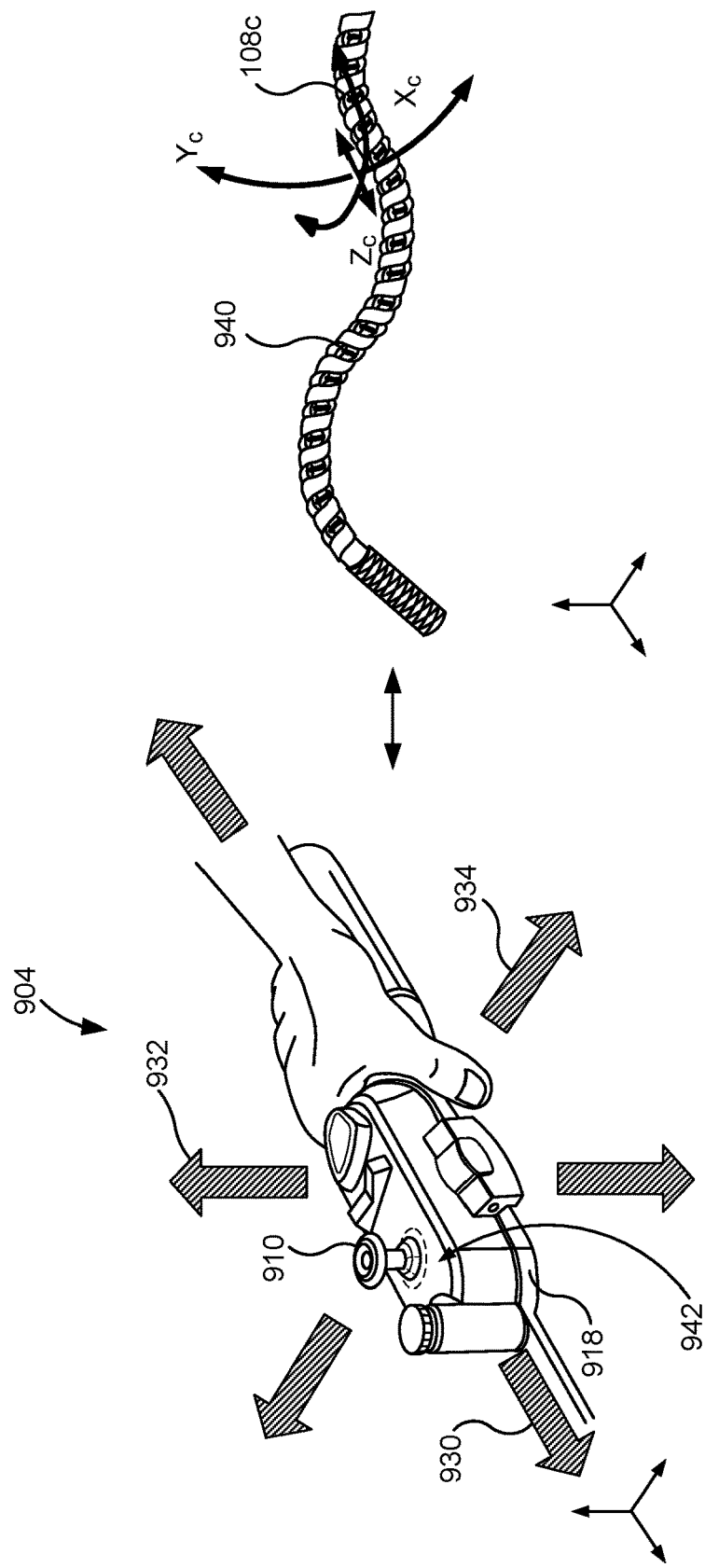

Referring now to FIGS. 35A, 35B, and TABLE 3, one simplified exemplary mapping of the input degrees of freedom of housing input device 904 to the articulated degrees of freedom of the three segment 908 of catheter 906 helps to illustrate how sensed movement of the housing can be used to help the user exercise control over a large number of articulation degrees of freedom, without having to include a large number of separate input devices or the like. For example, as shown in FIG. 35A, pitch 924 of housing 918 may optionally be coupled to vertical bending Yb of intermediate segment 108b, while yaw 928 of housing 918 may optionally be coupled to lateral bending Xb of the intermediate segment. Lateral translation 934 of housing 918 may be coupled to lateral bending Xc of proximal segment 108c, while vertical translation 932 of housing 918 may be coupled to vertical bending Yc of proximal segment 108c. Axial translation 930 of housing 918 may be coupled to axial elongation of any, some, or all of the segments Za, Zb, and/or Zc. While such relatively simplistic input/output mapping may be used in some embodiments, more sophisticated relationships between the user's command movements of the housing and the corresponding automated movements of the articulated catheter may help avoid confusion and improve ease-of-use.

TABLE 3

| INPUT | | OUTPUT | |
|---|---|---|---|
| Joystick | Xjoystick | Xa | Segment A |
| | Yjoystick | Ya | |

TABLE 3-continued

| INPUT | | | OUTPUT |
|---|---|---|---|
| Housing | Axial Translation | Za | |
| | Yaw | Xb | Segment B |
| | Pitch | Yb | |
| | Axial Translation | Zb | |
| | Lateral Translation | Xc | Segment C |
| | Vertical Translation | Yc | |
| | Axial Translation | Zc | |

Figure 35C:
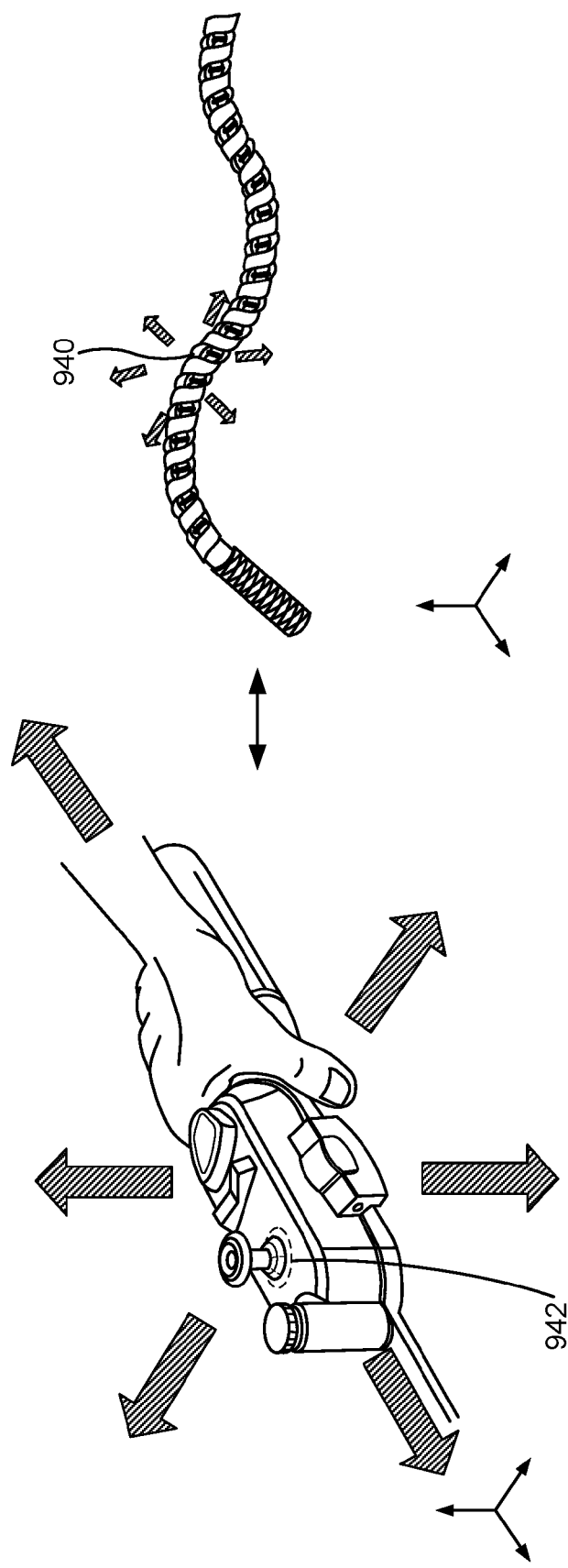

The mapping of the input degrees of freedom of housing 918 to the articulation degrees of freedom of catheter 906 couplings may, for example, be configured so as to at least roughly mimic movements near a desired location relative to the housing (such as coupling center 942 below joystick 910) in the induced movements of catheter 906 at a desired coupling center 940 of the catheter as if, for example, the hand of the user where grasping the catheter at or adjacent coupling center 940 (the coupling center optionally being adjacent where distal segment 908a is mounted to intermediate segment 908b). Even in the simple mapping of FIGS. 35A and 35B, lateral and vertical articulations of the intermediate segment, being immediately proximal of that location, will be largely coupled with the orientation of the shaft at coupling location 940 (though there will also be some translation), while lateral and vertical articulation of the proximal segment may be more coupled with translation at the coupling location as schematically illustrated in FIG. 35C (though there will also be some rotation). Other couplings may be somewhat more complex: Axial elongation of intermediate and proximal segments 908b, 908c may both be coupled with axial displacement of coupling location 940; axial elongation of distal segment 908a will not, but artificially coupling elongation of at least the distal and intermediate elongations Za, Zb with axial translation of the housing may extend the range of correlated axial translation and may not induce too much confusion. More generally, the system may take advantage of the excess articulation degrees of freedom provided by 3 or more segments with three degrees of freedom each to advance any of a wide variety of goals, including minimizing use of balloon inflation fluid, maintaining the segments near the centers of their ranges of motion and/or straight, inhibiting collisions of the catheter with itself, minimizing tissue engagement forces, and the like. Note that roll 926 of housing 918 may optionally alter the correlation between lateral and vertical bending (similar to varying the rotational alignment input 916) so as to maintain the appearance of grasping and rotating the segment about coupled location 940, relying on modification of the lateral and vertical transforms of the distal, intermediate, and optionally the proximal segment rather than directly coupling of an input degree of freedom of housing 918 to an associated articulation degree of freedom of catheter 906. Still further alternative goals may be achieved, for example, where first and second segments have helical structures that are wound in opposed directions, at a given location for the distal end of the catheter a roll orientation of the distal end about the Z axis can be controlled by adjusting a length of the first segment and compensating by appropriate adjustment of the second segment.

Referring now to FIG. 35D, a more sophisticated mapping of the movement of housing 918 will more likely take advantage of the control architecture to more effectively map input command movements of housing 918 to displayed movements of catheter 906, with movements of the housing in a single input degree of freedom often inducing combined movements of articulation degrees of freedom at a desired coupling location 940', so that the articulated catheter appears to move with output movements that correspond to those of the housing. For example, yaw 928 of housing 918 about input center 942 may result in a combination of elongation and lateral deflections of both the intermediate and proximal segment so as to more precisely mimic yaw at coupling location 940 than could be generated by articulation within any single segment. The desired combination of deflections may be calculated using an appropriate transformation for the forward and inverse kinematics, and by solving the vector units between the input and output. Similar mappings of pitch and yaw movements of the housing about input center 942 to pitch and yaw of the catheter about coupling location 940, and of the three translation degrees of freedom to translation degrees of freedom of the coupling location are shown in TABLE 4. These aligned mappings may help the user to maintain accurate control over the catheter by providing output movements that the user perceives as corresponding intuitively with input command movements.

TABLE 4

| INPUT | | OUTPUT | |
|---|---|---|---|
| Joystick | Xjoystick | Xa | Segment A |
| | Yjoystick | Ya | |
| Housing (motions sensed at coupling location of housing) | Axial Translation | Axial Translation | Segments A, B, and C (motions calculated at coupling location of catheter) |
| | Yaw | Yaw | |
| | Pitch | Pitch | |
| | Lateral Translation | Lateral Translation | |
| | Vertical Translation | Vertical Translation | |

In many embodiments, movement of housing 918 will only induce movement of catheter 906 while a clutch input 944 is being squeezed by the hand; releasing of the clutch may halt movement of catheter 906. Optionally, the input/output correlation between the housing and the catheter may provide a velocity controller so that movement of housing 918 while clutch input 944 is depressed may provide a velocity command, initiating movement of catheter 906 in the orientation of the housing movement and with a velocity proportional to the scale of the housing movement. Alternatively, an input/output correlation between the housing and the catheter may provide a position controller so that movement of housing 918 while clutch input 944 is depressed may provide a position command, initiating movement of catheter 906 in the orientation of the housing movement and for a distance proportional to the scale of the housing movement. In many embodiments, the coupling center on the catheter may be adjacent the proximal or distal end of the deliverable therapeutic or diagnostic tool, such as a prosthetic valve. This might be at a distal tip of the distal segment, and may make the user feel like they are holding a pair of pliers with something in the pliers, that something being the tool (such as the prosthetic valve).

Referring now to FIG. 35E, an alternative housing input device 960 includes a first housing portion 962 that can optionally be releasably attached to a second housing portion 964 (with alternative systems employing input devices and manifold housings that remain separate). Together, the first and second housing portions include some or all of the functional components described above regarding housing input device 902 of FIGS. 32A, 32B, 33B, 33C, 34, and 35A-35D. For example, first housing portion 962 will generally include articulation user interface components such as the housing motion sensing system (for providing movement commands to the processor), while second housing portion 964 will generally include the fluid supply canister, manifold, and receptacle for receiving the connector of the catheter. Both first housing portion 962 and second housing portion 964 may include a power source (such as a battery) and circuitry for wireless transmission of data between the user interface components and the valve manifold. The system processor may be included in first housing portion 962 or in second housing portion 964, but will often be distributed between the two, with at least some command signal processing being performed in the first housing portion and at least some valve signal processing being performed in the second housing portion. Optionally, corresponding electrical contacts of the portions engage when they are latched together to more efficiently transmit data and/or to share power, and alternative housing input device can be used as a single unit as described above. Alternatively, the user may detach first housing portion 962 from second housing portion 964, and may use the first housing portion to input movement commands to the catheter system by actuating the clutch and moving the first housing portion with a translational movement 930, 932, 934 and/or a rotational movement 924, 926 928 without having to manipulate the additional weight and volume of the second housing portion. The system user may optionally take and use first housing portion 962 at a distance (such as 1-10 meters) away from the patient, so as to decrease exposure of the system user to irradiation associated with fluoroscopy or the like. Alternatively, a second user interface housing portion or workstation may be provided with a radiation barrier disposed between the user and the patient. In still further alternative embodiments, two separate (rather than connectable) housings may be provided, and/or a flexible signal conduction cable or tether may couple the user input and manifold housings together (rather than relying on wireless telemetry).

Figure 36:
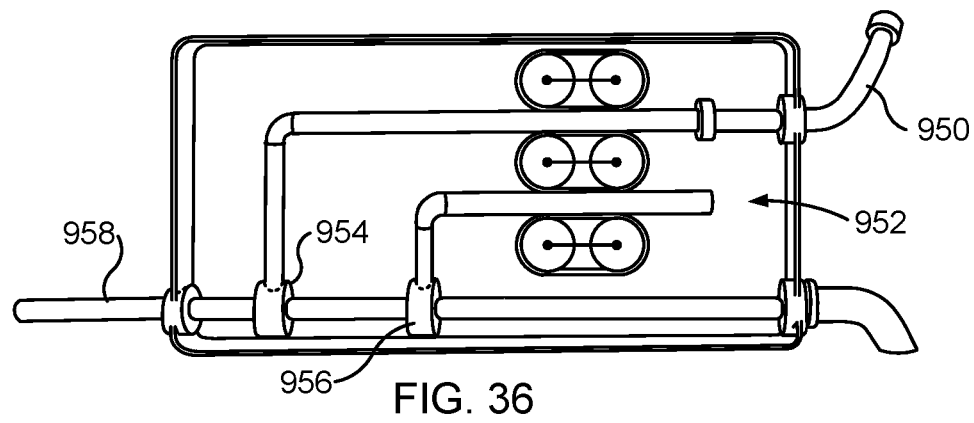
FIGS. 36 and 36A-36D schematically illustrate another alternative input system having a laterally flexible joystick that can be advanced axially to provide 3D input, and that is axially coupled to the catheter so that axial retraction of the joystick advances the proximal portion of the catheter.
Figure 36A:
Figure 36B:
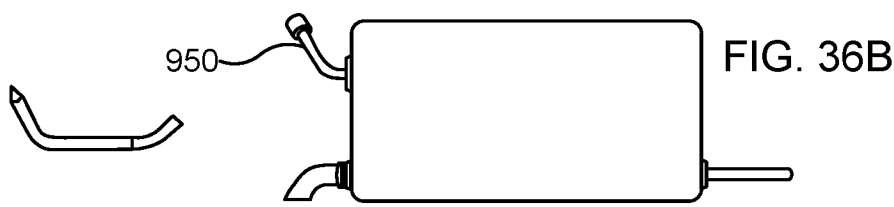
Figure 36C:
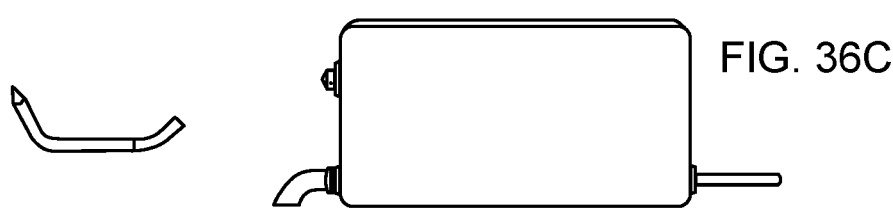
Figure 36D:
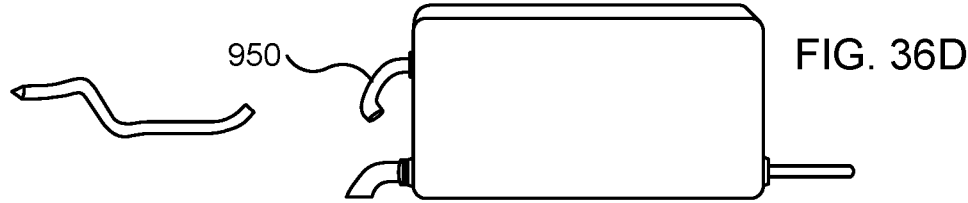

Referring now to FIGS. 36-36D, an alternative articulated catheter system has a flexible joystick input 950 system with a reverse drive system 952 and clutches 954, 956 so that the joystick can be axially decoupled from a catheter body 958, axially coupled to the catheter body (so that, for example, the catheter body moves in the same axial direction as the joystick when the user moves the joystick distally), or reverse coupled to the catheter body (so that, for example, the catheter body moves distally when the joystick is withdrawn proximally).

While the exemplary embodiments have been described in some detail for clarity of understanding and by way of example, a variety of modifications, changes, and adaptations of the structures and methods described herein will be obvious to those of skill in the art. Hence, the scope of the present invention is limited solely by the claims attached hereto.

What is claimed is:

1. A catheter articulation system for use by a user having a hand, the catheter articulation system comprising:
   an elongate catheter body having a proximal portion and an articulated distal portion with an axis therebetween, the distal portion of the catheter body being configured for insertion into a patient through an aperture, the proximal portion comprising a passively flexible unarticulated portion extending proximally from the distal portion;
   a plurality of actuators operatively coupled with the distal portion of the catheter body;
   a housing containing a battery and configured for supporting with the hand of the user;
   a sensor system mounted to the housing and configured to wirelessly couple with the proximal portion of the catheter body, the sensor system comprising an image capture device and an accelerometer and/or a gyroscope, the sensor system configured to measure movement of the housing in three or more degrees of freedom by the hand of the user, including translating of the housing and tilting of the housing, using image data from the image capture device so as to receive a movement command from movement of the hand supporting the housing; and
   a processor coupling the sensor system to the actuators so that the distal portion of the catheter body moves in correlation with the movement command.

2. The catheter articulation system of claim 1, wherein a two-dimensional touchscreen input device is mounted to the housing, the processor configured to move the distal portion of the catheter body in additional degrees of freedom in response to input received by the touchscreen input device.

3. The catheter articulation system of claim 1, wherein the sensor system comprises an at least 2D accelerometer and/or an at least 2D gyroscope, the movement command comprising tilting of the housing in at least two degrees of freedom.

4. The catheter articulation system of claim 1, wherein the sensor system comprises an at least 2D accelerometer, the movement command comprising translating the housing in at least two degrees of freedom.

5. The catheter articulation system of claim 1, wherein the housing is configured to be moved by the hand of the user in 6 degrees of freedom, wherein the sensor system receives the movement command in the 6 degrees of freedom.

6. The catheter articulation system of claim 1, further comprising a clutch input coupled to the processor, the processor configured to induce movement of the distal portion of the catheter in response to movement of the housing when the clutch input is actuated, and to inhibit commanded movement of the distal portion of the catheter in response to movement of the housing when the clutch input is not actuated.

7. The catheter articulation system of claim 1, wherein the processor is configured to induce aligned movement of the distal portion of the catheter body about a first coupling location along the axis in response to movement of the housing about a second coupling location so that the user perceives that the coupling locations correspond.

8. The catheter articulation system of claim 1, wherein the distal portion of the catheter includes an articulatable segment and a therapeutic or diagnostic tool distal of the articulatable segment, and wherein the first coupling location is disposed distal of the articulatable segment.

9. The catheter articulation system of claim 1, wherein the housing has an axis and further comprising a rotational alignment input coupled with the processor, the processor configured to alter a rotational alignment of a first lateral orientation about the axis of the catheter so as to correspond with a second lateral orientation about the axis of the housing in response to an alignment command received by the alignment input.

10. The catheter articulation system of claim 9, wherein the housing is elongate along the axis of the input body with a proximal portion and a distal portion differentiated from the proximal portion, and wherein the distal portion of the catheter body has an elongate image with a distal end visually identifiable when displayed on a remote imaging system so as to facilitate manual rotational alignment, by the user, of the input body with the image of the distal portion.

11. A catheter articulation system for use by a user having a hand so as to treat or diagnose a patient, the catheter articulation system configured for use with an imaging system including an image acquisition device and a display, the catheter articulation system comprising:
an elongate catheter body having a proximal portion and a distal portion with an axis therebetween, the distal portion of the catheter body being configured for insertion into a patient through an aperture and articulatable in three degrees of freedom or more, the proximal portion comprising a passively flexible unarticulated portion extending proximally from the distal portion;
a plurality of actuators operatively coupled with the distal portion of the catheter body;
an input system including an input body configured to facilitate reorientation by the hand of the user toward alignment with the display when the display is arranged to present to the user an image of the inserted distal portion of the catheter body within the patient, the input system further comprising a sensor coupled to the input body to receive a movement command having a command orientation, wherein the movement command comprises a three-dimensional movement command including a manual change in position and a manual change in orientation of the input body by the hand of the user; and
a processor configured for coupling the sensor to the actuators so that, during use, the distal portion of the catheter body moves, in response to the movement command, with a catheter movement having a movement orientation corresponding to the command orientation based on the reoriented input, wherein the processor determines a plurality of drive signals based on the alignment of the reoriented input with the display so that the movement orientation as shown to the user in the display is aligned with the command orientation.

12. The catheter articulation system of claim 11, wherein the sensor comprises an accelerometer, a gyroscope, an inertial measurement unit, an image capture device, and/or a flexible body shape sensor, the movement command comprising a movement of the input body, the input body containing the sensor.

13. The catheter articulation system of claim 11, wherein the sensor comprises an at least 2D accelerometer and/or an at least 2D gyroscope, the movement command comprising tilting of the input body in at least two degrees of freedom.

14. The catheter articulation system of claim 11, wherein the sensor comprises an at least 2D accelerometer, an image capture device, and/or a flexible shape body sensor, the movement command comprising translating the input body in at least two degrees of freedom.

15. The catheter articulation system of claim 11, wherein the input body is configured to be moved by the hand of the user in 6 degrees of freedom, wherein the sensor receives the movement command in the 6 degrees of freedom.

16. The catheter articulation system of claim 11, further comprising a clutch input coupled to the processor, the processor configured to induce movement of the distal portion of the catheter in response to movement of the input body when the clutch input is actuated, and to inhibit commanded movement of the distal portion of the catheter in response to movement of the input body when the clutch input is not actuated.

17. The catheter articulation system of claim 11, wherein the processor is configured to induce aligned movement of the distal portion of the catheter body about a first rotational coupling location along the axis in response to movement of the input body about a second rotational coupling location so that the user perceives that the coupling locations correspond.

18. The catheter articulation system of claim 11, wherein the distal portion of the catheter includes an articulatable segment and a therapeutic or diagnostic tool distal of the articulatable segment, and wherein the first rotational coupling location is disposed distal of the articulatable segment.

19. The catheter articulation system of claim 11, wherein the input body has an axis and further comprising a rotational alignment input coupled with the processor, the processor configured to alter a rotational alignment of a first lateral orientation about the axis of the catheter so as to correspond with a second lateral orientation about the axis of the input body in response to an alignment command received by the alignment input.

20. The catheter articulation system of claim 19, wherein the input body is elongate along the axis of the input body with a proximal portion and a distal portion differentiated from the proximal portion, and wherein the distal portion of the catheter body has an elongate image with a distal end visually identifiable when displayed on the display so as to facilitate manual rotational alignment, by the user, of the input body with the image of the distal portion.

* * * * *